United States Patent
Khanna et al.

(10) Patent No.: US 6,900,232 B2
(45) Date of Patent: May 31, 2005

(54) CYCLOALKYL ALKANOIC ACIDS AS INTEGRIN RECEPTOR ANTAGONISTS

(75) Inventors: Ish Kumar Khanna, Libertyville, IL (US); Michael Clare, Skokie, IL (US); Alan F. Gasiecki, Vernon Hills, IL (US); Thomas Rogers, Ballwin, MO (US); Barbara Chen, Northbrook, IL (US); Mark Russell, Gurnee, IL (US); Hwang-Fun Lu, Manchester, MO (US)

(73) Assignee: Pharmacia Corporation, Peapack, NJ (US)

( * ) Notice: Subject to any disclaimer, the term of this patent is extended or adjusted under 35 U.S.C. 154(b) by 0 days.

(21) Appl. No.: 09/882,186

(22) Filed: Jun. 15, 2001

(65) Prior Publication Data

US 2002/0077321 A1 Jun. 20, 2002

Related U.S. Application Data

(60) Provisional application No. 60/211,781, filed on Jun. 15, 2000.

(51) Int. Cl.$^7$ ............... A61K 31/44; C07D 213/72
(52) U.S. Cl. ............... 514/352; 546/312; 546/194; 546/318
(58) Field of Search ............... 546/312; 514/352

(56) References Cited

U.S. PATENT DOCUMENTS

| | | | |
|---|---|---|---|
| 3,654,306 A | 4/1972 | German | 260/326.5 |
| 5,665,754 A | 9/1997 | Feldman et al. | 514/397 |
| 5,741,796 A | 4/1998 | Hartman et al. | 514/300 |
| 5,773,646 A | 6/1998 | Chandrakumar et al. | 562/439 |
| 5,849,736 A | 12/1998 | Wityak et al. | 514/227.8 |
| 5,852,210 A | 12/1998 | Chen et al. | 562/439 |

FOREIGN PATENT DOCUMENTS

| | | |
|---|---|---|
| EP | 0 478 328 B1 | 1/1996 |
| EP | 0747346 | 2/2000 |
| EP | 0 671 392 B1 | 2/2001 |
| GB | 2 264 115 A | 8/1993 |
| JP | 10287634 | 10/1998 |
| WO | WO 93/21166 | 10/1993 |
| WO | WO9427947 | 12/1994 |
| WO | WO9503288 | 2/1995 |
| WO | WO 95/32710 | 12/1995 |
| WO | WO 96/41795 | 12/1996 |
| WO | WO 97/12878 | 4/1997 |
| WO | WO9719049 | 5/1997 |
| WO | WO 98/20871 | 5/1998 |
| WO | WO 98/31359 | 7/1998 |
| WO | WO 99/45927 | 9/1999 |
| WO | WO0033838 | 6/2000 |
| WO | WO 00/38665 | 7/2000 |
| WO | WO 00/38715 | 7/2000 |
| WO | WO 00/38719 | 7/2000 |
| WO | WO 00/38786 | 7/2000 |
| WO | WO 00/64888 | 11/2000 |
| WO | WO0068195 | 11/2000 |
| WO | WO 01/14337 A1 | 3/2001 |
| WO | WO 01/14338 A1 | 3/2001 |

OTHER PUBLICATIONS

J. Wityak et. al., *Discovery of Potent Isoxazoline Glycoprotein IIb/IIIa Receptor Antagonists*, 1997, J. Med. Chem. 40, 50–60.

W. H. Miller et. al., *Discovery of Orally Active Nonpeptide Vitronectin Receptor Antagonists Based on a 2–Benzazepine Gly–Asp Mimetic*, 2000, J. Med. Chem. 43, 22–26.

Primary Examiner—Richard L. Raymond
Assistant Examiner—Kahsay Habte
(74) Attorney, Agent, or Firm—Rachel A. Polster

(57) ABSTRACT

The present invention relates to a class of compounds represented by the Formula I Wherein $A^1$ is a pyridinyl of the formula optionally substituted by one or more $R^k$ selected from the group consisting of hydroxy, alkyl, alkoxy, alkoxyalkyl, thioalkyl, haloalkyl, cyano, amino alkylamino, halogen, acylamino, sulfonamide and —COR; and R is hydroxy, alkoxy, alkyl or amino; and pharmaceutically acceptable salt thereof, pharmaceutical compositions comprising compounds of the Formula I, and methods of selectively inhibiting or antagonizing the $\alpha_v\beta_3$ and/or $\alpha_v\beta_5$ integrin.

65 Claims, No Drawings ns and as such are useful in pharmaceutical compositions
CYCLOALKYL ALKANOIC ACIDS AS INTEGRIN RECEPTOR ANTAGONISTS The present application claims priority under Title 35, United States Code, §119 of U.S. Provisional application Ser. No. 60/211,781 filed Jun. 15, 2000.

FIELD OF THE INVENTION

The present invention relates to pharmaceutical agents (compounds) which are $\alpha_v\beta_3$ and/or $\alpha_v\beta_5$ integrin antagonists and as such are useful in pharmaceutical compositions and in methods for treating conditions mediated by $\alpha_v\beta_3$ and/or $\alpha_v\beta_5$ integrins.

BACKGROUND OF THE INVENTION

The integrin $\alpha_v\beta_3$ (also known as vitronectin receptor), is a member of the integrin family of heterodimeric transmembrane glycoprotein complexes that mediate cellular adhesion events and signal transduction processes. Integrin $\alpha_v\beta_3$ is expressed in number of cell types and has been shown to mediate several biologically relevant processes, including adhesion of osteoclasts to the bone matrix, vascular smooth muscle cell migration and angiogenesis.

The integrin $\alpha_v\beta_3$ has been shown to play a role in various conditions or disease states including tumor metastasis, solid tumor growth (neoplasia), osteoporosis, Paget's disease, humoral hypercalcemia of malignancy, osteopenia, angiogenesis, including tumor angiogenesis and lymphangiogenesis, retinopathy including macular degeneration, arthritis, including rheumatoid arthritis, periodontal disease, psoriasis and smooth muscle cell migration (e.g. restenosis artherosclerosis). The compounds of the present invention are $\alpha_v\beta_3$ antagonists and can be used, alone or in combination with other therapeutic agents, in the treatment or modulation of various conditions or disease states described above. Additionally, it has been found that such agents would be useful as antivirals, antifungals and antimicrobials.

The integrin $\alpha_v\beta_5$ is thought to play a role in neovascularization. M. C. Friedlander, et al., Science, 270, 1500–1502 (1995) disclose that a monoclonal antibody for $\alpha_v\beta_5$ inhibits VEFG-induced angiogenesis in the rabbit cornea and the chick chorioallantoic membrane model. Therefore compounds which act as antagonists of the $\alpha_v\beta_5$ integrin will inhibit neovascularization and will be useful for treating and preventing angiogenesis metastasis, tumor growth, macular degeneration and diabetic retionopathy.

Certain compounds may antagonize both the $\alpha_v\beta_5$ and the $\alpha_v\beta_3$ receptor and therefore are referred to as "mixed $\alpha_v\beta_5/\alpha_v\beta_3$ antagonists" or "dual $\alpha_v\beta_3/\alpha_v\beta_5$ antagonists". Such dual or mixed antagonists are useful for treating or preventing angiogenesis, tumor metastasis, tumor growth, diabetic retinopathy, macular degeneration, atherosclerosis and osteoporosis.

It has been shown that the $\alpha_v\beta_3$ integrin and other $\alpha_v$ containing integrins bind to a number of Arg-Gly-Asp (RGD) containing matrix macromolecules. Compounds containing the RGD sequence mimic extracellular matrix ligands so as to bind to cell surface receptors. However, it is also known that RGD peptides in general are non-selective for RGD dependent integrins. For example, most RGD peptides which bind to $\alpha_v\beta_3$ also bind to $\alpha_v\beta_5$, $\alpha_v\beta_1$ and $\alpha_{IIb}\beta_3$. Antagonism of platelet $\alpha_{IIb}\beta_3$ (also known as the fibrinogen receptor) is known to block platelet aggregation in humans. In order to avoid bleeding side-effects when treating the conditions or disease states associated with the integrin $\alpha_v\beta_3$, it would be beneficial to develop compounds which are selective antagonists of $\alpha_v\beta_3$ as opposed to $\alpha_{IIb}\beta_3$.

Tumor cell invasion occurs by a three step process: 1) tumor cell attachment to extracellular matrix; 2) proteolytic dissolution of the matrix; and 3) movement of the cells through the dissolved barrier. This process can occur repeatedly and can result in metastases at sites distant from the original tumor.

Seftor et al. (Proc. Natl. Acad. Sci. USA, Vol. 89 (1992) 1557–1561) have shown that the $\alpha_v\beta_3$ integrin has a biological function in melanoma cell invasion. Montgomery et al., (Proc. Natl. Acad. Sci. USA, Vol. 91 (1994) 8856–60) have demonstrated that the integrin $\alpha_v\beta_3$ expressed on human melanoma cells promotes a survival signal, protecting the cells from apoptosis. Mediation of the tumor cell metastatic pathway by interference with the $\alpha_v\beta_3$ integrin cell adhesion receptor to impede tumor metastasis would be beneficial.

Further, with the discovery that $\alpha_v\beta_3$ plays a role in the process of lymphatic dissemination via adhesion of melanoma cells to lymph node by binding the vitronectin receptor (Nip et al, J Clin Invest 1992, 90,1406), inhibitors of $\alpha_v\beta_3$ may also be useful for making alterations in lymphatic endothelial-tumorcell adhesion, thereby further reducing the potential for tumor metastasis.

Brooks et al. (Cell, Vol. 79 (1994) 1157–1164) have demonstrated that antagonists of $\alpha_v\beta_3$ provide a therapeutic approach for the treatment of neoplasia (inhibition of solid tumor growth) since systemic administration of $\alpha_v\beta_3$ antagonists causes dramatic regression of various histologically distinct human tumors.

The compounds of the present invention are useful for the treatment, including prevention of angiogenic disorders. The term angiogenic disorders include conditions involving abnormal neovascularization. The growth of new blood vessels, or angiogenesis, also contributes to pathological conditions such as diabetic retinopathy including macular degeneration (Adamis et al., Amer. J. Ophthal., Vol. 118, (1994) 445–450) and rheumatoid arthritis (Peacock et al., J. Exp. Med., Vol. 175, (1992), 1135–1138). Therefore, $\alpha_v\beta_3$ antagonists would be useful therapeutic agents for treating such conditions associated with neovascularization (Brooks et al., Science, Vol. 264, (1994), 569–571).

It has been reported that the cell surface receptor $\alpha_v\beta_3$ is the major integrin on osteoclasts responsible for attachment to bone (for a review, see Rodan and Rodan, 1997, J. Endocrinol. 154, S47, Nakamura et al., J. Cell Science, 1999 112, 3985). Osteoclasts cause bone resorption and when such bone resorbing activity exceeds bone forming activity it leads to an increased number of bone fractures, incapacitation and increased mortality. Antagonists of $\alpha_v\beta_3$ have been shown to be potent inhibitors of osteoclastic activity both in vitro (Sato et al., J. Cell. Biol., Vol. 111 (1990) 1713–1723) and in vivo (Fisher et al., Endocrinology, Vol. 132 (1993) 1411–1413). Antagonism of $\alpha_v\beta_3$ leads to decreased bone resorption and therefore restores a normal balance of bone forming and resorbing activity. Thus it would be beneficial to provide antagonists of osteoclast $\alpha_v\beta_3$ which are effective inhibitors of bone resorption and therefore are useful in the treatment or prevention of osteoporosis.

The role of the $\alpha_v\beta_3$ integrin in smooth muscle cell migration also makes it a therapeutic target for prevention or inhibition of neointimal hyperplasia which is a leading cause of restenosis after vascular procedures (Choi et al., J. Vasc.

Surg. Vol. 19(1) (1994) 125–34). Prevention or inhibition of neointimal hyperplasia by pharmaceutical agents to prevent or inhibit restenosis would be beneficial.

White (*Current Biology*, Vol. 3(9)(1993) 596–599) has reported that adenovirus uses $\alpha_v\beta_3$ for entering host cells. The integrin appears to be required for endocytosis of the virus particle and may be required for penetration of the viral genome into the host cell cytoplasm. Thus compounds which inhibit $\alpha_v\beta_3$ would find usefulness as antiviral agents.

SUMMARY OF THE INVENTION

The compounds of this invention are 1) $\alpha_v\beta_3$ integrin antagonists; or 2) $\alpha_v\beta_5$ integrin antagonists; or 3) mixed or dual $\alpha_v\beta_3/\alpha_v\beta_5$ antagonists. The present invention includes compounds which inhibit the respective integrins and also includes pharmaceutical compositions comprising such compounds. The present invention further provides for methods for treating or preventing conditions mediated by the $\alpha_v\beta_3$ and/or $\alpha_v\beta_5$ receptors in a mammal in need of such treatment comprising administering a therapeutically effective amount of the compounds of the present invention and pharmaceutical compositions of the present invention. Administration of such compounds and compositions of the present invention inhibits angiogenesis, tumor metastasis, tumor growth, osteoporosis, Paget's disease, humoral hypercalcemia of malignancy, retinopathy, macular degeneration, arthritis, periodontal disease, smooth muscle cell migration, including restenosis and artherosclerosis, and viral diseases.

Further, it has been found that the selective antagonism of the $\alpha_v\beta_3$ integrin is desirable in that the $\alpha_v\beta_6$ integrin may play a role in normal physiological processes of tissue repair and cellular turnover that routinely occur in the skin and pulmonary tissue, and $\alpha_v\beta_8$ may play a role in the regulation of growth in the human pathway. Therefore, compounds which selectively inihibit the $\alpha_v\beta_3$ integrin as opposed to the $\alpha_v\beta_6$ and/or the $\alpha_v\beta_8$ integrin have reduced side-effects associated with inhibtion of the $\alpha_v\beta_6$ and/or the $\alpha_v\beta_8$ integrin. It is therefore another object of the present invention to provide compounds that are selective antagonists of $\alpha_v\beta_3$ and/or $\alpha_v\beta_5$ as opposed to $\alpha_v\beta_6$, and it is yet another object of the present invention to provide compounds that are selective antagonists of $\alpha_v\beta_3$ and/or $\alpha_v\beta_5$ as opposed to $\alpha_v\beta_8$.

The present invention relates to a class of compounds represented by the Formula I

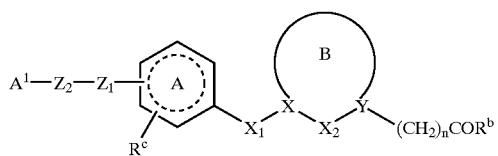

or a pharmaceutically acceptable salt thereof, wherein

is a 4–8 membered monocyclic ring or a 7–12 membered bicyclic ring, which ring is optionally saturated or unsaturated; which ring is optionally substituted with one or more substituent selected from the group consisting of alkyl, haloalkyl, aryl, heteroaryl, halogen, alkoxyalkyl, aminoalkyl, hydroxy, nitro, alkoxy, hydroxyalkyl, thioalkyl, amino, alkylamino, arylamino, alkylsulfonamide, acyl, acylamino, alkylsulfone, sulfonamide, allyl, alkenyl, methylenedioxy, ethylenedioxy, alkynyl, carboxamide, cyano, and $-(CH_2)_n$ COR wherein n is 0–2 and R is hydroxy, alkoxy, alkyl or amino;

$A^1$ is a 5–9 membered monocyclic ring or 7–12 membered bicyclic heterocycle ring of the formula

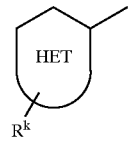

containing at least one nitrogen atom and optionally containing 1 to 4 heteroatoms, selected from the group consisting of O, N, S, $SO_2$ and CO; optionally saturated or unsaturated; optionally substituted by one or more $R^k$ is selected from the group consisting of hydroxy, alkyl, alkoxy, alkoxyalkyl, thioalkyl, cyano, amino, alkylamino, haloalkyl, halogen, acylamino, sulfonamide and —COR wherein R is hydroxy, alkoxy, alkyl or amino;

or $A^1$ is

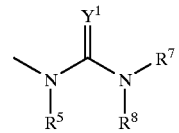

wherein $Y^1$ is selected from the group consisting of N—$R^2$, O, and S;

$R^2$ is selected from the group consisting of H; alkyl; aryl; hydroxy; alkoxy; cyano; amido; alkylcarbonyl; arylcarbonyl; alkoxycarbonyl; aryloxycarbonyl; haloalkylcarbonyl; haloalkoxycarbonyl; alkylthiocarbonyl; arylthiocarbonyl; acyloxymethoxycarbonyl;

$R^2$ taken together with $R^7$ forms a 4–12 membered dinitrogen containing heterocycle optionally substituted with one or more substituent selected from the group consisting of lower alkyl, thioalkyl, alkylamino, hydroxy, keto, alkoxy, halo, phenyl, amino, carboxyl or carboxyl ester;

or $R^2$ taken together with $R^7$ forms a 4–12 membered heterocycle containing one or more heteroatom selected from O, N and S optionally unsaturated;

or $R^2$ taken together with $R^7$ forms a 5 membered heteroaromatic ring fused with a aryl or heteroaryl ring;

$R^7$ (when not taken together with $R^2$) and $R^8$ are independently selected from the group consisting of H; alkyl; aralkyl; amino; alkylamino; hydroxy; alkoxy; arylamino; amido, alkylcarbonyl, arylcarbonyl; alkoxycarbonyl; aryloxy; aryloxycarbonyl; haloalkylcarbonyl; haloalkoxycarbonyl; alkylthiocarbonyl; arylthiocarbonyl; acyloxymethoxycarbonyl; cycloalkyl; bicycloalkyl; aryl; acyl; benzoyl;

or $NR^7$ and $R^8$ taken together form a 4–12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S; $R^5$ is selected from the group consisting of H, and alkyl;

or

A is

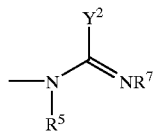

wherein Y is selected from the group consisting of alkyl; cycloalkyl; bicycloalkyl; aryl; monocyclic heterocycles;

$Z_1$ is selected from the group consisting of $CH_2$, $CH_2O$, O, NH, $NR_k$, CO, S, SO, CH(OH), and $SO_2$, wherein $R_k$ is selected from H or lower alkyl;

$Z_2$ is a 1–5 carbon linker optionally containing one or more heteroatom selected from the group consisting of O, S and N; alternatively $Z_1$–$Z_2$ may further contain a carboxamide, sulfone, oxime, sulfonamide, alkenyl, alkynyl, or acyl group;

wherein the carbon and nitrogen atoms of $Z_1$–$Z_2$ are optionally substituted by alkyl, alkoxy, thioalkyl, alkylsulfone, aryl, alkoxyalkyl, hydroxy, alkylamino, heteroaryl, alkenyl, alkynyl, carboxyalkyl, halogen, haloalkyl or acylamino;

wherein $Z_2$–$Z_1$ is attached to

at the para or meta position relative to the $X_1$ substituent;

n is an integer 0, 1 or 2;

$R^c$ is selected from the group consisting of hydrogen; alkyl; halogen, hydroxy, nitro, alkoxy, amino, haloalkyl, aryl, heteroaryl, alkoxyalkyl, aminoalkyl, hydroxyalkyl, thioalkyl, alkylamino, arylamino, alkylsulfonylamino, acyl, acylamino, sulfonyl, sulfonamide, allyl, alkenyl, methylenedioxy, ethylenedioxy, alkynyl, alkynylalkyl, carboxy, alkoxycarbonyl, carboxamido, cyano, and —$(CH_2)_n$—COR wherein n is 0–2 and R is selected from hydroxy, alkoxy, alkyl and amino;

$X_1$ is selected from the group consisting of —O—, CO, $SO_2$, $NR^m$ and $(CHR^p)_q$; wherein $R^m$ is H or alkyl; $R^p$ is H, alkyl, alkoxy or hydroxy and q is 0 or 1;

$X_2$ is selected from the group consisting of —$CHR^e$—, CO, $SO_2$, O, $NR^f$ and S;

$R^e$ is selected from the group consisting of H, alkyl, hydroxy and alkoxy; $R^f$ is H or alkyl;

X or Y are independently selected from the group consisting of —$CR^g$— or —N— wherein $R^g$ is selected from the group consisting of H, alkyl, haloalkyl, fluoro, alkoxyalkyl, alkynyl, aryl, heteroaryl, aralkyl, alkylsulfone, heteroaralkyl, hydroxy, alkoxy, hydroxyalkyl, and carboxyalkyl;

The group X—$X_2$—Y optionally contains a moiety selected from the group consisting of acyl, alkyl, amino, ether, thioether, sulfone, and olefin;

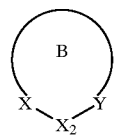

forms a 3–8 membered monocyclic ring system; or an 8–11 membered bicyclic system; optionally saturated or unsaturated; the monocyclic ring system optionally containing 1–2 heteroatoms selected from N, O and S; the bicyclic ring system optionally containing 1–4 heteroatoms selected from N, O, S or optionally containing the group such as $SO_2$ or CO); and optionally substituted with one or more substituent selected from the group consisting of alkyl, halogen, cyano, carboalkoxy, haloalkyl, alkoxyalkyl, alkylsulfone, aryl, heteroaryl, aralkyl, heteroaralkyl or alkoxy;

$R^b$ is $X_3$-$R^h$ wherein $X_3$ is selected from the group consisting of O, S and $NR^j$ wherein $R^h$ and $R^j$ are independently selected from the group consisting of H, alkyl, acyl, aryl, aralkyl and alkoxyalkyl; and and ni s 0, 1 or 2.

It is another object of the invention to provide pharmaceutical compositions comprising compounds of the Formula I. Such compounds and compositions are useful in selectively inhibiting or antagonizing the $\alpha_V\beta_3$ and/or $\alpha_V\beta_5$ integrin(s) and therefore in another embodiment the present invention relates to a method of selectively inhibiting or antagonizing the $\alpha_V\beta_3$ and/or $\alpha_V\beta_5$ integrin(s). The invention further involves treating or inhibiting pathological conditions associated therewith such as osteoporosis, humoral hypercalcemia of malignancy, Paget's disease, tumor metastasis, solid tumor growth (neoplasia), angiogenesis, including tumor angiogenesis, retinopathy including macular degeneration and diabetic retinopathy, arthritis, including rheumatoid arthritis, periodontal disease, psoriasis, smooth muscle cell migration including restenosis or atherosclerosis in a mammal in need of such treatment. Additionally, such pharmaceutical agents are useful as antiviral agents, antifungals and antimicrobials. The compounds of the present invention may be used alone or in combination with other pharmaceutical agents.

DETAILED DESCRIPTION

The present invention relates to a class of compounds represented by the Formula I, described above.

In another embodiment of the present invention

is aryl or fused aryl optionally substituted by one or more substituent selected from lower alkyl, halogen, alkoxy, hydroxy, cyano, amino, alkylamino, dialkylamino or methylsulfonamide.

Another embodiments of

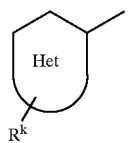

include the following heterocyclic ring systems containing at least one nitrogen atom:

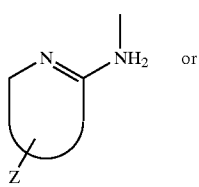

B2

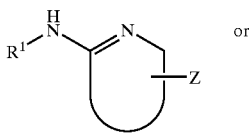

B3

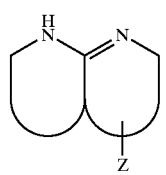

B4 wherein $R^1$ is H, alkyl, alkoxyalkyl, acyl, hydroxyalkyl, haloalkyl, or alkoxycarbonyl; and Z is H, alkyl, alkoxy, hydroxy, amino, alkylamino, carboxyl, alkoxycarbonyl, hydroxyalkyl, halogen or haloalkyl.

More specifically another embodiments include pyridylamino, imidazolylamino, oxazolylamino, thiazolylamino, pyrimidinylamino, quinoline, isoquinoline, morpholinopyridine, tetrahydronaphthyridine, tetrahydroquinoline, imidazopyridine, benzimidazole, pyridone or quinolone.

The following heteroaryls include the ring systems as described above.

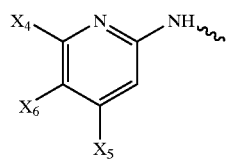 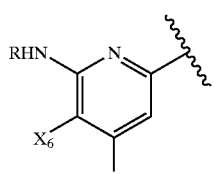

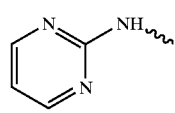

B = $CH_2$, O, CO, S, $CF_2$, $SO_2$, NR
R' = OR, OH, Me  n = 1 or 2

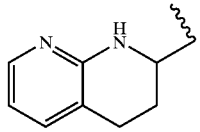 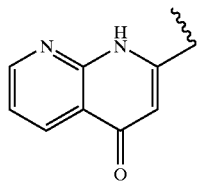

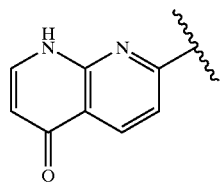 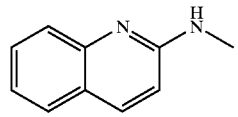

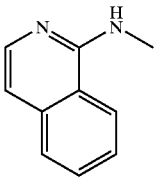 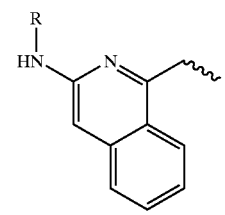

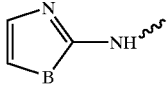 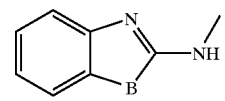

B = NH, NMe, O, S       B = NH, O, S

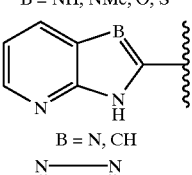 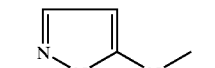

B = N, CH              B = NH, O, S

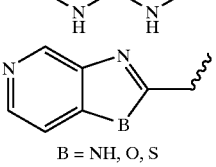 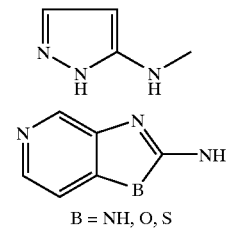

B = NH, O, S           B = NH, O, S

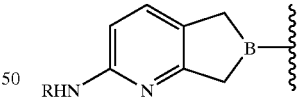 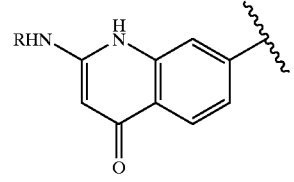

B = N, CH
R = H, Me

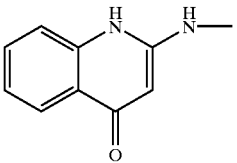 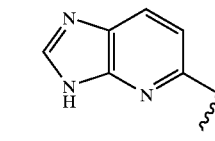

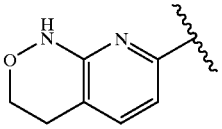 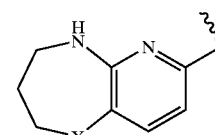

R' = OR, OH, Me, H
X = O, S, NR, $SO_2$, $CF_2$

-continued

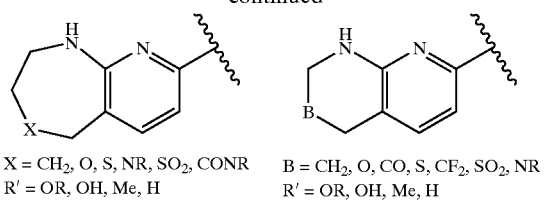

X = CH$_2$, O, S, NR, SO$_2$, CONR
R' = OR, OH, Me, H

B = CH$_2$, O, CO, S, CF$_2$, SO$_2$, NR
R' = OR, OH, Me, H

For the pyridyl derived heterocycle, the substituents $X_4$ and $X_5$ are preferentially H, alkyl, branched alkyl, alkylamino, alkoxyalkylamino, haloalkyl, thioalkyl, halogen, amino, alkoxy, aryloxy, alkoxyalkyl, hydroxy, cyano or acylamino groups. In another embodiment of the invention, the substituents $X_4$ and $X_5$ can be methyl, methoxy, amine, methylamine, dimethylamine, hydroxy, chloro, bromo, fluoro, trifluoromethyl and cyano. $X_6$ may preferentially be H, alkyl, halogen (F, Cl) alkoxy or haloalkyl. Alternately, the pyridyl ring can be fused with a 4–8 membered ring, optionally saturated or unsaturated. Some examples of these ring systems include quinoline, azaquinoline, tetrahydroquinoline, imidazopyridine and the like. The monocyclic ring systems such as imidazole, thiazole, oxazole, and the like, may contain an amino or alkylamino substituent at any position within the ring.

In another embodiment of the present invention, when $Z_1$ of Formula 1 is CO or SO$_2$, the linkage $A^1$-$Z_2$ of Formula I preferentially includes the following heterocycle derived ring systems: pyridine, imidazole, thiazole, oxazole, benzimidazole, imidazopyridine and the like.

Other preferred heterocycles formed by the $A_1$–$Z_2$ moiety of the present invention include

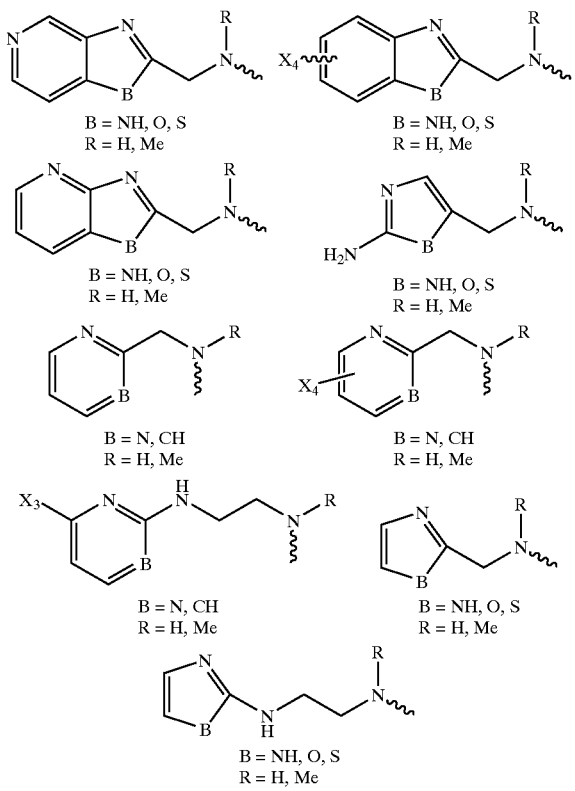

The substituent RC is preferably alkyl, halogen, alkoxy, hydroxy, cyano, a carboxyl derivative or methyl sulfonamide.

The invention further relates to pharmaceutical compositions containing therapeutically effective amounts of the compounds of Formula I.

The invention also relates to a method of selectively inhibiting or antagonizing the $\alpha_V\beta_3$ integrin and/or the $\alpha_V\beta_5$ integrin and more specifically relates to a method of inhibiting bone resorption, periodontal disease, osteoporosis, humoral hypercalcemia of malignancy, Paget's disease, tumor metastasis, solid tumor growth (neoplasia), angiogenesis, including tumor angiogenesis, retinopathy including macular degeneration and diabetic retinopathy, arthritis, including rheumatoid arthritis, smooth muscle cell migration, including restenosis and atherosclerosis by administering a therapeutically effective amount of a compound of the Formula I to achieve such inhibition together with a pharmaceutically acceptable carrier.

The following is a list of definitions of various terms used herein:

As used herein, the terms "alkyl" or "lower alkyl" refer to a straight chain or branched chain hydrocarbon radicals having from about 1 to about 10 carbon atoms, and more preferably 1 to about 6 carbon atoms. Examples of such alkyl radicals are methyl, ethyl, n-propyl, isopropyl, n-butyl, isobutyl, sec-butyl, t-butyl, pentyl, neopentyl, hexyl, isohexyl, and the like.

As used herein the terms "alkenyl" or "lower alkenyl" refer to unsaturated acyclic hydrocarbon radicals containing at least one double bond and 2 to about 6 carbon atoms, which carbon—carbon double bond may have either cis or trans geometry within the alkenyl moiety, relative to groups substituted on the double bond carbons. Examples of such groups are ethenyl, propenyl, butenyl, isobutenyl, pentenyl, hexenyl and the like.

As used herein the terms "alkynyl" or "lower alkynyl" refer to acyclic hydrocarbon radicals containing one or more triple bonds and 2 to about 6 carbon atoms. Examples of such groups are ethynyl, propynyl, butynyl, pentynyl, hexynyl and the like.

The term "cycloalkyl" as used herein means saturated or partially unsaturated cyclic carbon radicals containing 3 to about 8 carbon atoms and more preferably 4 to about 6 carbon atoms. Examples of such cycloalkyl radicals include cyclopropyl, cyclopropenyl, cyclobutyl, cyclopentyl, cyclohexyl, 2-cyclohexen-1-yl, and the like.

The term "aryl" as used herein denotes aromatic ring systems composed of one or more aromatic rings. Preferred aryl groups are those consisting of one, two or three aromatic rings. The term embraces aromatic radicals such as phenyl, pyridyl, naphthyl, thiophene, furan, biphenyl and the like.

As used herein, the term "cyano" is represented by a radical of the formula 2

The terms "hydroxy" and "hydroxyl" as used herein are synonymous and are represented by a radical of the formula 3

The term "lower alkylene" or "alkylene" as used herein refers to divalent linear or branched saturated hydrocarbon radicals of 1 to about 6 carbon atoms.

As used herein the term "alkoxy" refers to straight or branched chain oxy containing radicals of the formula —$OR^{20}$, wherein $R^{20}$ is an alkyl group as defined above. Examples of alkoxy groups encompassed include methoxy, ethoxy, n-propoxy, n-butoxy, isopropoxy, isobutoxy, sec-butoxy, t-butoxy and the like.

As used herein the terms "arylalkyl" or "aralkyl" refer to a radical of

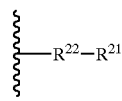

the formula4 wherein $R^{21}$ is aryl as defined above and $R^{22}$ is an alkylene as defined above. Examples of aralkyl groups include benzyl, pyridylmethyl, naphthylpropyl, phenethyl and the like.

As used herein the term "nitro" is represented by a radical of the formula 5

As used herein the term "halo" or "halogen" refers to bromo, chloro, fluoro or iodo.

As used herein the term "haloalkyl" refers to alkyl groups as defined above substituted with one or more of the same or different halo groups at one or more carbon atom. Examples of haloalkyl groups include trifluoromethyl, dichloroethyl, fluoropropyl and the like.

As used herein the term "carboxyl" or "carboxy" refers to a radical of the formula —COOH.

As used herein the term "carboxyl ester" refers to a radical of the formula —$COOR^{23}$ wherein $R^{23}$ is selected from the group consisting of H, alkyl, aralkyl or aryl as defined above.

As used herein the term "carboxyl derivative" refers to a radical of the formula

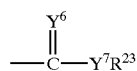

6 wherein $Y^6$ and $Y^7$ are independently selected from the group consisting of O, N or S and $R^{23}$ is selected from the group consisting of H, alkyl, aralkyl or aryl as defined above.

As used herein the term "amino" is represented by a radical of the formula —$NH_2$.

As used herein the term "alkylsulfonyl" or "alkylsulfone" refers to a radical of the

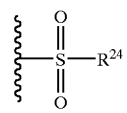

formula7 wherein $R^{24}$ is alkyl as defined above.

As used herein the term "alkylthio" refers to a radical of the formula —$SR^{24}$ wherein R is alkyl as defined above.

As used herein the term "sulfonic acid" refers to a radical of the

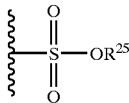

formula8 wherein $R^{25}$ is alkyl as defined above.

As used herein the term "sulfonamide" or "sulfonamido" refers to a radical of the

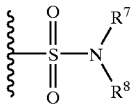

formula 9 wherein $R^7$ and $R^8$ are as defined above.

As used herein the term "fused aryl" refers to an aromatic ring such as the aryl groups defined above fused to one or more phenyl rings. Embraced by the term "fused aryl" is the radical naphthyl and the like.

As used herein the terms "monocyclic heterocycle" or "monocyclic heterocyclic" refer to a monocyclic ring containing from 4 to about 12 atoms, and more preferably from 5 to about 10 atoms, wherein 1 to 3 of the atoms are heteroatoms selected from the group consisting of oxygen, nitrogen and sulfur with the understanding that if two or more different heteroatoms are present at least one of the heteroatoms must be nitrogen. Representative of such monocyclic heterocycles are imidazole, furan, pyridine, oxazole, pyran, triazole, thiophene, pyrazole, thiazole, thiadiazole, and the like.

As used herein the term "fused monocyclic heterocycle" refers to a monocyclic heterocycle as defined above with a benzene fused thereto. Examples of such fused monocyclic heterocycles include benzofuran, benzopyran, benzodioxole, benzothiazole, benzothiophene, benzimidazole and the like.

As used herein the term "methylenedioxy" refers to the

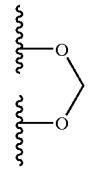

radical and the term "ethylenedioxy" refers to the radical

1011 As used herein the term "4–12 membered dinitrogen containing heterocycle refers to a radical of the formula

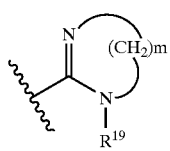

12 wherein m is an integer 1 to 1 and $R^{19}$ is H, alkyl, aryl, or aralkyl and more preferably refers to 4–9 membered ring and includes rings such as imidazoline.

As used herein the term "5-membered optionally substituted heteroaromatic ring" includes for example a radical of the formula

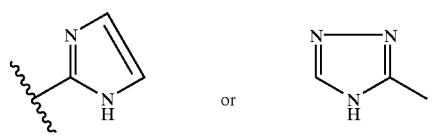

and "5-membered heteroaromatic ring fused with a phenyl" refers to such a "5-membered heteroaromatic ring" with a phenyl fused thereto. Representative of such 5-membered heteroaromatic rings fused with a phenyl is benzimidazole.

As used herein the term "bicycloalkyl" refers to a bicyclic hydrocarbon radical containing 6 to about 12 carbon atoms which is saturated or partially unsaturated.

As used herein the term "acyl" refers to a radical of the formula 13

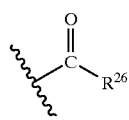

wherein $R^{26}$ is alkyl, alkenyl, alkynyl, aryl or aralkyl and optionally substituted thereon as defined above. Encompassed by such radical are the groups acetyl, benzoyl and the like.

As used herein the term "thio" refers to a radical of the formula 14

As used herein the term "sulfonyl" refers to a radical of the formula 15

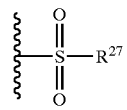

wherein $R^{27}$ is alkyl, aryl or aralkyl as defined above.

As used herein the term "haloalkylthio" refers to a radical of the formula —S—$R^{28}$ wherein $R^{28}$ is haloalkyl as defined above.

As used herein the term "aryloxy" refers to a radical of the formula 16

wherein $R^{29}$ is aryl as defined above.

As used herein the term "acylamino" refers to a radical of the formula

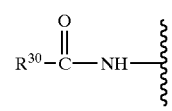

wherein $R^{30}$ is alkyl, aralkyl or aryl as defined above.

As used herein the term "amido" refers to a radical of the formula 17

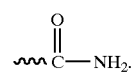

As used herein the term "alkylamino" refers to a radical of the formula —$NHR^{32}$ wherein $R^{32}$ is alkyl as defined above.

As used herein the term "dialkylamino" refers to a radical of the formula —$NR^{33}R^{34}$ wherein $R^{33}$ and $R^{34}$ are the same or different alkyl groups as defined above.

As used herein the term "trifluoromethyl" refers to a radical of the formula 18

As used herein the term "trifluoroalkoxy" refers to a radical of the formula 19

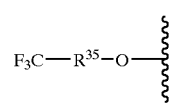

wherein $R^{35}$ is a bond or an alkylene as defined above.

As used herein the term "alkylaminosulfonyl" or "alkylsulfonamide" refer to a radical of the formula 20

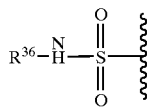

wherein $R^{36}$ is alkyl as defined above.

As used herein the term "alkylsulfonylamino" refers to a radical of the formula 21

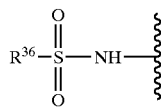

wherein $R^{36}$ is alkyl as defined above.

As used herein the term "trifluoromethylthio" refers to a radical of the formula 22

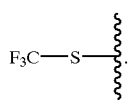

As used herein the term "trifluoromethylsulfonyl" refers to a radical of the formula 23

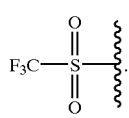

As used herein the term "4–12 membered mono-nitrogen containing monocyclic or bicyclic ring" refers to a saturated or partially unsaturated monocyclic or bicyclic ring of 4–12 atoms and more preferably a ring of 4–9 atoms wherein one atom is nitrogen. Such rings may optionally contain additional heteroatoms selected from nitrogen, oxygen or sulfur. Included within this group are morpholine, piperidine, piperazine, thiomorpholine, pyrrolidine, proline, azacycloheptene and the like.

As used herein the term "benzyl" refers to the radical

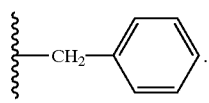

24

As used herein the term "phenethyl" refers to the radical

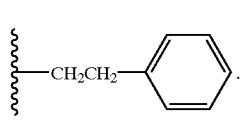

25

As used herein the term "4–12 membered mono-nitrogen containing monosulfur or monooxygen containing heterocyclic ring" refers to a ring consisting of 4 to 12 atoms and more preferably 4 to 9 atoms wherein at least one atom is a nitrogen and at least one atom is oxygen or sulfur. Encompassed within this definition are rings such as thiazoline and the like.

As used herein the term "alkylcarbonyl" refers to a radical of the formula 26

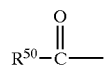 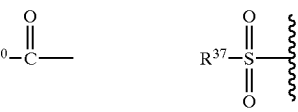

wherein $R^{50}$ is alkyl as defined above.

As used herein the term "arylcarbonyl" refers to a radical of the formula 27

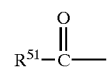

wherein $R^{50}$ is aryl as defined above.

As used herein the term "alkoxycarbonyl" refers to a radical of the formula 28

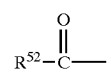

wherein $R^{52}$ is alkoxy as defined above.

As used herein the term "aryloxycarbonyl" refers to a radical of the formula 29

wherein $R^{51}$ is aryl as defined above.

As used herein the term "haloalkylcarbonyl" refers to a radical of the formula 30

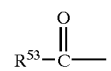

wherein $R^{53}$ is haloalkyl as defined above.

As used herein the term "haloalkoxycarbonyl" refers to a radical of the formula 31

wherein $R^{53}$ is haloalkyl as defined above.

As used herein the term "alkylthiocarbonyl" refers to a radical of the formula 32

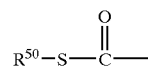

wherein $R^{50}$ is alkyl as defined above.

As used herein the term "arylthiocarbonyl" refers to a radical of the formula 33

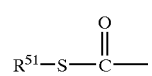

wherein $R^{51}$ is aryl as defined above.

As used herein the term "acyloxymethoxycarbonyl" refers to a radical of the formula 34

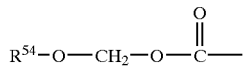

wherein $R^{54}$ is acyl as defined above.

As used herein the term "arylamino" refers to a radical of the formula $R^{51}$—NH— wherein $R^{51}$ is aryl as defined above.

As used herein the term "alkylamido" refers to a radical of the formula 35

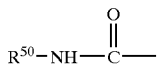

wherein $R^{50}$ is alkyl as defined above.

As used herein the term "N,N-dialkylamido" refers to a radical of the formula 36

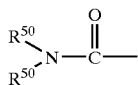

wherein $R^{50}$ is the same or different alkyl group as defined above.

As used herein the term "acyloxy" refers to a radical of the formula $R^{55}$—O— wherein $R^{55}$ is acyl as defined above.

As used herein the term "alkenylene" refers to a linear hydrocarbon radical of 1 to about 8 carbon atoms containing at least one double bond.

As used herein the term "alkoxyalkyl" refers to a radical of the formula

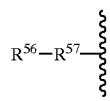

wherein $R^{56}$ is alkoxy as defined above and $R^{57}$ is alkylene as defined above.

As used herein the term "alkynylalkyl" refers to a radical of the formula $R^{59}$—$R^{60}$— wherein $R^{59}$ is alkynyl as defined as above and $R^{60}$ is alkylene as defined as above.

As used herein the term "alkynylene" refers to divalent alkynyl radicals of 1 to about 6 carbon atoms.

As used herein the term "allyl" refers of a radical of the formula —CH$_2$CH=CH$_2$.

As used herein the term "aminoalkyl" refers to a radical of the formula H$_2$N—$R^{61}$ wherein $R^{61}$ is alkylene as defined above.

As used herein the term "benzoyl" refers to the aryl radical C$_6$H$_5$—CO—.

As used herein the terms "carboxamide" or "carboxamido" refer to a radical of the formula —CO—NH$_2$.

As used herein the term "carboxyalkyl" refers to a radical HOOC—$R^{62}$— wherein $R^{62}$ is alkylene as defined as above.

As used herein the term "carboxylic acid" refers to the radical —COOH As used herein the term "ether" refers to a radical of the formula $R^{60}$— wherein $R^{63}$ is selected from the group consisting of alkyl, aryl and heteroaryl.

As used herein the term "haloalkylsulfonyl" refers to a radical of the formula

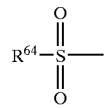

wherein the $R^{64}$ is haloalkyl as defined above.

As used herein the term "heteroaryl" refers to an aryl radical contain at least one heteroatom.

As used herein the term "hydroxyalkyl" refers to a radical of the formula HO—$R^{65}$— wherein $R^{65}$ is alkylene as defined above.

As used herein the term "keto" refers to a carbonyl group joined to 2 carbon atoms.

As used herein the term "lactone" refers to an anhydro cyclic ester produced by intramolecular condensation of a hydroxy acid with the elimination of water.

As used herein the term "olefin" refers to an unsaturated hydrocarbon radical of the type $C_nH_{2n}$.

As used herein the term "sulfone" refers to a radical of the formula $R^{66}$—SO$_2$—.

As used herein the term "thioalkyl" refers to a radical of the formula $R^{77}$—S— wherein $R^{77}$ is alkyl as defined above.

As used herein the term "thioether" refers to a radical of the formula $R^{78}$—S— wherein $R^{77}$ is alkyl, aryl or heteroaryl.

As used herein the term "trifluoroalkyl" refers to an alkyl radical as defined above substituted with three halo radicals as defined above.

The term "composition" as used herein means a product which results from the mixing or combining of more than one element or ingredient.

The term "pharmaceutically acceptable carrier", as used herein means a pharmaceutically acceptable material, composition or vehicle, such as a liquid or solid filler, diluent, excipient, solvent or encapsulating material, involved in carrying or transporting a chemical agent.

The term "therapeutically effective amount" shall mean that amount of drug or pharmaceutical agent that will elicit the biological or medical response of a tissue, system or animal that is being sought by a researcher or clinician.

The following is a list of abbreviations and the corresponding meanings as used interchangeably herein:

$^1$H-NMR=proton nuclear magnetic resonance
AcOH=acetic acid
Bn=benzyl
Boc=tert-butoxycarbonyl
Cat.=catalytic amount
CH$_2$Cl$_2$=dichloromethane
CH$_3$CN=acetonitrile
CHN analysis=carbon/hydrogen/nitrogen elemental analysis
DIBAL=diisobutylaluminum hydride
Dl water=deionized water
DMF=N,N-dimethylformamide
DMSO=dimethylsulfoxide
Et=ethyl
EtI=ethyliodide
Et$_2$O=diethyl ether
Et$_3$N=triethylamine
EtOAc=ethyl acetate
ETOH=ethanol
g=gram(s)

HPLC=high performance liquid chromatography
i-Pr=iso propyl
i-Prop=iso propyl
$K_2CO_3$=potassium carbonate
KOH=potassium hydroxide
L=Liter
LiOH=lithium hydroxide
Me=methyl
MeI=methyl iodide
MeOH=methanol
mg=milligram
$MgSO_4$=magnesium sulfate
ml=milliliter
mL=milliliter
MS=mass spectroscopy
MTBE=methyl t-butyl ether
$N_2$=nitrogen
NaH—sodium hydride
$NaHCO_3$=sodium bicarbonate
NaOH=sodium hydroxide
NaOMe=sodium methoxide
$Na_2PO_4$=sodium phosphate
$Na_2SO_4$=sodium sulfate
$NH_4HCO_3$=ammonium bicarbonate
$NH_4^+HCO2^-$=ammonium formate
$NH_4OH$=ammonium hydroxide
NMR=nuclear magnetic resonance
Pd=palladium
Pd/C=palladium on carbon
Ph=phenyl
Pt=platinum
Pt/C=platinum on carbon
RPHPLC=reverse phase high performance liquid chromatography
RT=room temperature
T-BOC=tert-butoxycarbonyl
TFA=trifluoroacetic acid
THF=tetrahydrofuran
Δ=heating the reaction mixture The compounds as shown above can exist in various isomeric forms and all such isomeric forms are meant to be included. Tautomeric forms are also included as well as pharmaceutically acceptable salts of such isomers and tautomers.

In the structures and formulas herein, a bond drawn across a bond of a ring can be to any available atom on the ring.

The term "pharmaceutically acceptable salt" refers to a salt prepared by contacting a compound of Formula I with an acid whose anion is generally considered suitable for human consumption. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid. Representative salts include the following: benzenesulfonate, hydrobromide and hydrochloride. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. All of the pharmacologically acceptable salts may be prepared by conventional means. (See Berge et al., *J. Pharm. Sci.*, 66(1), 1–19 (1977) for additional examples of pharmaceutically acceptable salts.) The compounds of the present invention can have chiral centers and occur as racemates, racemic mixtures, diastereomeric mixtures, and as individual diastereomers or enantiomers, with all isomeric forms included in the present invention. Therefore, where a compound is chiral, the separate enantiomers or diastereomers, substantially free of the other, are included within the scope of the present invention; further included are all mixtures of the enantiomers or diastereomers. Also included within the scope of the invention are polymorphs, or hydrates or other modifiers of the compounds of invention.

The present invention includes within its scope prodrugs of the compounds of this invention. In general, such prodrugs will be functional derivatives of the compounds of this invention which are readily convertible in vivo into the required compound. For example, prodrugs of a carboxylic acid may include an ester, an amide, or an ortho-ester. Thus, in the methods of treatment of the present invention, the term "administering" shall encompass the treatment of the various conditions described with the compound specifically disclosed or with a compound which may not be specifically disclosed, but which converts to the compound of Formula I in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

For the selective inhibition or antagonism of $\alpha_V\beta_3$ and/or $\alpha_V\beta_5$ integrins, compounds of the present invention may be administered orally, parenterally, or by inhalation spray, or topically in unit dosage formulations containing conventional pharmaceutically acceptable carriers, adjuvants and vehicles. The term parenteral as used herein includes, for example, subcutaneous, intravenous, intramuscular, intrasternal, transmuscular infusion techniques or intraperitonally.

The compounds of the present invention are administered by any suitable route in the form of a pharmaceutical composition adapted to such a route, and in a dose effective for the treatment intended. Therapeutically effective doses of the compounds required to prevent or arrest the progress of or to treat the medical condition are readily ascertained by one of ordinary skill in the art using preclinical and clinical approaches familiar to the medicinal arts.

Accordingly, the present invention provides a method of treating conditions mediated by selectively inhibiting or antagonizing the $\alpha_V\beta_3$ and/or $\alpha_V\beta_5$ cell surface receptor which method comprises administering a therapeutically effective amount of a compound selected from the class of compounds depicted in the above formulas, wherein one or more compound is administered in association with one or more non-toxic, pharmaceutically acceptable carriers and/or diluents and/or adjuvants (collectively referred to herein as "carrier" materials) and if desired other active ingredients. More specifically, the present invention provides a method for selective antagonism of the $\alpha_V\beta_3$ and/or $\alpha_V\beta_5$ cell surface receptors over $\alpha_{IIb}\beta_3$ or $\alpha_v\beta_5$ integrin receptors. Most preferably the present invention provides a method for inhibiting bone resorption, treating osteoporosis, inhibiting humoral hypercalcemia of malignancy, treating Paget's disease, inhibiting tumor metastasis, inhibiting neoplasia (solid tumor growth), inhibiting angiogenesis including tumor angiogenesis, treating retinopathy including macular degeneration and diabetic retinopathy, inhibiting arthritis, psoriasis and periodontal disease, and inhibiting smooth muscle cell migration including restenosis.

Based upon standard laboratory experimental techniques and procedures well known and appreciated by those skilled in the art, as well as comparisons with compounds of known usefulness, the compounds of Formula I can be used in the treatment of patients suffering from the above pathological conditions. One skilled in the art will recognize that selection of the most appropriate compound of the invention is within the ability of one with ordinary skill in the art and will depend on a variety of factors including assessment of results obtained in standard assay and animal models.

Treatment of a patient afflicted with one of the pathological conditions comprises administering to such a patient an amount of compound of the Formula I which is therapeutically effective in controlling the condition or in prolonging the survivability of the patient beyond that expected in the absence of such treatment. As used herein, the term "inhibition" of the condition refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially controlled to some extent.

As stated previously, the compounds of the invention can be used in a variety of biological, prophylactic or therapeutic areas. It is contemplated that these compounds are useful in prevention or treatment of any disease state or condition wherein the $\alpha_V \beta_3$ and/or $\alpha_V \beta_5$ integrin plays a role.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 1.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100, 200 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittant throughout the dosage regiment.

For administration to a mammal in need of such treatment, the compounds in a therapeutically effective amount are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions useful in the present invention may be subjected to conventional pharmaceutical operations such as sterilization and/or may contain conventional pharmaceutical adjuvants such as preservatives, stabilizers, wetting agents, emulsifiers, buffers, etc.

The general synthetic sequences for preparing the compounds useful in the present invention are outlined in SCHEMES 1–11. Both an explanation of, and the actual procedures for, the various aspects of the present invention are described where appropriate. The following SCHEMES and EXAMPLES are intended to be merely illustrative of the present invention, and not limiting thereof in either scope or spirit. Those with skill in the art will readily understand that known variations of the conditions and processes described in the SCHEMES and EXAMPLES can be used to synthesize the compounds of the present invention.

SCHEME 1

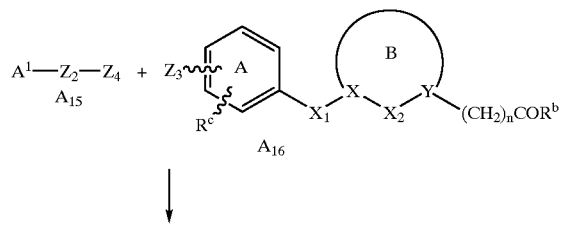

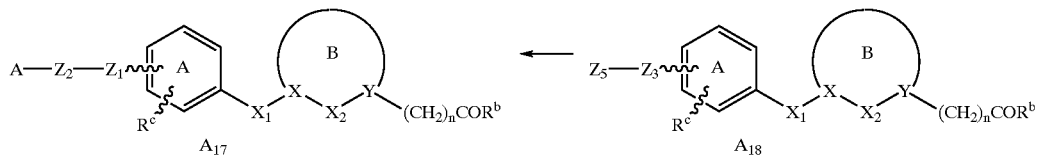

SCHEME 1

The compounds of FORMULA $A_{17}$ are generally prepared by reacting an intermediate of formula $A_{16}$ with a compound of the formula $A_{15}$. For example, when $Z_3$ is a (OH, SH or NHR), $A_{16}$ may be alkylated with $A_{15}$ ($Z_4$=Br or OMs) using base such as (sodium hydride, potassium hydride) preferably in a solvent such as dimethylsulfoxide or DMF. These reactions may preferentially be carried at 0° C. to approximately 40° C. Alternately, when $Z_3$ and $Z_4$ are both OH, the ether formation to product $A_{17}$ may be accomplished by using Mitsunobu reaction. This reaction may preferentially be carried out using triarylphosphine (such as triphenylphoshine) and dialkylazodicarboxylate (such as diethyl azodicarboxylate, di-tert-butyl azodicarboxylate, di-iso-propyl azodicarboxylate) in solvents such as DMF, methylene chloride, THF and the like. When $Z_3$ carries a carboxylic acid or a sulfonic acid and $Z_4$ is an amine, standard coupling conditions may be used to synthesize the target $A_{17}$ compounds containing carboxamide (CONH) or the sulfonamide ($SO_2NH$).

Alternately, the compounds of FORMULA $A_{17}$ may be prepared by starting with compounds of general formula $A_{18}$. For example, when $Z_5$ in $A_{18}$ is $NH_2$, cyclic or acyclic guanidino containing compounds of formula $A_{17}$ may be synthesized by adopting the methodologies set forth in e.g. U.S. Pat. Nos. 5,852,210, and 5,773,646, hereby incorporated by reference. Similarly, compounds of formula $A_{18}$ ($Z_5$=$NH_2$) may be treated with appropriately substituted heteroaromatic system (such as 2-halopyridine N-oxide) to give the target compound $A_{17}$. This reaction may preferentially be carried out by refluxing the intermediate $A_{18}$ and 2-halopyridine (such as 2-fluoropyridine, 2-chloropyridine N-oxide) in solvents such as tert-butyl alcohol, tert-amyl alcohol in the presence of base (such as sodium bicarbonate, sodium carbonate, potassium carbonate, potassium bicarbonate).

When compounds of formula $A_{17}$ contain N-oxide (e.g., pyridine N-oxide), the deoxygenation is preferentially carried out using transfer hydrogenation conditions (such as cyclohexene/Pd on carbon or ammonium formate and Pd on carbon. When $R^b$ is OR, the hydrolysis of the resulting ester may be carried out using an aqueous base such as sodium hydroxide, lithium hydroxide, potassium hydroxide and using co-solvents as methanol, ethanol or THF.

Compounds of the general formula $A_{15}$, $A_{16}$, $A_{18}$ may be prepared by methodologies discussed in SCHEMES 2–11 which follow.

SCHEME 2

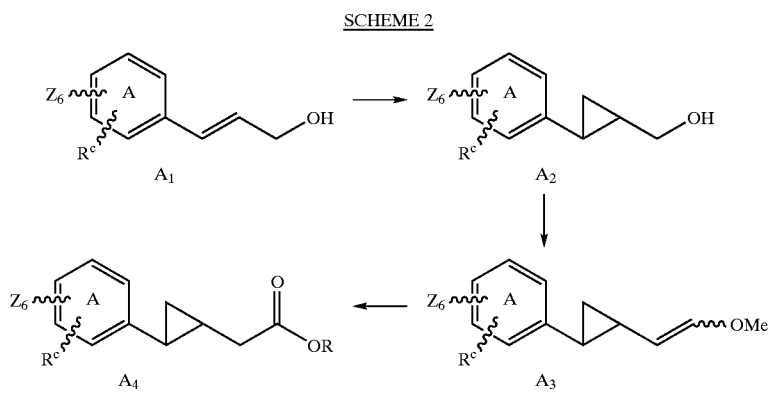

SCHEME 2

Compounds of the FORMULA $A_4$ may be prepared by starting with a substituted cinnamyl alcohol of formula $A_1$. The compounds of formula $A_1$ may be synthesized from the corresponding cinnamic acid or its esters by reduction with e.g.; DIBAL, lithium borohydride or the like. Cyclopropanation of $A_1$ using Simmons-Smith reaction gives the cyclopropyl containing intermediate $A_2$. The conditions described in e g.; *Chem. Letts;* 61–64,1992; *Bull. Chem. Soc.*, Japan, 70, 207–217,1997 and the references cited therein may be used for this reaction. Oxidation of resulting alcohol (using e.g., oxalyl chloride, DMSO) followed by homologation, as described in *Tetrahedron Lett* 25, 4549–4552,1984, gives the enol ether $A_3$. Hydrolysis of the enol ether $A_3$ with e.g., 1N HCl and oxidation of the resulting aldehyde with e.g.; silver nitrate gives the acid $A_4$. The acid may be esterified using an alcohol (such as ethanol) and an acid catalyst. The intermediate $A_4$ is processed to the compounds of Formula I by synthetic transformations as outlined in SCHEME 1.

SCHEME 3

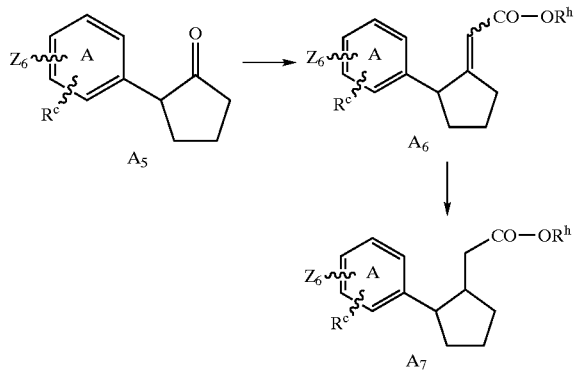

SCHEME 3

Compounds of FORMULA $A_7$ containing a cyclopentyl ring may be prepared by starting with readily accessible intermediate $A_5$ by reaction of 2-chloro-cyclopentanone with aryl magnesium halide (see e.g, Can. J. Chem., 70,1274–1280, 1992; Chem. Pharm. Bull., 34, 3599,1986). Using Wittig or Horner-Emmons reaction, the compound $A_5$ is converted to the olefin containing intermediate $A_6$. This reaction is carried out using trialkyl phosphonoacetate (such as triethyl phosphonoacetate, trimethyl phosphonoacetate) and a base (e.g., sodium hydride, sodium methoxide, sodium ethoxide). This reaction is generally done at low temperature (0–30° C.) and using THF, DMF as solvents. The isomeric mixtures of olefin containing compounds are hydrogenated using e.g., Pd on carbon or Pt on carbon as catalyst. This reduction is carried under pressure of hydrogen (preferably 5–60 psi) to give the desired intermediate $A_7$. The intermediate $A_7$ is processed to the compounds of Formula I by synthetic transformations outlined in SCHEME 1.

SCHEME 4

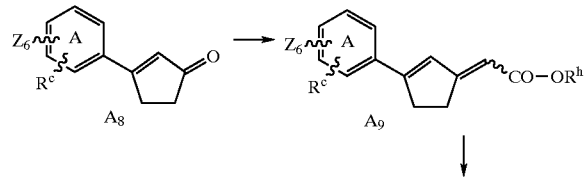

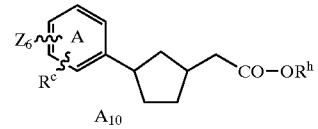

SCHEME 4

Compounds of FORMULA I with a cyclopentyl ring substituted in a 1,3-arrangement are prepared by starting with readily accessible intermediate $A_8$. The methodology described in e.g.; J. Am. Chem. Soc. 67, 286, 1945; or J. Med. Chem., 33, 2828, 1990 may be used to synthesize $A_8$ with a variety of substituents on the aryl ring. Elaboration of carbonyl functionality of $A_8$ to intermediate $A_{10}$ may be accomplished in a similar manner as described in SCHEME 3. The intermediate $A_8$ is processed to the compounds of Formula I by synthetic transformations outlined in SCHEME 1.

SCHEME 5

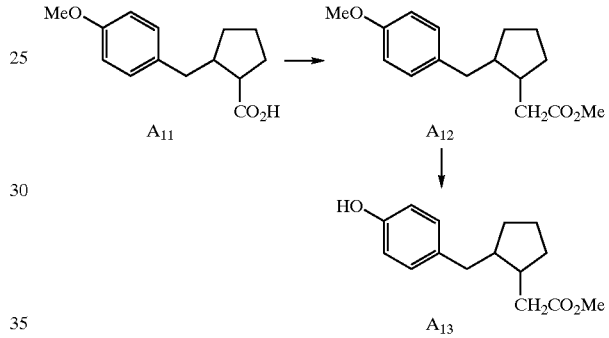

SCHEME 5

Compounds of FORMULA I, wherein $X_1$ is $CH_2$ are prepared starting with commercially accessible intermediate $A_{11}$. Reduction of the carboxylic acid functionality in $A_{11}$ with e g; diborane or lithium aluminum hydride gives the hydroxymethyl derivative which may be elaborated to $CH_2CO_2R$ functionality using the methodology elaborated in EXAMPLE 1. Demethylation of the intermediate with a boron trihalide such as boron tribromide, boron trichloride gives the demethylated intermediates $A_{13}$ which is processed to the compounds of Formula I by synthetic transformations as outlined in SCHEME 1.

SCHEME 6

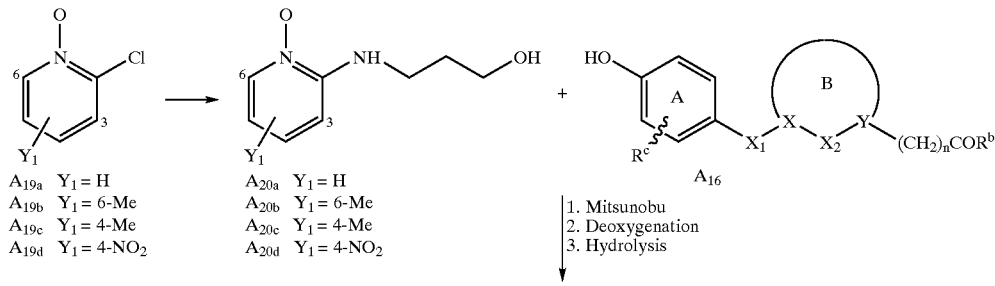

$A_{19a}$ $Y_1 = H$
$A_{19b}$ $Y_1 = 6\text{-Me}$
$A_{19c}$ $Y_1 = 4\text{-Me}$
$A_{19d}$ $Y_1 = 4\text{-NO}_2$ $A_{20a}$ $Y_1 = H$
$A_{20b}$ $Y_1 = 6\text{-Me}$
$A_{20c}$ $Y_1 = 4\text{-Me}$
$A_{20d}$ $Y_1 = 4\text{-NO}_2$ 1. Mitsunobu
2. Deoxygenation
3. Hydrolysis

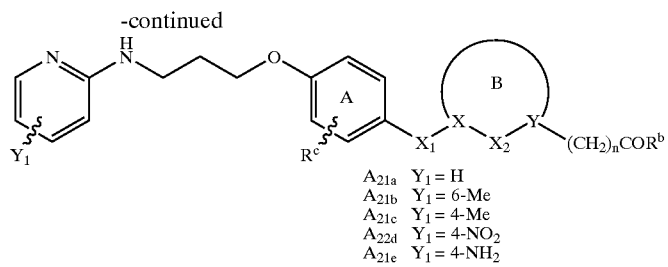

| $A_{21a}$ | $Y_1$ = H |
| $A_{21b}$ | $Y_1$ = 6-Me |
| $A_{21c}$ | $Y_1$ = 4-Me |
| $A_{22d}$ | $Y_1$ = 4-NO$_2$ |
| $A_{21e}$ | $Y_1$ = 4-NH$_2$ |

SCHEME 6

The compounds of FORMULA I, wherein $A^1$ is substituted pyridyl may be prepared by adopting the general synthetic SCHEME 6. For example, reaction of substituted 2-halopyridine N-oxide (such as $A_{19a}$–$A_{19d}$) with e.g. 3-aminopropanol gives the intermediates $A_{20a}$–$A_{20d}$. This reaction may preferentially be carried out by refluxing the intermediate 2-halopyridine N-oxide (such as 2-chloropyridine N-oxide) in solvents such as tert-butyl alcohol, tert-amyl alcohol in the presence of base (such as sodium bicarbonate, sodium carbonate, potassium carbonate, potassium bicarbonate). The preparative conditions described in WO 99/15508 (PCT U.S. 98/19466) may be used for this transformation.

Coupling of the intermediates $A_{20a}$–$A_{20d}$ with $A_{16}$ using Mitsunobu reaction gives the compounds containing the ether link. This reaction may preferentially be carried out using triarylphosphine (such as triphenylphoshine) and dialkylazodicarboxylate (such as diethyl azodicarboxylate, di-tert-butyl azodicarboxylate, di-iso-propyl azodicarboxylate) in solvents such as DMF, methylene chloride, or THF. N-Deoxygenation of resulting intermediates followed by hydrolysis of the ester gives the compounds ($A_{21a}$–$A_{21d}$).

Reduction of the N-oxide bond may be accomplished using e.g., transfer hydrogenation (cyclohexene/Pd on carbon) or ammonium formate and Pd on carbon. The nitro group in $A_{21d}$ may be hydrogenated using Pd on carbon or Pt on carbon as catalysts. This transformation may be carried out using solvents such as methanol, ethanol or THF. The hydrolysis of the ester group may be carried using aqueous base (such as sodium hydroxide, lithium hydroxide or potassium hydroxide) in solvents such as methanol, ethanol and THF.

Compounds of Formula I containing a heterocycle other than pyridyl can also be prepared using the methodology of SCHEME 6. For example reaction of 2-bromopyrimidine or 1-chloroisoquinoline N-oxide with 3-amino-propanol gives the analogous intermediates as obtained in STEP 1 of SCHEME 6. The resulting intermediates could be elaborated as in SCHEME 6 to give the pyrimidine and isoquinoline containing compounds of FORMULA I.

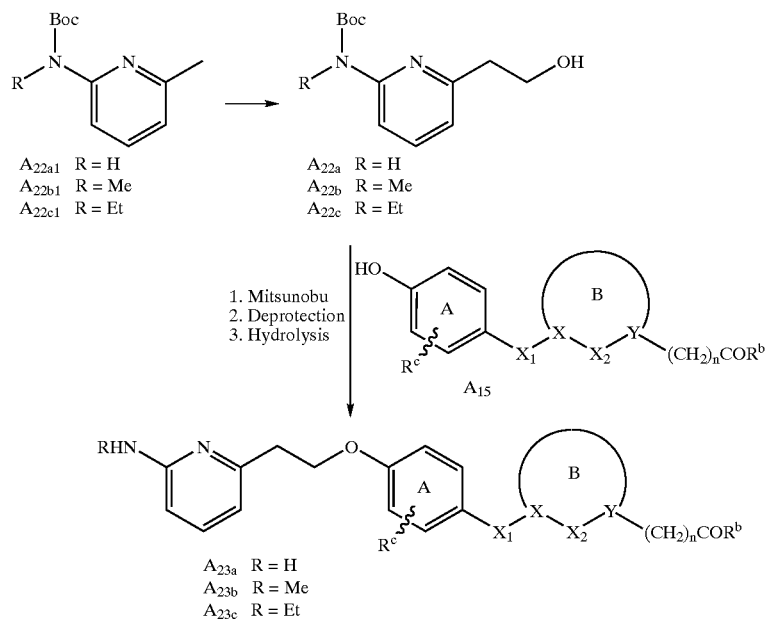

SCHEME 7

Compounds of FORMULA I containing 6-amino substituents may be prepared as shown in SCHEME 7. The intermediate $A_{22b}$ can be prepared as described in J. Med. Chem 43, 22, 2000. Boc-protected 2-amino-6-picoline ($A_{22a1}$) or its ethylated derivative ($A_{22c1}$) are elaborated to $A_{22a}$ and $A_{22c}$ as shown for case $A_{22b}$ in the above publication. The ethylated intermediate $A_{22c1}$ may be prepared from $A_{22a1}$ by alkylation using e.g.; EtI and a base such as potassium carbonate, cesium carbonate. This reaction may preferentially be carried out in polar solvents such as dimethylformamide, or dimethylacetamide. Mitsunobu reaction of $A_{16}$, gives the compounds containing the phenol ether. Removal of Boc group using e.g., trifluoroacetic acid, in solvents such as dichloromethane, followed by hydrolysis of the ester group as discussed in SCHEME 6 above gives the compounds ($A_{23a}$–$A_{23c}$).

kanoate (A) gives the olefin containing intermediate. This reaction may be carried out in the presence of a base (e.g.; NaH, sodium tert-butoxide and the like) in a solvent such as THF or DMF. The methodology described in e.g.; Synthesis 661–664 (1986) and Synth. Communication 18, 1349–1362

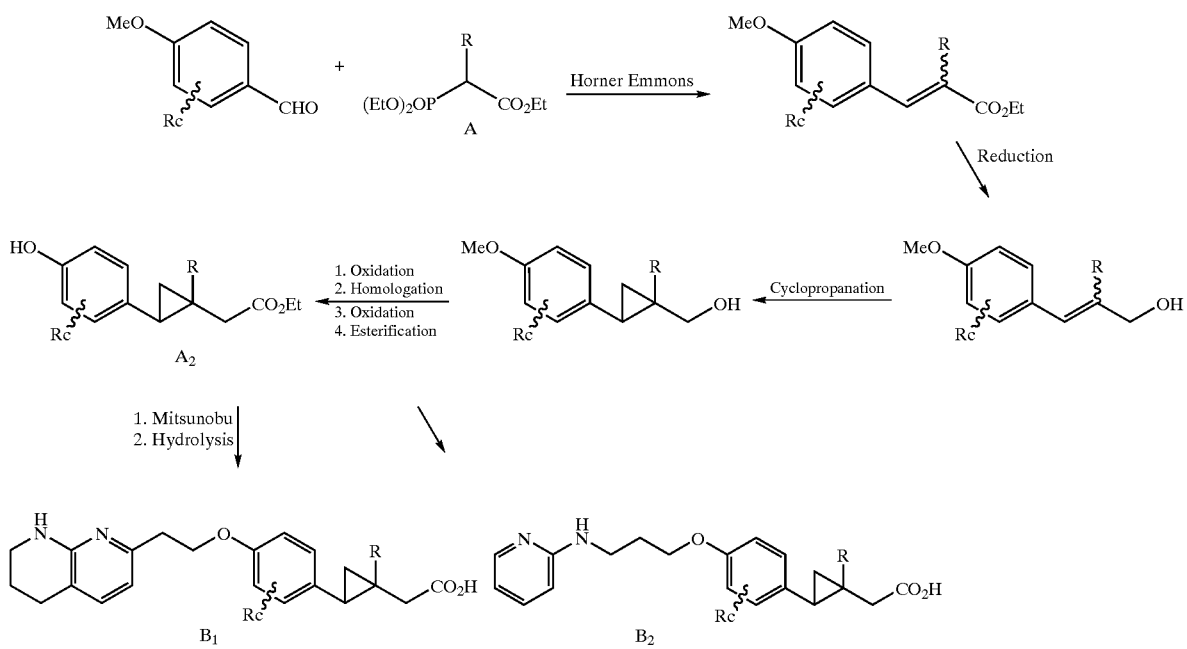

SCHEME 8

SCHEME 8

The cyclopropyl compounds having a substituent at the β-position to the carboxylic acid can be prepared as shown in scheme above. For example, Horner Emmons reaction of 4-substituted benzaldehyde with triethyl phosphonoal- (1988) may be used to synthesize intermediate ($A_2$). The sequence of reactions described in EXAMPLE 1 can be used to accomplish the synthesis of the target compounds ($B_1$ and $B_2$).

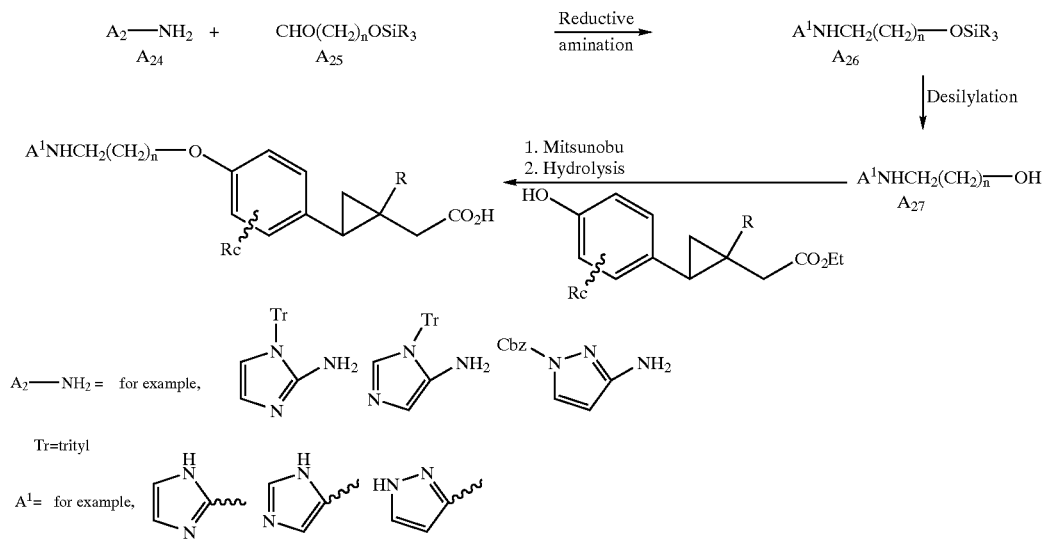

SCHEME 9

SCHEME 9

The target compounds of FORMULA 1 with variations in heteroarylamine $A^1$ can be prepared following the reaction sequence shown in SCHEME 9 above. The reductive amination of arylamine ($A_{24}$) with an aliphatic aidehyde ($A_{25}$) gives the intermediate $A_{26}$ containing the aliphatic chain. This reaction may preferentially be carried out by using sodium triacetoxyborohydride, sodium cyanoborohydride or sodium borohydride as reducing agent and using methyene chloride, ethyl alcohol or tetrahydrofuran as solvent. Commercially accessible heteroarylamine such as 2-amnopyridine could be used directly. In certain cases, protected heteroaryls such as imidazole and pyrazole derived amines may be used as shown above. Desilylation of $A_{26}$ can be accomplished using reagents such as cesium fluoride, potassium fluoride and the like. The generated alcohol $A_{27}$ could be reacted with the substituted phenol as shown in number of examples (for example 4). The trityl, Cbz or other protected groups can easily be removed by methodologies known in literature.

SCHEME 11

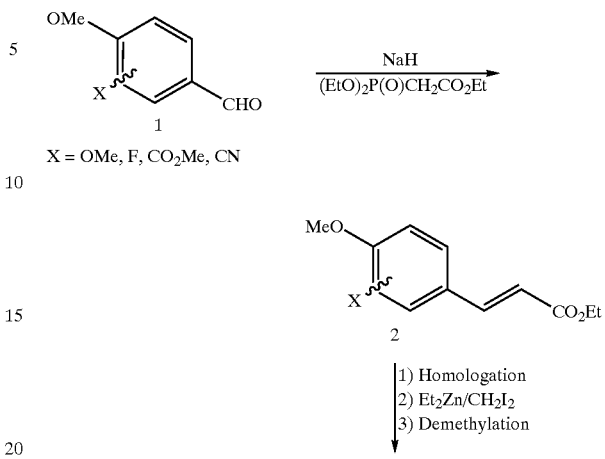

SCHEME 10

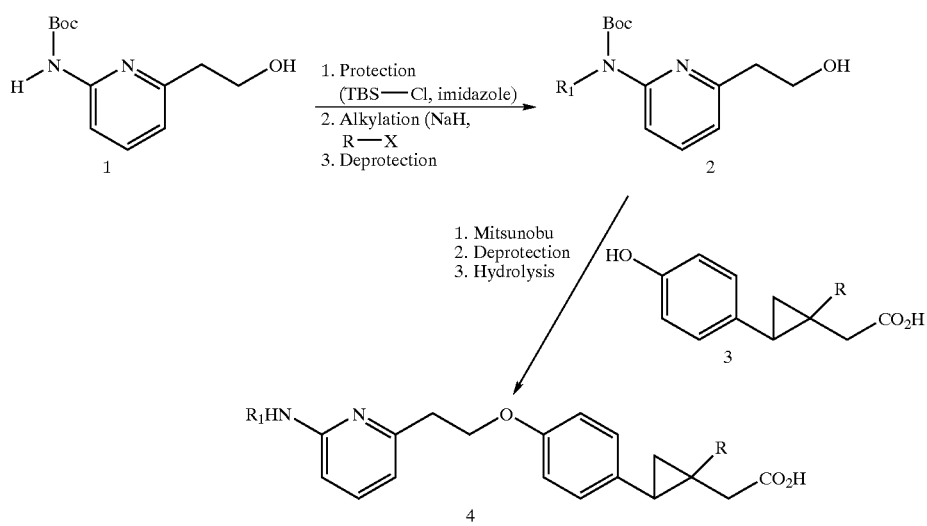

SCHEME 10

Compounds of FORMULA 1 containing 6-aminopyridyl system may be prepared as shown in scheme 10. The intermediate 1 can be prepared as described in J. Med. Chem 43, 22, 2000. The hydroxyl group in 1 can be protected as silyl ether using e.g; ter-butyldimethylsilyl chloride and imidazole. The reaction of generated intermediate with a base such as (sodium hydride in DMF) and the alkyl halide gives the intermediate 2 after deprotection of the silyl ether. Mitsunobu reaction of 2 with phenolic intermediate $A_3$ described in scheme 8 above, gives the compounds containing the phenol ether. Removal of Boc group using e.g., trifluoroacetic acid in solvents such as dichloromethane, followed by hydrolysis of the ester group as discussed in scheme 6 above gives the target compounds 4.

-continued

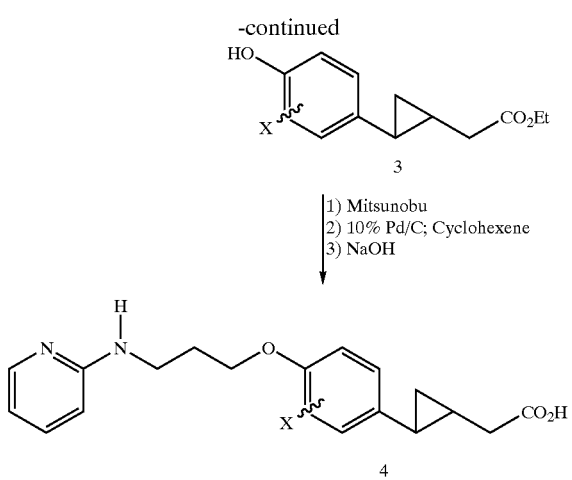

SCHEME 11

The compounds of FORMULA 1 with substituents in phenyl ring A can be synthesized as shown in the above scheme. For example, Horner Emmons reaction of 4-substituted benzaldehyde with triethyl phosphonoacetate gives the olefin containing intermediate. This reaction may be carried out in the presence of a base (e.g.; NaH, sodium tert-butoxide and the like) in a solvent such as THF or DMF. The intermediate can be homologated using the methodology developed by Kowalski and described in J. Am. Chem Soc., 108,1429–30, 1985 and J. Org. Chem 57, 7194, 7208, 1992. The reaction conditions described in Step 3, of EXAMPLE 1 can be used to give the cyclopropyl containing intermediate. Elaboration of this intermediate involving demethylation, Mitsunobu reaction, deoxygenation and hydrolysis of ester gives the target compound. The experimental conditions described in Steps 4–7, of SCHEME 2 can be used to achieve the synthesis of target compound.

Alternately, the cinnamic acid derivative 2 may be elaborated to the cyclopropyl containing intermediate 3 and the target 4 following the methodology shown in example 9.

EXAMPLE A

2-[3-hydroxy-1-propylamino]pyridine-N-oxide

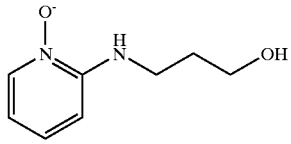

A mixture of 2-chloropyridine-N-oxide (16.6 g, 100 mmoles), 3-amino-1-propanol (15.3 ml, 200 mmoles), $NaHCO_3$ (42 g, 0.5 mole), and tert-amyl alcohol (100 ml) was heated to reflux. After 23 hours, the reaction was cooled, diluted with $CH_2Cl_2$ (300 ml), and filtered to remove insoluble materials. The filtrate was concentrated to afford a brown oil. The oil was dried under vacuum overnight. Ether (100 ml) was added to give a brown solid. The ether was decanted and the solid was washed further with ether/acetonitrile (3/1). The resulting solid was heated at 67° C. under vacuum to give the desired product (13.5 g). $^1H$ NMR was consistent with the proposed structure.

EXAMPLE 1

2-[4-[3-(2-pyridinylamino)propoxy]phenyl] cyclopropaneacetic acid, mono(trifluoracetate)

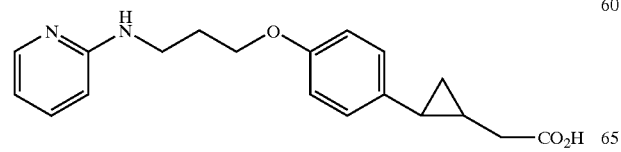

Step 1

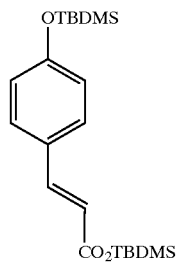

To a solution of trans-4-hydroxy cinnamic acid (16.4 g) and imidazole (20.4 g) in DMF (150 mL) was added a solution of t-butyldimethyl silyl chloride (31.7 g) in DMF (50 mL) in one portion at room temperature. The reaction was stirred for 1 hour and then the solvent was removed in vacuo. The residual oil was partitioned between ether and 5% aqueous citric acid. The organic portion was washed with water, and brine and then dried over $MgSO_4$ and concentrated to afford a colorless oil (41.6 g) which was used without further purification. The $^1H$ NMR was consistent with the proposed structure.

Step 2

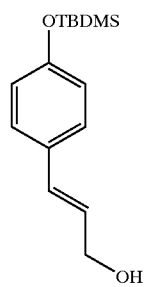

A solution of the product from Step 1 (30.0 g) in ether (250 mL) was placed in a flame dried flask under $N_2$ and chilled to zero degrees. A solution of 250 mL diisobutyl aluminum hydride (200 mL) (1.0 M in THF) was added dropwise over 1 hour and stirring was continued for an additional 1 hour at zero degrees after the addition was completed. The reaction was then carefully quenched with saturated ammonium chloride solution (200 mL) with vigorous stirring. The mixture was stirred for 2 hours, filtered, washed with ether and the layers separated, and the organic portion concentrated. The residual oil was purified in a silica gel column eluting with 25% ethyl acetate/hexane to afford a viscous colorless oil (6.6 g). The $^1H$ NMR was consistent with the proposed structure.

Step 3

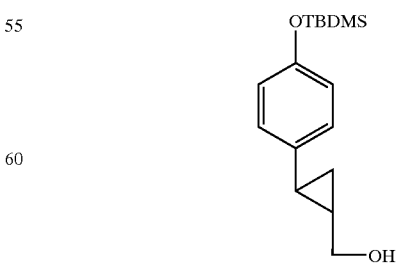

In a flame dried flask under nitrogen was placed a solution of diiodo-methane (2.14 g) and methylene chloride (10 mL).

The solution was chilled to 0° and diethyl zinc (1.0M solution in hexane; 4.0 mL) was added rapidly. The solution was stirred at zero degrees for 15 minutes and then a solution of the product from Step 2 (1.0 g) in 5 mL of methylene chloride was added dropwise. The reaction was stirred for 90 minutes while allowing to warm to room temperature and then quenched with water (5 mL) and partitioned between 0.25N HCl and ethyl acetate. The aqueous portion was extracted with additional solvent and the combined organic extracts were washed with brine, dried over MgSO$_4$, concentrated and the residue purified on a silica gel column eluting with 25% ethyl acetate/hexane to afford a colorless heavy liquid (510 mg). The $^1$H NMR was consistent with the proposed structure.

Step 4

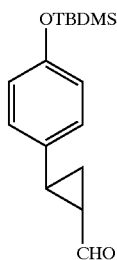

A solution of of oxalyl chloride (1.71 g) in methylene chloride (25 mL) was cooled to −60° C. under nitrogen and a solution of DMSO (2.11 g) in CH$_2$Cl$_2$ (5 mL) was added dropwise and stirring was continued for two minutes. Next, a solution of the product from Step 3 (3.3 g) in CH$_2$Cl$_2$ (5 mL) was added dropwise over 5 minutes and the resultant mixture was stirred for 15 minutes at −60° C. After this period, triethylamine (6.07 g) was added rapidly and the mixture stirred at −60° C. for an additional 5 minutes before being allowed to warm to room temperature. The reaction was diluted with water (50 mL) and extracted several times with methylene chloride. The combined organic extracts were then successively washed with 1% HCl solution, 5% sodium carbonate solution and brine. After drying over MgSO$_4$ and concentrating, the residue was purified on a silica gel column eluting with 25% ethyl acetate/hexane to afford a light yellow liquid (2.85 g). The $^1$H NMR was consistent with the proposed structure.

Step 5

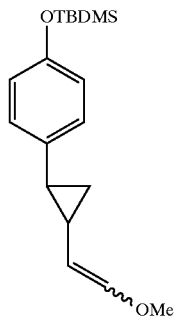

To a suspension of methoxymethyl triphenylphosphonium chloride (5.14 g) in THF (15 mL) was added lithium bis (trimethylsilyl) amide (15 mL, 1.0 M solution in THF) dropwise at zero degrees under nitrogen. After 15 minutes a solution of the product from Step 4 (2.8 g) in THF (20 mL) was added dropwise and stirring continued for 15 minutes. The reaction was then partitioned between ether and water and the layers separated. The aqueous portion was extracted with additional ether and the combined organic extracts were washed with brine, dried over Na$_2$SO$_4$ and concentrated. The residue was purified on a silica gel column eluting with 10% ethyl acetate/hexane to afford a liquid (1.78 g). $^1$H NMR was consistent with the proposed structure.

Step 6

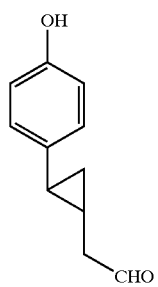

A solution of the product from Step 5 (1.75 g), acetonitrile (45 mL) and 1 N HCl (12 mL) was warmed to 64° C. for 15 hours under nitrogen. The reaction was then cooled and partitioned between ether and saturated sodium bicarbonate solution. The aqueous portion was extracted thoroughly with additional ether and the combined organic extracts were washed with brine, dried over Na$_2$SO$_4$, and concentrated. The residue was purified on a silica gel column eluting with 35% ethyl acetate/hexane to afford a viscous oil (491 mg). $^1$H NMR spectra was consistent with the proposed structure.

Step 7

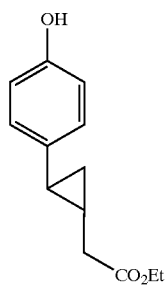

To a suspension of the product from Step 6 (490 mg) in water (5 mL) was successively added a solution of silver nitrate (1.0 g) in water (5 mL) and sodium hydroxide(480 mg) in water (5 mL) at room temperature. The black mixture was stirred for 1 hour and then filtered through a pad of celite. The filtrate was acidified with 1N HCl and extracted with ethyl acetate. The combined organic extracts were dried over Na$_2$SO$_4$ and concentrated to a brown residue which was treated with a 1:1 mixture of ethanol and 4N HCl/dioxane (30 mL) at room temperature for 18 hours. The reaction was concentrated and the residue was purified on a silica gel column eluting with 25% ethyl acetate/hexane to afford a golden oil (226 mg). $^1$H NMR spectra was consistent with the proposed structure.

Step 8

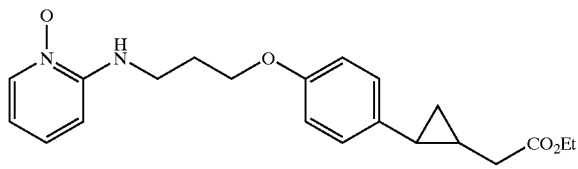

To a solution of the product from Step 7 (220 mg) in DMF (3 mL) under nitrogen was added 2-[3-hydroxy-1-propyl) amino] pyridine-N-oxide (Example A) and triphenylphosphine (315 mg). The solution was stirred at room temperature for several minutes and then a solution of diethyl azodicarboxylate (209 mg) in DMF (2 mL) was added dropwise. The reaction was stirred for 18 hours and the solvent was removed in vacuo. The residue was purified on a silica gel column eluting with 94% $CH_2Cl_{2-5}$% $CH_3OH$-1% $NH_4OH$ to afford a viscous golden oil (125 mg). $^1H$ NMR was consistent with the proposed structure.

Step 9

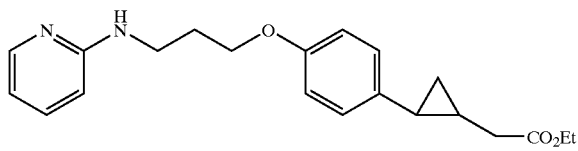

A mixture of the product from Step 8 (120 mg), 10% Pd on carbon (125 mg), cyclohexene (1.0 mL) and isopropanol (10 mL) was refluxed for 3 hours. The reaction mixture was cooled, filtered through a pad of celite and washed with excess isopropanol. The filtrate was concentrated and the residue was purified on a silica gel column eluting with 97% $CH_2Cl_{2-2.5}$% $CH_3OH$ and 0.5% $NH_4OH$ to afford a colorless oil (74 mg). $^1H$ NMR was consistent with the proposed structure.

Step 10

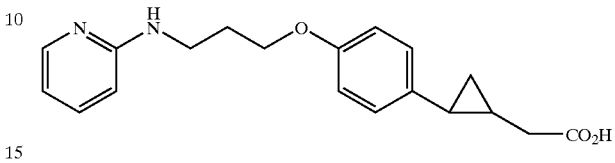

A solution of the product from Step 9 (70 mg) in methanol (5 mL) and 1 N sodium hydroxide (5 mL) was stirred at room temperature for 18 hours. The reaction mixture was quenched with trifluoroacetic acid (1 mL) and concentrated. The residue was purified on a reverse place HPLC using acetonitrile/water (0.5%.TFA) gradient to give the desired product as a viscous oil (36 mg). Elemental analysis: calcd. for $C_{19}H_{22}N_2O_3$.TFA C, 57.27; H, 5.26; N, 6.36; Found: C, 57.99; H, 5.44; N, 6.27; $^1H$ NMR was consistent with the proposed structure.

EXAMPLE 2

2-[4-[3-(2-pyridinylamino)propoxy]phenyl] cyclopentaneacetic Acid

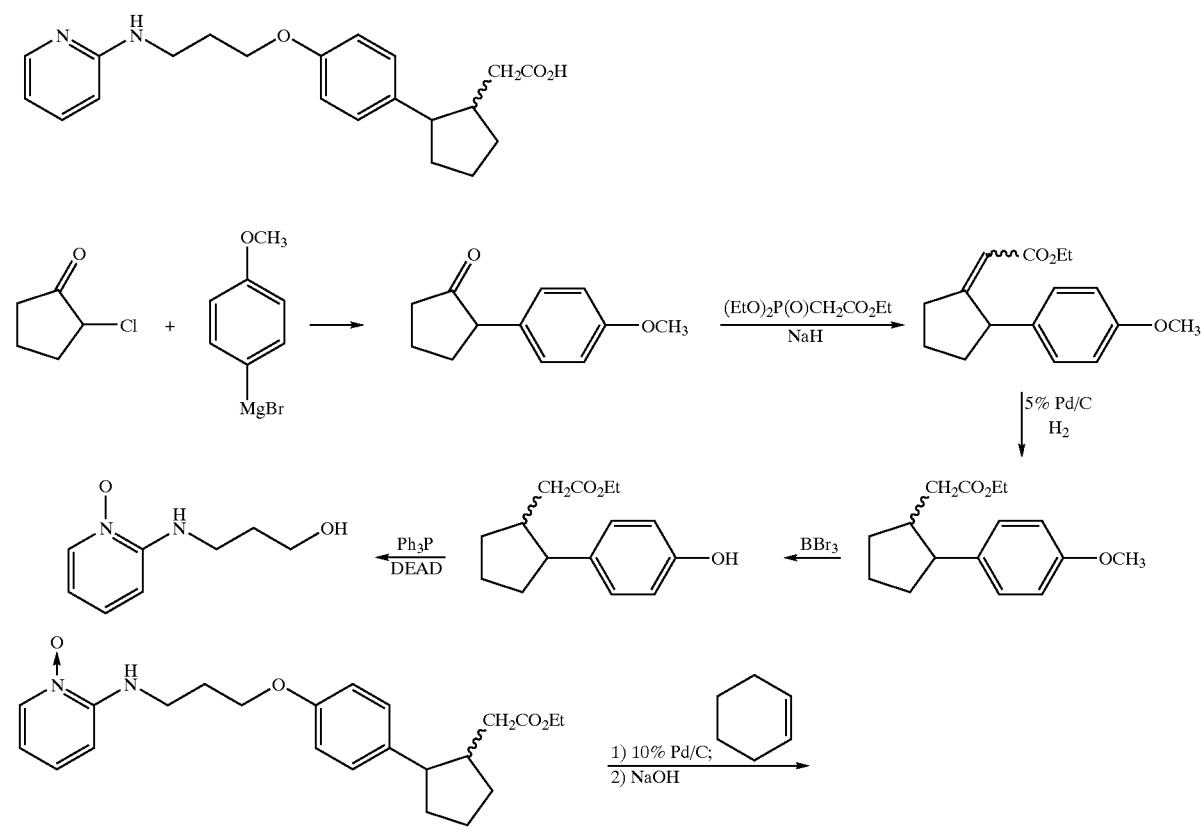

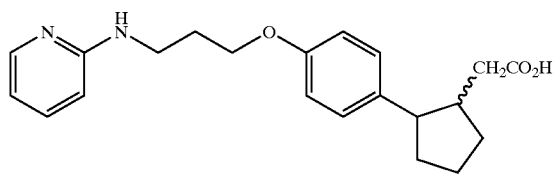

Step 1

In a flame dried flask under $N_2$ was placed a solution of 2-chlorocyclopentanone (10.0 g) in diethyl ether (50 mL). While stirring at room temperature, 4-methoxyphenylmagnesium bromide (170 mL; 0.5 M solution in THF) was added dropwise. An exothermal reaction ensued and stirring was continued for an additional 30 minutes after the addition was completed. The reaction was quenched with 1N HCl (150 mL) and the layers were separated. The aqueous portion was extracted with ethyl acetate and then the combined organic portions were washed with water and brine and then dried ($Na_2SO_4$) and concentrated. The residue was purified on a silica gel column eluting with 25% ethyl acetate/hexane to afford a dark oil (4.1 g). $^1$H NMR was consistent with the proposed structure.

Step 2

In a flame dried flask under $N_2$ was suspended sodium hydride (310 mg, 60% dispersion) in THF (10 mL). A solution of triethylphosphonoacetate (1.74 g) in THF (5 mL) was added dropwise and the reaction was allowed to stir at room temperature for 30 minutes. A solution of the product from Step 1 (1.0 g) in THF (5 mL) was added in one portion and the reaction brought to reflux for 1 hour. The reaction was cooled and partitioned between 1 N HCl and ethyl acetate. The aqueous portion was extracted with additional ethyl acetate and the combined organic extracts were washed with water, brine, dried ($Na_2SO_4$), and concentrated. The residue was purified on a silica gel column eluting with 20% ethyl acetate/hexane to afford a liquid (800 mg). $^1$H NMR was consistent with the proposed structure.

Step 3

A solution of the product from Step 2 (800 mg) in ethanol was shaken in a Parr hydrogenation apparatus with 5% Pd/C under 60 psi hydrogen pressure at room temperature for 3 hours. The reaction mixture was then filtered and concentrated and the residual oil (691 mg) was used without further purification in the next step. $^1$H NMR was consistent with the proposed structure.

Step 4

To a solution of the product from Step 3 (2.70 g) in methylene chloride (15 mL) was added boron tribromide (25 mL, 1.0 M solution in $CH_2Cl_2$) over 10 minutes at room temperature. After stirring at room temperature for 1 hour, the reaction was quenched with ethanol and then concentrated. The residue was partitioned between ethyl acetate and 10% sodium bicarbonate solution. The aqueous portion was extracted with additional solvent and the combined organic solvents were washed with brine, dried over $Na_2SO_4$, concentrated, and the residue purified on a silica gel column eluting with 25% ethyl acetate/hexane to afford a golden oil (1.74 g). $^1$H NMR was consistent with the proposed structure.

Step 5

The title compound produced in Step 5 was prepared from the product described in Step 4 (1.60 g) using the same procedure as described in Step 8 of Example 1. The crude product was purified on a silica gel column eluting with 95% $CH_2Cl_2$–4% $CH_3OH$–1%$NH_4OH$ to afford a golden oil (2.08 g). $^1$H NMR was consistent with the proposed structure.

Step 6

The compound produced in Step 6 was prepared from the product described in Step 5 (2.0 g) using the same procedure as described in Step 9 of Example 1. The crude product was purified on a silica gel column eluting with 97% $CH_2Cl_2$–2% $CH_3OH$–1% $NH_4OH$ to afford a viscous oil (1.2 g). $^1$H NMR was consistent with the proposed structure.

Step 7

The title compound was prepared from the product described in Step 6 (500 mg) using the same procedure as described in Step 10 of Example 1. The crude product was purified in similar fashion to afford a viscous colorless glass (272 mg). Elemental analysis: Calculated for $C_{21}H_{26}N_2O_3 \cdot 1.5$ TFA $\cdot 0.25H_2O$: C, 54.39; H, 5.33; N, 5.29; Found: C, 54.35; H, 5.46; N, 5.31. $^1$H-NMR was consistent with the proposed structure.

EXAMPLE 3

3-[4-[3-(2-pyridinylamino)propoxy]phenyl]cyclopentaneacetic Acid

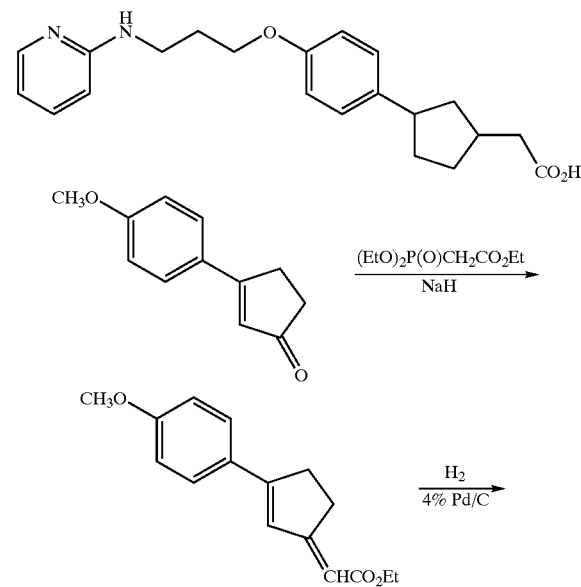

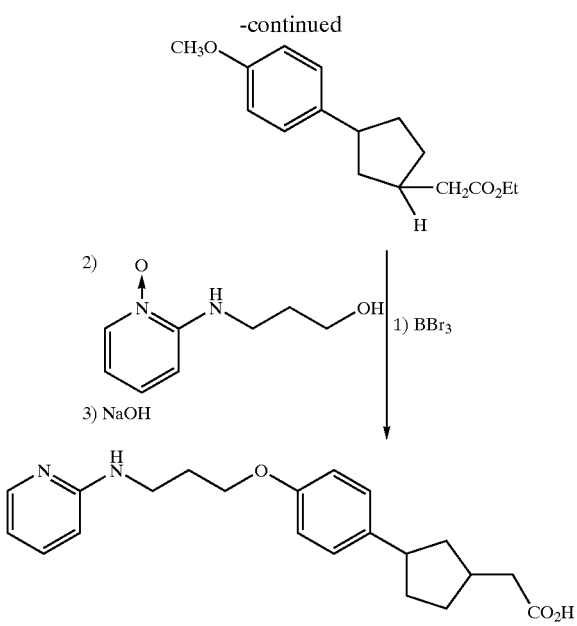

Step 1
The starting material was prepared according to the procedure of Wilds and Johnson, J.A.C.S., 67,286–290, 1945. The compound was prepared from 3-(4-methoxyphenyl) cyclopentenone (2.5 g) using the same procedure as described in Step 2 of Example 2. The crude product was purified on a silica gel column eluting with 30% ethyl acetate/hexane to afford an orange solid (1.53 g). $^1$H NMR was consistent with the proposed structure.

Step 2
A solution of the product from Step 1 (1.5 g) in ethanol was shaken in a Parr hydrogenation apparatus with 4% Pd/C under 5 psi hydrogen pressure at room temperature for 8 hours. The reaction mixture was filtered and concentrated and the crude product was purified on a silica gel column eluting with 25% ethyl acetate/hexane to afford a liquid (1.35 g). $^1$H NMR was consistent with the proposed structure.

Step 3
The compound produced in Step 3 was prepared from the product described in Step 2 (1.3 g) using the same procedure described in Step 4 of Example 2. The crude product was purified on a silica gel column eluting with 30% ethyl acetate/Hexane to afford a liquid (1.22 g). $^1$H NMR was consistent with the proposed structure.

Step 4
The compound produced in Step 4 was prepared from the product described in Step 3 (600 mg) using the same procedure described in Step 8 of Example 1. The crude product was purified on a silica gel column eluting with 96.5% $CH_2Cl_2$–3.0% $CH_3OH$–0.5% $NH_4OH$ to afford a golden oil (606 mg). $^1$H NMR was consistent with the proposed structure.

Step 5
The compound produced in Step 5 was prepared from the product described in Step 4 (595 mg) using the same procedure described in Step 9 of Example 1. The crude product was purified on a silica gel column eluting with 97.5% $CH_2Cl_2$–2.0% $CH_3OH$–0.5% $NH_4OH$ to afford a semi solid (320 mg). $^1$H NMR was consistent with the proposed structure.

Step 6
The title compound was prepared from the product described in Step 5 (310 mg) using the same procedure described in Step 10 of Example 1. The crude product was purified in similar fashion to afford a white solid (191 mg). Analysis: Calculated for $C_{21}H_{26}N_2O_3$·1.0 TFA: C, 58.97; H, 5.81; N, 5.98; Found: C, 58.70; H, 5.81: N, 5.92. $^1$H NMR was consistent with the proposed structure.

EXAMPLE 4

2,2-difluoro-3-[4-[3-(2-pyridinylamino)propoxy]phenyl]cyclopropaneacetic Acid

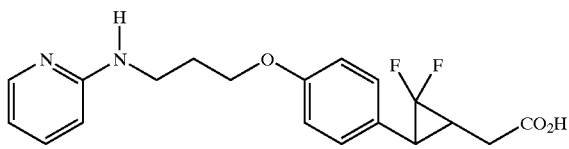

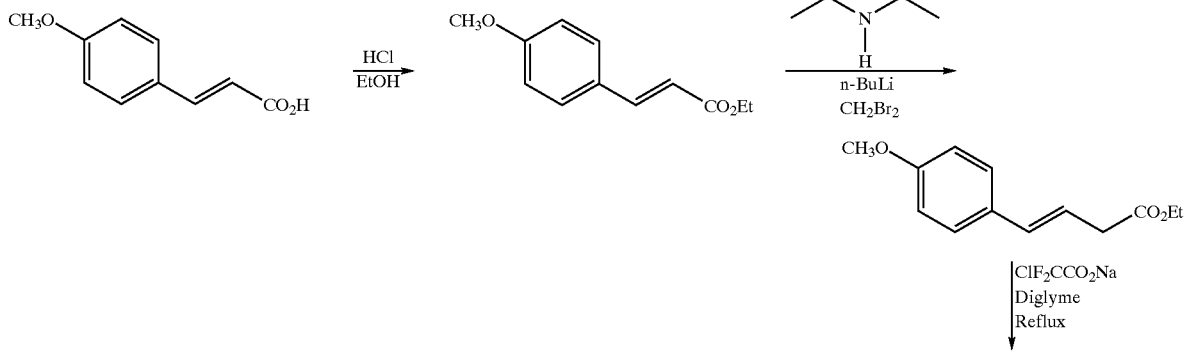

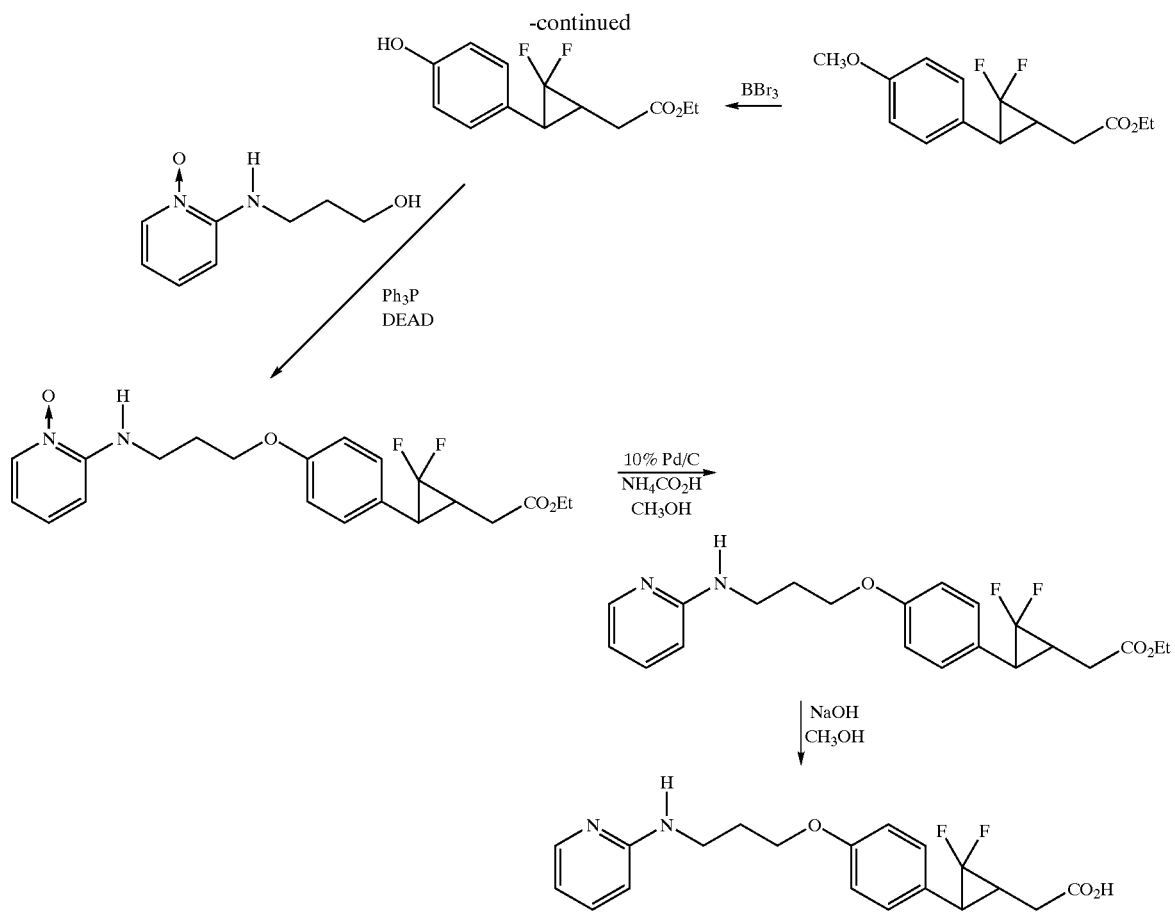

Step 1

A solution of 4-methoxy trans cinnamic acid (20 g) in absolute ethanol (300 ml) and 4N HCl/dioxane (100 ml) was stirred at room temperature for 16 hours. The solution was concentrated and the residue was purified on a silica gel column eluting with 25% ethyl acetate/hexane to afford a low melting solid (17.5 g) which solidified to a glass upon standing at room temperature. The $^1$H NMR was consistent with the proposed structure.

Step 2

In a flame dried flask under nitrogen was placed a solution of 2,2,6,6-tetramethylpiperidine (24.66 g) in THF (150 ml) and chilled to 00. A solution of n-BuLi (2.5 M in hexane; 64 ml) was added dropwise over 10 minutes and stirring was continued for an additional 15 minutes after the addition was completed. This solution was then added dropwise to a solution of dibromomethane (27.8 g) in THF (150 ml) in another flame dried flask under nitrogen at −700. After 5 minutes a solution of the ester (10.0 g) from Step 1 in THF (50 ml) was added dropwise over 5 minutes and 10 minutes later additional 2,2,6,6-tetramethylpiperidine (6.85 g) was added followed by n-BuLi (2.5 M in hexane; 155 ml) dropwise. The cooling bath was then replaced by a water bath at room temperature and after the reaction was stirred for 15 minutes it was poured into an ice cold acidic ethanol solution (prepared from 125 ml of acetyl chloride in 625 ml of ethanol). The mixture was then extracted several times with ether and the combined extracts were washed with 10% sulfuric acid, 5% sodium bicarbonate solution, brine and dried ($Na_2SO_4$). The filtered solution was concentrated and the residue was purified on a silica gel column eluting with 20% ethyl acetate/hexane to afford a dark red oil (2.46 g). The $^1$H NMR was consistent with the proposed structure.

Step 3

A mixture of the ester (2.4 g) from Step 2, sodium chlorodifluoroacetate (10.7 g) and diglyme (90 ml) was refluxed under $N_2$ for 16 hours. The reaction was cooled and partitioned between ethyl acetate and water. The aqueous portion was extracted with additional ethyl acetate and the combined organic extracts were washed with water, brine, and dried ($Na_2SO_4$). The filtered solution was concentrated and the residue was purified on a silica gel column eluting with 20% ethyl acetate/hexane to afford a golden oil (1.23 g). The $^1$H NMR was consistent with the proposed structure.

Step 4

A solution of the ester (1.2 g) from Step 3 in methylene chloride (25 ml) was chilled to 0° under $N_2$ and treated dropwise with boron tribromide (1.0 M in methylene chloride; 10 ml). The reaction was stirred for 30 minutes while allowing to warm to room temperature. The reaction was then carefully quenched with ethanol (10 ml), stirred for 15 minutes and concentrated. The reaction was partitioned between ethyl acetate and 10% sodium bicarbonate solution. The aqueous portion was extracted with additional ethyl acetate and the combined organic extracts were washed with brine and dried ($Na_2SO_4$). The filtered solution was concentrated and the residue was purified on a silica gel column eluting with 30% ethyl acetate/hexane to afford a light yellow solid (863 mg). The $^1$H NMR was consistent with the proposed structure.

Step 5

To a solution of the product from Step 4 (1.0 g) in THF (25 ml) under nitrogen was added 2-[(3-hydroxy-1-propyl)

amino] pyridine-N-oxide (841 mg) and triphenylphosphine (1.31 g). The solution was stirred at room temperature for several minutes and then a solution of diethylazodicarboxylate (871 mg) in THF (15 ml) was added dropwise. The reaction was stirred for 18 hours and the solvent was removed in vacuo. The residue was purified on a silica gel column eluting with 97% $CH_2Cl_{2-2.5}$% $CH_3OH$-0.5% $NH_4OH$ to afford a golden oil (1.02 g). The $^1H$ NMR was consistent with the proposed structure.

product as a viscous oil (80 mg). The $^1H$ NMR was consistent with the proposed structure. Elemental analysis: calculated for $C_{19}H_{20}N_2F_2O_3 \cdot TFA$: C, 52.95; H, 4.44; N, 5.88; Found: C, 52.39; H, 4.60; N, 5.62.

EXAMPLE 5

(2-{4-[2-(5,6,7,8-Tetrahydro-[1,8]naphthyridin-2-yl)-ethoxy]-phenyl}-cyclopropyl)-acetic Acid

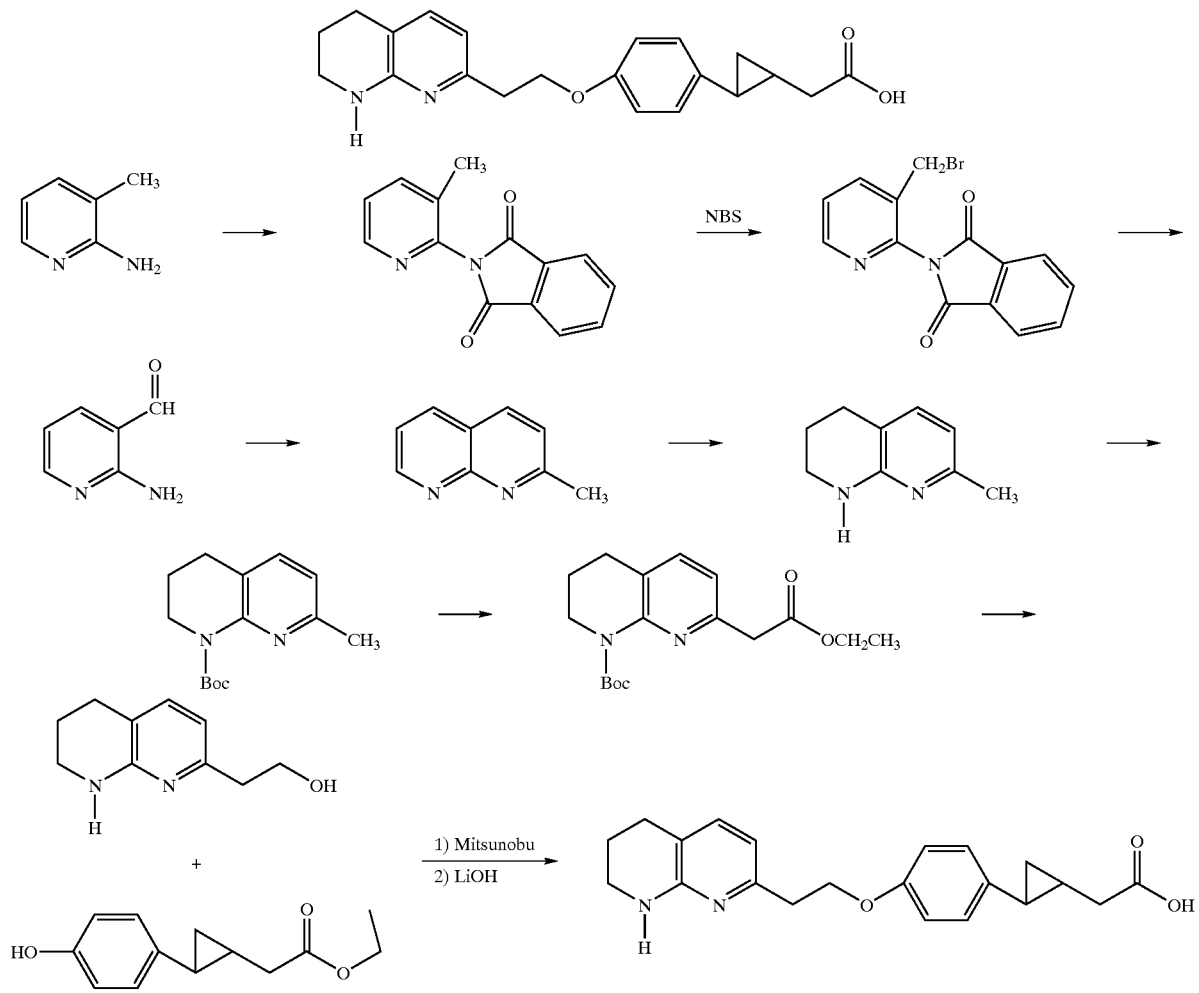

Step 6

A mixture of the product of Step 5 (500 mg), 10% Pd on carbon (128 mg), ammonium formate (543 mg) and methanol (10 ml) was stirred at room temperature for 20 hours. The reaction mixture was concentrated and the residue was purified on a silica gel column eluting with 97.5% $CH_2Cl_{2-2}$% $CH_3OH$-0.5% $NH_4OH$ to afford a viscous oil (189 mg). The $^1H$ NMR was consistent with the proposed structure.

Step 7

A solution of the product from Step 6 (180 mg) in methanol (5 ml) and 1N sodium hydroxide (5 ml) was stirred at room temperature for 6 hours. The reaction was quenched with trifluoroacetic acid (2 ml) and concentrated. The residue was purified on a reverse phase HPLC using acetonitrile/water (0.5% TFA) gradient to give the desired Step 1

2-(3-methyl-2-pyridinyl)1H-isoindole-1,3 (2H)-dione

To a neat 2-amino-3-picoline (91 g, 0.84 mol) was added phthalicanhydrous (125 g, 0.84 mol), the resulting solid mixture was heated at 120° C. and water was distilled off from the reaction mixture. The reaction mixture was cooled to room temperature and solid was dissolved in methylenechloride (1 L). The organic solution was washed with water (2×500 ml), brine (1×500 ml), dried over $MgSO_4$. The color solution was treated with activated carbon, filtered and filtrate was concentrated under reduced pressure. Ether (300 ml) was added to the concentrated residue and stirred at room temperature overnight. Solid was filtered and washed with ether, dried to give 176 g (88%) white solid. NMR (DMSO) δ 2.17 (m, 3H), 7.46–7.49 (m, 1H), 7.88–8.01 (m, 5H), 8.44–8.46 (m, 1H). Mass spectrometry: 239.19 $(M+H)^+$.

Step 2
2-[3-(dibromomethyl)-2-pyridinyl]-1H-isoindole-1,3(2H)-dione

To a suspension solution of 2-(3-methyl-2-pyridinyl)1H-isoindole-1,3 (2H)-dione (14.6 g, 61 mmol) and NBS (25 g, 140 mmol) in $CCl_4$ (160 mL) was added AIBN (0.1 g), the reaction mixture was refluxed and a irradiated with a sun lamp. AIBN (0.1 g) were added every 30 minutes until the starting material was all consumed. The mixture was cooled to room temperature and solid was filtered. Solid was taken up to methylenechlorid (400 ml) and washed with 5% $Na_2S_2O_3$ (3×150 ml), water (1×150 ml) and dried over $Na_2SO_4$. The solvent was removed under reduced pressure. The concentrated solid was suspended in ether. Solid was filtered and dried to give 20.5 g (84.5%) yellow solid. NMR (DMSO) δ 7.6 (s, 1H), 7.74–7.78(m, 1H), 7.92–8.01 (m, 4H), 8.51–8.55 (m, 1H), 8.63–8.64 (m, 1H). Mass spectrometry: 396.92 $(M+H)^+$.

Step 3
2-amino-3-pyridinecarboxaldehyde

The compound was prepared according to the procedure as described by A. E. Moormann et al, Synthetic Communications, 17(14), 1695–1699 (1987) To a solution of 2-[3-(dibromomethyl)-2-pyridinyl]-1H-isoindole-1,3 (2H)-dione (20 g, 50 mmol) in ethanol (250 ml) was added conc. $NH_4OH$ (25 ml) at 4° C. The reaction mixture was stirred 10 minutes at 4° C. then stirred at room temperature for one hour. Reaction mixture was concentrated under reduced pressure. To the concentrated residue was added con. HCl (150 ml) and mixture was refluxed for 3 hours. The reaction mixture was cooled to room temperature and concentrated. To the concentrated residue was added water (25 ml) then added saturated $K_2CO_3$ to neutralize the solution. The solution was extracted with methylenechloride (3×150 ml). Combined organic solution was washed with water (3×150 ml), brine (1×200 ml), dried over $Na_2SO_4$, concentrated. The concentrated residue was suspended in ether, filtered and washed with ether to give 4.3 g (70%) yellow solid. NMR (DMSO) δ 6.69–6.73 (m, 1H), 7.51 (bs, 2H), 7.95–7.98(m, 1H), 8.20–8.22 (m, 1H), 9.82 (s, 1H).

Step 4
2-methyl-1,8-naphthyridine

The compound was prepared according to the procedure as described by E. M. Hawes and D. G. Wibberley, J. Chem. Soc. (C), 1966, 315. To a solution of 2-amino-3-pyridinecarboxaldehyde (2 g, 16 mmol) in ethanol 3 ml) was added acetone (1.9 g, 32 mmol) and peperidine (0,34 g, 4 mmol) and the reaction mixture was refluxed 24 hours. Reaction mixture was cooled to room temperature then concentrated in vacuum. Ether was added to concentrated residue. Solid was filtered and dried to give 1.62 g (69%) yellow solid. NMR ($CD_3OD$) δ 2.76 (s, 3H), 7.52–7.58 (m, 2H), 8.30 (d, 2H, J=8.33 Hz), 8.36–8.39 (m, 1H), 8.39–8.99 (m, 1H).

Step 5
2-methyl-5,6,7,8-tetrahydro-1,8-naphthyridine

The compound was prepared according to the procedure as described in WO 0033838. To a solution of 2-methyl-1,8-naphthyridine (2 g, 13.9 mmol) in ethanol (35 ml) was added 10% Pd/C, and the reaction mixture was stirred under $H_2$ (10 psi) for 24 hours. Palladium was filtered out through celite and washed with excess ethanol. The filtrate was concentrated under vacuum to give 1.7 g (83%) pink solid. NMR ($CD_3OD$) δ 1.82–1.87 (m, 2H), 2.22 (s, 3H), 2.65–2.76 (m, 2H), 3.33–3.36 (m, 2H), 6.32 (d, 1H, J=7.25 Hz), 7.07 (d, 1H, J=7.38 Hz). Mass spectrometry: 149.15 $(M+H)^+$.

Step 6
2-methyl-8-(tert-butoxycarbonyl)-5,6,7,8-tetrahydro-1,8-naphthyridine

The compound was prepared according to the procedure as described in WO 0033838. To a solution of 2-methyl-5,6,7,8-tetrahydro-1,8-naphthyridine (1 g, 6.7 mmol) in methylenechloride (10 ml) was added di-tert-butyl dicarbonate (3 g, 13 mmol), triethylamine (0.68 g, 6.7 mmol) and 4-DMAP (50 mg), the reaction mixture was refluxed overnight. The reaction mixture was concentrated under vacuum. The concentrated residue was purified on silica gel (1% methanol in methylenechloride) to give 1.1 g (69%) orange solid. NMR ($CD_3OD$) δ 1.50 (s, 9H),1.88–1.95 (m, 2H), 2.43 (s, 3H), 2.73–2.78 (m, 2H), 3.29–3.31 (m, 2H), 3.72–3.76 (m, 2H), 6.95 (d, 1H, J=7.76 Hz), 7.44 (d, 1H, J=7.76 Hz).

Step 7
Ethyl [8-(tert-butoxycarbonyl)-5,6,7,8-tetrahydro-1,8-naphthyridin-2-yl]acetate The compound was prepared according to the procedure as described in WO 0033838. To a solution of 2-methyl-8-(tert-butoxycarbonyl)-5,6,7,8-tetrahydro-1,8-naphthyridine (1.4 g, 5.6 mmol) and diethylcarbonate (2.5 g, 20 mmol) in THF (10 ml) was added LDA (8 ml of 2M solution in hexane) at −78° C. and stirred at −78° C. for 40 minutes. The reaction was quenched with saturated $NH_4Cl$ and extracted with ethylacetate (2×100 ml). Combined organic solution was concentrated and purified on silica gel column to give 1.5 g (83%) yellow oil. NMR ($CD_3OD$) δ 1.25 (t, 3H, J=7.10 Hz), 1.51 (s, 9H), 1.88–1.97 (m, 2H), 2.75 (t, 2H, J=6.59 Hz), 3.74–3.80 (m, 4H), 4.10–4.20 (m, 2H), 7.0 (d, 1H, J=7.61 Hz), 7.39 (d, 1H, J=7.47 Hz).

Step 8
2-(5,6,7,8-tetrahydro-1,8-naphthyridin-2-yl)-1-ethanol

The compound was prepared according to the procedure as described in WO 0033838. To a solution of ethyl [8-(tert-butoxycarbonyl)-5,6,7,8-tetrahydro-1,8-naphthyridin-2-yl]acetate (3.8 g, 11.8 mmol) in THF (20 ml) was added $LiBH_4$ (7.6 ml of 2M solution in hexane, 15.2 mmol), the reaction was refluxed overnight. The reaction mixture was cooled in ice bath and quenched with water. The mixture was extracted with ethylacetate (3×50 ml). The combined organic solution was dried over $MgSO_4$, concentrated and dried under vacuum to give 2.9 g oil. The oil was taken up in methylenechloride (10 ml) and 4N HCl in dioxane (10 ml) was added. The solution was stirred 4 hours at room temperature then concentrated under vacuum. To the concentrated residue was added 1:1/1N NaOH:brine (50 ml) and extracted with methylenechloride (3×80 ml). The combine organic solution was concentrated and purified on silica gel to give 1 g (47%) oil. NMR ($CD_3OD$) δ 1.82–1.88 (m, 2H), 2.66–2.71 (m, 4H), 3.45 (t, 2H, J=5.57 Hz), 3.77 (t, 2H, J=6.84 Hz), 6.36 (d, 1H, J=7.38 Hz), 7.10 (d, 1H, J=7.38 Hz).

Step 9

To a solution of 2-(5,6,7,8-tetrahydro-1,8-naphthyridin-2-yl)-1-ethanol (WO 00/33838; 0.18 g, 1 mmole) and PPh3 (0.26 g, 1 mmole) in dry THF (4 mL) was added cyclopropyl phenol (0.1 g, 0.45 mmole) in dry THF (3 mL) and diisopropyl azodicarboxylate (0.17 g, 1 mmole). The reaction mixture was stirred at room temperature. After 18 hours, the mixture was concentrated under reduced pressure and purified on reverse phase HPLC. The ethyl ester of title compound (0.1 g, 45%) was dissolved in 3 mL 50% acetonitrile in water and LiOH (40 mg) was added. The reaction mixture was heated at 50° C. for one hour then acidified by adding TFA. The residue was purified on reverse phase HPLC to give the title compound (50 mg, 53%) as TFA salt: HRMS:

(MH+)=353.1876. NMR (400 MHz, CD$_3$OD) δ 0.76–0.84 (??m, 1H), 0.85–0.88 (m, 1H), 1.20–1.24 (m, 1H), 1.68–1.71 (m, 1H), 1.90–1.96 (m, 2H), 2.28–2.40 (m, 2H), 2.80 (t, 2H, J=6.24 Hz), 3.10 (t, 2H, J=5.98 Hz), 3.48 (t, 2H, J=5.71 Hz), 4.22 (t, 2H, J=5.97 Hz), 6.70 (d, 1H, J=7.38 Hz), 6.76–6.79 (m, 2H), 6.98–7.01 (m, 2H), 7.57 (d, 1H, J=7.38 Hz).

EXAMPLE 6

2-[3-methyl-4-[3-(2-pyridinylamino)propoxy]phenyl]cyclopropaneacetic Acid

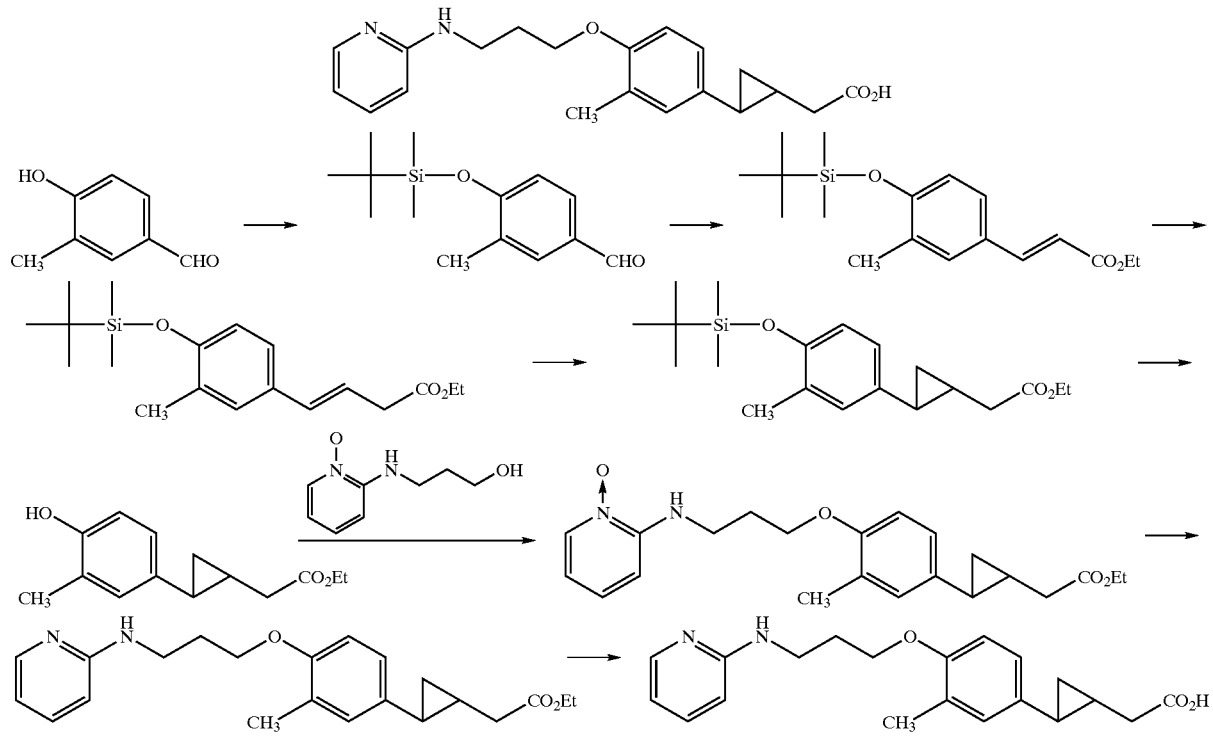

Step 1

4-hydroxy-3-methylbenzaldehyde (3.0 g, 22 mmol) was dissolved in DMF (25 ml). Imidazole (2.72 g, 40 ml) and dimethyl-t-butylsilyl chloride (3.76 g, 25 mmol) were added. After 30 min, the product was extracted with ethyl acetate, and washed with H$_2$O. The aqueous layer was extracted with additional ethyl acetate. The combined organic layer was washed with H$_2$O, brine, and dried. The crude product was purified by vacuum distillation to afford a clean oil in 4.1 g. NMR spectra of the product were consistent for the proposed structure.

Step 2

Under N$_2$, a solution of triethyl phosphonoacetate (4.5 g, 20 mmol) in 40 ml THF was added to a suspension of sodium hydride (0.8 g, 20 mmol, 60% dispersion in mineral oil) in 40 ml THF at 0° C. The resulting mixture was stirred at 0° C. for 30 min. A solution of the product of step 1 (4.1 g, 16.4 mmol) in 20 ml THF was added. The reaction was allowed to warm to room temperature and then was stirred at reflux for 1 h. The cooled reaction was quenched with 1N HCl solution. The product was extracted with ethyl acetate. The aqueous layer was extracted with additional ethyl acetate. The combined ethyl acetate layer was washed with H$_2$O and brine, dried with Na$_2$SO$_4$, and concentrated. The residue was purified by chromatography (on silica gel, EA/hexane5/95) to give a colorless liquid in 4.5 g. NMR spectra of the product were consistent for the proposed structure.

Step 3

A solution of n-BuLi (12.4 ml, 30.9 mmol, 2.5M in hexane) was added to a solution of 2,2,6,6-tetramethylpiperidine (4.8 g, 33.7 mmol) in 35 ml THF at 0° C. to form LTMP. In a separate flask, a solution of the product of step 2 (4.5 g, 14.04 mmol) and dibromomethane (5.3 g, 30.9 mmol) in 30 ml of THF was cooled to −70° C. After 30 min, LTMP solution was cooled to −70° C., and added to above solution via a cannula over 30 min at −65° C. After 10 min, a solution of lithium bis(trimethyl)silyl amide solution (28 ml, 28 mmol, 1M in THF) was added over 15 min at −70° C. The resulting mixture was allowed to warm to −20° C. and then cooled back to −70° C. A solution of s-BuLi solution (43.2 ml, 56.2 mmol, 1.3 M in cyclohexane) was added at −60° C. over 15 min. The mixture was allowed to warm to room temperature. A solution of n-BuLi (12.4 ml, 28 mmol, 2.5 in hexane) was added to the reaction, and the reaction was stirred at room temperature for 1 h. The reaction was cooled to −70° C. and transferred into an acidic ethanol solution (15 ml acetyl chloride and 75 ml ethanol) at 0° C. via a cannula over 1 h. The resulting mixture was diluted with 280 ml ether and washed with 280 ml 10% HCl solution. The aqueous layer was extracted with ether. The combined organic layer was washed with brine, dried with MgSO$_4$, and concentrated. The residue was purified by chromatography (on silica gel, ethyl acetate/hexane=5/95) to give a brown liquid in 1.65 g. NMR spectra of the product were consistent for the proposed structure.

Step 4

Under N$_2$, a solution of diethyl zinc (5.5 ml, 5.5 mmol, 1.0 M in hexane) was added to a solution of diiodomethane (2.95 g, 11.0 mmol) in 15 ml dichloromethane at 0° C. After 15 min, a solution of the product of step 3 (1.65 g, 4.9 mmol) in 5 ml dichloromethane was added at 0° C. dropwise. The reaction was warmed to 35° C. After 30 min, the reaction was cooled to 0° C. and quenched with $H_2O$. The product was extracted with ethyl acetate and washed with 1N HCl. The aqueous layer was extracted with ethyl acetate. The combine organic layer was washed with $H_2O$, brine, dried with $Na_{0.2}SO_4$, and concentrated to give a brown oil in 1.22 g. This product was used without further purification. NMR spectra of the product were consistent for the proposed structure.

Step 5

Potassium fluoride (0.3 g, 5.1 mmol) was added to a solution of the product of step 4 (1.22 g, 3.5 mmol) in 15 ml DMF and 1.0 ml $H_2O$. The reaction was stirred at room temperature for 18 h. The product was extracted with ethyl acetate. The aqueous layer was extracted with an additional ethyl acetate. The combined organic layer was washed with $H_2O$, brine, dried with $Na_2SO_4$, and concentrated. The residue was purified by chromatography (on silica gel, EA/hexane=3/7) to yield a pale brown oil in 0.373 g. This product was used without further purification. NMR spectra of the product were consistent for the proposed structure.

Step 6

A solution of diethyl azodicarboxylate (0.348 g, 2.0 mmol) in 3 ml THF was added to a solution of the product of step 5 (0.37 g, 1.6 mmol) and triphenylphosphine (0.525 g, 2.0 mmol) in 12 ml THF at room temperature. After 15 min, 2-(3-Hydroxypropylamino)pyridine N-oxide (0.336 g, 2 mmol) was added. The reaction was stirred at room temperature for 18 h and concentrated. The residue was purified by chromatography (on silica gel, $C_2HCl_2/CH_3OH/NH_4OH$=98.5/1/0.5) to yield a pale brown oil in 0.127 g. NMR spectra of the product were consistent for the proposed structure.

Step 7

A solution of the product of step 6 (0.25 g, 0.65 mmol), ammonium formate (0.41 g, 6.5 mmol), and 10% palladium on carbon (0.075 g, 0.07 mmol) in 5 ml methanol was stirred at room temperature for 20 h. Additional ammonium formate (0.41 g, 6.5 mmol) and 10% Palladium on carbon (0.075 g, 0.07 mmol) were added. After 20 h, the reaction was filtered through a short column of Celite® and washed with ethanol. The filtrate was concentrated and residue was purified by chromatography (on silica gel, $C_2HCl_2/CH_3OH/NH_4OH$=98.5/1/0.5) to afford a pale brown oil in 0.127 g). NMR spectra of the product were consistent for the proposed structure.

Step 8

A solution of the product of step 7 (0.095 g, 0.26 mmol) in 5 ml 1 N NaOH and 5 ml methanol was stirred at room temperature for 18 h. The reaction was acidified with 1.5 ml trifluoroacetic acid and concentrated. The residue was purified on HPLC using acetonitrile gradient 10–50% in 30 min to yield 40.3 mg. FAB-MS:(MH+)=341.4. $^1$H NMR ($CDCl_3$) δ 0.81 (dt, 1H), 0.99 (dt, 1H), 1.31 (m, 1H), 1.71 (dt, 1lH), 2.19 (s, 3H), 2.19 (p, 2H), 2.43 (d, 2H), 3.54 (q, 2H), 4.03 (t, 2H), 6.71 (m, 2H), 6.83 (d, 1H), 6.89 (m, 2H), 7.76 (t, 1H), 7.80 (d, 1H), 9.61 (br, 1H). Anal Calcd. for $C_{20}H_{24}N_2O_3$ plus 1.25 $CF_3COOH$: C, 55.96; H, 5.27; N, 5.80. Found: C, 56.05; H, 5.47; N, 5.78.

EXAMPLE 7

2-[2-methoxy-4-[3-(2-pyridinylamino)propoxy]phenyl]cyclopropaneacetic Acid

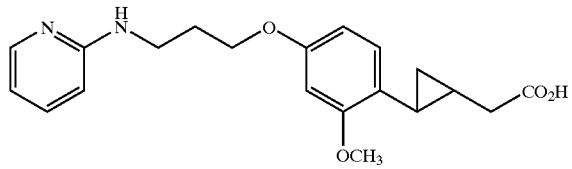

The title compound was prepared according to the general procedures described for the preparation of EXAMPLE 6:H NMR(CDCl3) δ 0.78 (dt, 1H), 0.96 (dt, 1H), 1.19 (m, 1H), 1.86 (dt, 1lH), 2.19 (p, 2H), 2.38 (dd, 1H), 2.56 (dd, 1H), 3.51 (t, 2H), 3.83 (s, 3H), 4.06 (t, 2H), 6.39 (dd, 1H), 6.44 (d, 1H), 6.69 (t, 1H), 6.81 (d, 1H), 6.85 (d, 1H), 7.75 (t, 1H), 7.77 (d, 1H). Anal Calcd. for $C_{20}H_{24}N_2O_4$ plus 0.9 $CF_3COOH$: C, 57.04; H, 5.47; N, 6.10. Found: C, 57.08; H, 5.38; N, 6.21.

EXAMPLE 8

2-[2-methyl-4-[3-(2-pyridinylamino)propoxy]phenyl]cyclopropaneacetic Acid

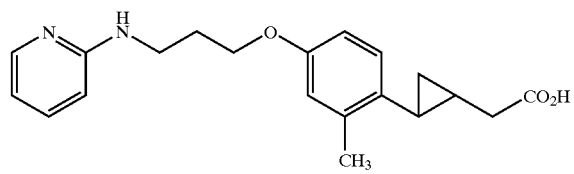

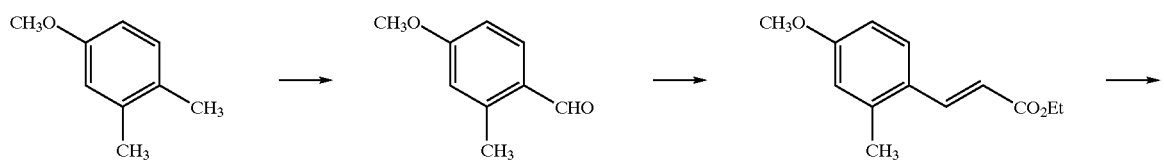

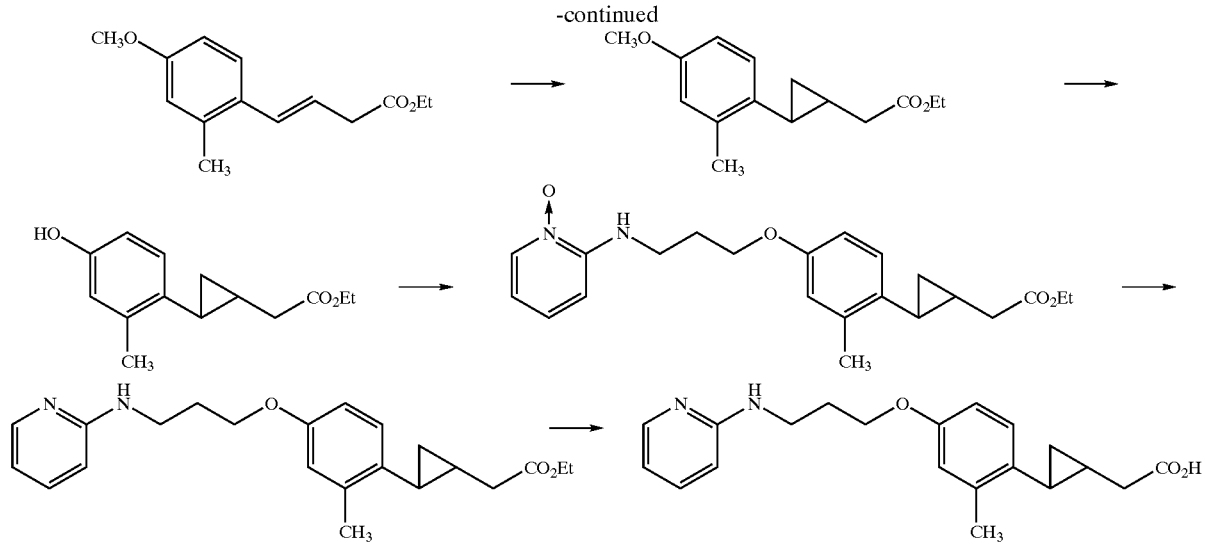

Step 1

3,4-Dimethyl anisole (6.0 g, 44.0 mmol) was dissolved in 200 ml methanol. A solution of ammonium cerium (IV) nitrate in 300 ml methanol was added at room temperature over 5 min and the reaction was stirred for 10 min. The reaction was diluted with 300 ml $H_2O$. The product was extracted with dichloromethane. The organic layer was washed with brine, dried with $Na_2SO_4$, and concentrated. The residue was purified by chromatography (on silica gel, ethyl acetate/hexane=1/9) to afford a greenish liquid in 5.7 g. NMR spectra of the product were consistent for the proposed structure.

Step 2

A solution of triethyl phosphonoacetate (11.2 g, 50 mmol) in 50 ml THF was added to a mixture of sodium hydride (1.2 g, 50 mmol) in 50 ml THF at 0° C. After 30 min, a solution of the product of step 1 (5.7 g, 40 mmol) in 25 ml THF was added at 0° C. The reaction was heated at reflux for 1 h. The reaction was diluted with ethyl acetate, and 1N HCl solution. The aqueous layer was extracted with additional ethyl acetate. The combined organic layer was washed with $H_2O$, brine, dried with $Na_2SO_4$, and concentrated. The residue was purified by chromatography (on silica gel, ethyl acetate/hexane=15/85) to give a colorless liquid in 7.89 g. NMR spectra of the product were consistent for the proposed structure.

Step 3

A solution of n-butyllithium (17.6 ml, 44 mmol, 2.5M in hexane) was added to a solution of 2,2,6,6-tetramethylpiperidine (6.8 g, 48 mmol) in 50 ml THF at 0° C. to form LTMP. In a separate flask, a solution of the product of step 2 (4.4 g, 20 mmol) and dibromomethane (7.6 g, 44 mmol) in 40 ml THF was cooled to −70° C. After 30 min, LTMP solution was cooled to −70° C., and added to above solution via a cannula at −65° C. over 30 min. After 10 min, a solution of lithium bis(trimethyl)silyl amide solution (40 ml, 40 mmol, 1M in THF) was added over 15 min at −70° C. The resulting mixture was allowed to warm to −20° C. and then cooled back to −70° C. A solution of s-butyllithium solution (61.6 ml, 80 mmol, 1.3 M in cyclohexane) was added at −60° C. over 15 min. The mixture was warmed to room temperature. A solution of n-BuLi (17.6 ml, 40 mmol, 2.5 in hexane) was added, and the reaction was stirred at room temperature for 1 h. It was cooled to −70° C. and transferred into an acidic ethanol solution (20 ml acetyl chloride and 100 ml ethanol) at 0° C. via a cannula over 1 h period. The resulting mixture was diluted with 400 ml ether and washed with 400 ml 10% HCl solution. The aqueous layer was extracted with ether. The combined organic layer was washed with brine, dried with $MgSO_4$, and concentrated. The residue was purified by chromatography (on silica gel, ethyl acetate/hexane=1/9) to give a brown liquid in 1.17 g. NMR spectra of the product were consistent for the proposed structure.

Step 4

Under $N_2$, diethyl zinc solution (5.5 ml, 5.5 mmol, 1.0 M in hexane) was added to a solution of diiodomethane (2.95 g, 11 mmol) in 15 ml dichloromethane at 0° C. After 15 min, a solution of the product of step 3 (1.15 g, 4.9 mmol) in 5 ml dichloromethane was added dropwise at 0° C. The reaction was heated at 35° C. for 30 min. The reaction was quenched with $H_2O$ at 0° C. and acidified with 1N HCl. The product was extracted with ethyl acetate. The aqueous layer was extracted with additional ethyl acetate. The combined organic layer was washed with $H_2O$, brine, dried with $Na_2SO_4$, and concentrated to afford a brown oil in 1.42 g. This product was used without further purification. NMR spectra of the product were consistent for the proposed structure.

Step 5

The product of step 4 (1.42 g, 5.7 mmol) was dissolved in 15 ml dichloromethane. Under $N_2$ boron tribromide solution (11 ml, 11 mmol, 1M in dichloromethane) was added to the above solution dropwise at 0° C. The reaction was allowed to warm to room temperature. After 30 min, the reaction was carefully quenched with ethanol. The product was extracted with ethyl acetate and washed with 1N HCl. The organic layer was further washed with 5% $NaHCO_3$ solution, brine, dried with $MgSO_4$, and concentrated. The residue was purified by chromatography (on silica gel, ethyl acetate/hexane=2/8) to give a pale brown oil in 0.175 g. NMR spectra of the product were consistent for the proposed structure.

Step 6 A solution of diethyl azodicarboxylate (174 mg, 1.0 mmol) in 1 ml THF was added to a solution of the product of step 5 (175 mg, 0.75 mmol) and triphenylphosphine (262 mg, 1 mmol) in 5 ml THF at room temperature and stirred for 15 min. 2-(3-Hydroxypropylamino)pyridine N-oxide (168 mg, 1 mmol) was added. The reaction was stirred at room temperature for 18 h and concentrated. The residue was purified by chromatography (on silica gel, $CH_2Cl_2$/$CH_3OH$/$NH_4OH$-98.5/1/0.5) to afford 127 mg pale brown oil. NMR spectra of the product were consistent for the proposed structure.

Calcd. for $C_{20}H_{24}N_2O_3$ plus 1.25 $CF_3COOH$: C, 55.96; H, 5.27; N, 5.80. Found: C, 56.24; H, 5.36; N, 5.95.

EXAMPLE 9

2-[3-fluoro-4-[3-(2-pyridinylamino)propoxy]phenyl] cyclopropaneacetic Acid

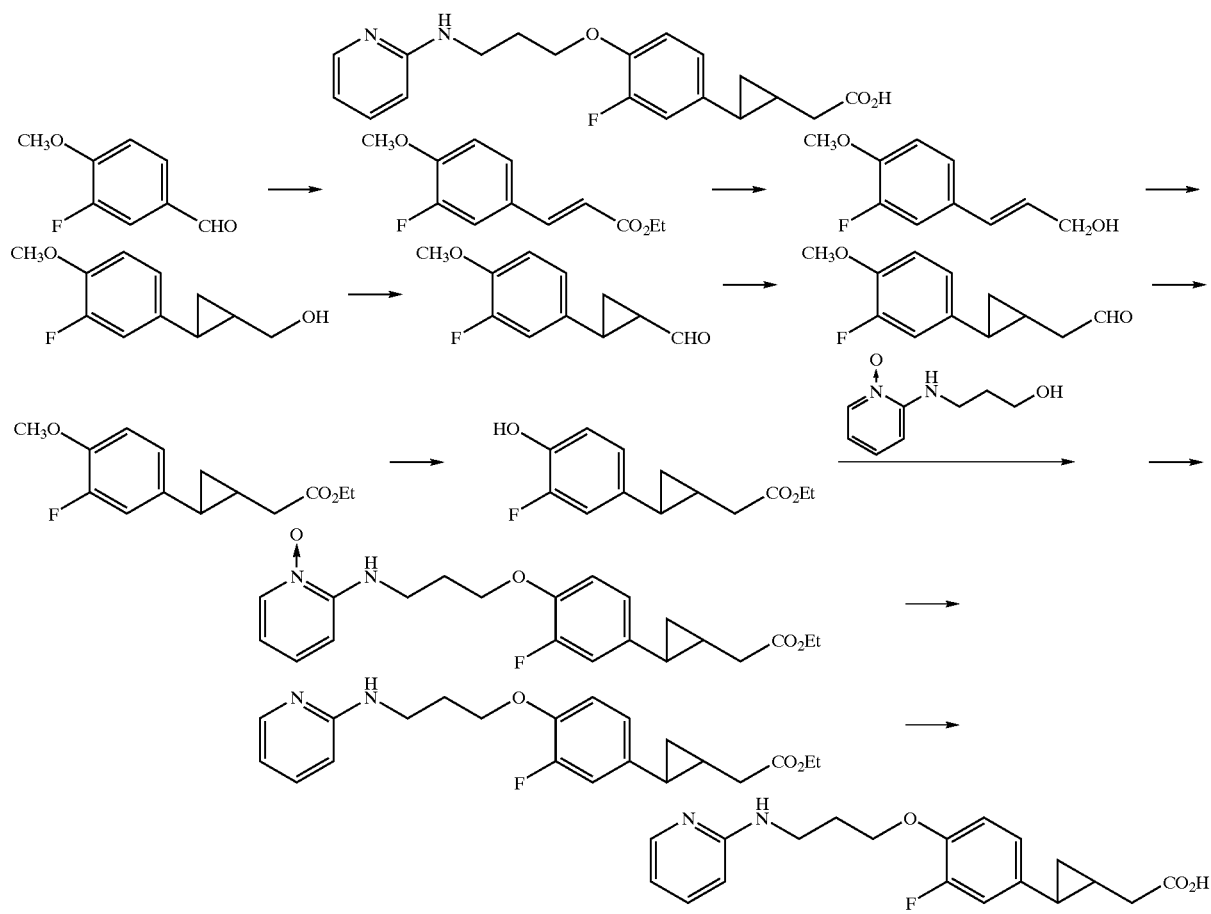

Step 1

A solution of triethyl phosphonoacetate (16.8 g, 75 mmol) in 50 ml THF was added to a mixture of sodium hydride (1.8 g, 75 mmol) in 125 ml THF at 0° C. After 30 min, 3-fluoro-p-anisaldehyde (10.0 g, 64.9 mmol) in 25 ml THF was added at 0° C., and the reaction was stirred at room temperature for 30 min. The reaction was diluted with ethyl acetate, washed with 1N HCl solution. The aqueous layer was extracted with additional ethyl acetate. The combined organic layer was washed with $H_2O$, brine, dried with $Na_2SO_4$, and concentrated. The residue was purified by chromatography (on silica gel, ethyl acetate/hexane=1/4) to give a colorless liquid in 12.9 g. NMR spectra of the product were consistent for the proposed structure.

Step 2 The product of step 1 (8.4 g, 37.5 mmol) was dissolved in 75 ml THF. Under $N_2$ a solution of diisobutylalumium hydride (150 ml, 1 M in THF) was added at 0° C. over 30 min. The reaction was stirred for 30 min and quenched with 250 ml 1N HCl solution. The mixture was stirred for 15 min and filtered through a short column of Celite®. The product was extracted with ethyl acetate. The aqueous layer was extracted with ethyl acetate. The com- Step 7

A mixture of the product of step 6 (127 mg, 0.3 mmol), 10% Pd/C (50 mg, 0.04 mmol), cyclohexene (2.0 ml, 17.8 mmol), and 2-propanol (5.0 ml) was heated at reflux for 4 h. The reaction was allowed to cool to room temperature. Additional 10% Pd/C (50 mg, 0.04 mmol) was added. After 18 h of refluxing, the reaction was cooled to room temperature, filtered through a short column of Celite®, and washed with 100 ml of 2-propanol. The filtrate was concentrated to give 85 mg oil. This product was used without further purification. The NMR spectra were consistent for the proposed structure.

Step 8

The product of step 7 (70 mg, 0.19 mmol) was dissolved in 5 ml methanol and 5 ml 1 N sodium hydroxide solution. The reaction was stirred at room temperature for 5.5 h, acidified with 2 ml trifluoroacetic acid, and concentrated. The residue was purified on HPLC using acetonitrile gradient 10–50% in 30 min to yield 82.7 mg of gummy solid. FAB-MS:(MH+)=341.H NMR(CDCl$_3$) δ 0.82 (m, 1H), 0.89 (m, 1H), 1.31 (m, 1H), 1.70 (dt, 1H), 2.19 (p, 2H), 2.35 (s, 3H), 2.50 (m, 2H), 3.53 (m, 2H), 4.04 (t, 2H), 6.64 (dd, 1H), 6.71 (m, 2H), 6.85 (t, 1H), 6.96 (d, 1H), 7.78 (m, 2H). Anal bined organic layer was dried with $MgSO_4$ and concentrated. The residue was purified by chromatography (on silica gel, ethyl acetate/hexane=2/3) to give a white solid in 3.32 g. NMR spectra of the product were consistent for the proposed structure Step 3

Under $N_2$, diethyl zinc solution (75 ml, 75 mmol, 1.0 M in hexane) was added dropwise to a solution of diiodomethane (40.2 g, 150 mmol) in 200 ml methylene chloride at 0° C. After stirring at 0° C. for 15 min, a solution of the product of step 2 (10.6 g, 58.2 mmol) in 50 ml methylene chloride was added at 0° C. dropwise. The reaction was warmed to 35° C. After 30 min, the reaction was quenched with $H_2O$ at 0° C. and acidified with 1N HCl. The product was extracted with ethyl acetate. The aqueous layer was extracted with additional ethyl acetate. The combined organic layer was washed with $H_2O$, brine, dried with $Na_2SO_4$, and concentrated. The residue was purified by chromatography (on silica gel, ethyl acetate/hexane=2/3) to afford a pale brown oil in 9.6 g. NMR spectra of the product were consistent for the proposed structure.

Step 4

Under $N_2$ DMSO (8.6 g, 110 mmol) in 30 ml methylene cloride was added to a solution of oxalyl chloride (7.0 g, 55.0 mmol) in 30 ml methylene chloride dropwise at $-60°$ C. and stirred for 2 min. A solution of the product of step 3 (9.6 g, 48.9 mmol) in 40 ml methylene cloride was added at $-60°$ C. and the reaction was stirred for 15 min. Triethyl amine (22.8 g, 225 mmol) was added at $-60°$ C. The reaction was stirred for 15 min and allowed to warm to room temperature. The reaction was quenched with 50 ml $H_2O$ and the product was extracted with methylene chloride. The organic layer was washed with 1% HCl, 5% $Na_2CO_3$, brine, dried with $Na_{0.2}SO_4$, and concentrated. The residue was purified by chromatography (on silica gel, ethyl acetate/hexane=3/7) to afford a white solid in 7.32 g. NMR spectra of the product were consistent for the proposed structure.

Step 5

Under $N_2$ atmosphere, lithium bis(trimethylsilyl) amide solution (50 ml, 1.0M in THF) was added to a mixture of methoxy methyltriphenyl phosphonium chloride (17.1 g, 37.6 mmol) in 90 ml THF dropwise at 0° C. After 15 min, it was added to a solution of the product of step 4 (7.3 g, 37.6 mmol) in 60 ml THF at 0° C. The reaction was stirred for 5 min and quenched with $H_2O$. The product was extracted with ethyl acetate. The aqueous layer was extracted with ethyl acetate. The combined organic layer was washed with $H_2O$, brine, and then dried with $Na_{0.2}SO_4$ and concentrated. The residue was purified by chromatography (on silica gel, ethyl acetate/hexane=1/9) to yield a colorless oil in 5.32 g. It was dissolved in 150 ml THF and 100 ml 2N HCl solution. The reaction was stirred at reflux for 15 min. THF was evaporated and the residue was diluted with $H_2O$ and ethyl acetate. The aqueous layer was extracted with ethyl acetate. The combined organic layer was washed with 5% $NaHCO_3$ solution, brine, and dried with $MgSO_4$, and concentrated. The residue was purified by chromatography (on silica gel, ethyl acetate/hexane=1/9) to yield a colorless oil in 4.52 g. NMR spectra of the product were consistent for the proposed structure.

Step 6

A solution of silver nitrate (3.26 g, 19.3 mmol) in 6 ml $H_2O$ was added to a solution of the product of step 5 (2.0 g, 9.6 mmol) in 45 ml ethanol. A solution of Sodium hydroxide (1.54 g, 38.4 mmol) in 6 ml $H_2O$ was added dropwise at room temperature. After 2 h, the reaction was filtered through a pad of Celite®. The residue was diluted with $H_2O$ and extracted with ether (3×30 ml). The aqueous layer was acidified with concentrated HCl and extracted with chloroform. The organic layer was dried with $MgSO_4$ and concentrated to give 1.82 g of yellow solid. This solid was dissolved in 50 ml ethanol and 25 ml 4N HCl in dioxane. It was stirred at room temperature for 48 h. Ethanol and dioxane were evaporated to afford a clean product as a pale brown oil in 2.0 g. NMR spectra of the product were consistent for the proposed structure.

Step 7

The product of step 6 (2.0 g, 8.6 mmol) was dissolved in 15 ml methylene chloride. Under $N_2$ boron tribromide solution (15 ml, 15 mmol, 1M in methylene chloride) was added to the above solution dropwise at 0° C. The resulting reaction solution was allowed to warm to room temperature. After 30 min, the reaction was carefully quenched with ethanol. The product was extracted with ethyl acetate and washed with 1N HCl. The organic layer was washed with 5% $NaHCO_3$ solution, brine, dried with $MgSO_4$, and concentrated. The residue was purified by chromatography (on silica gel, ethyl acetate/hexane=3/7) to give pale brown oil in 1.63 g. NMR spectra of the product were consistent for the proposed structure.

Step 8

A solution of diethyl azodicarboxylate (731 mg, 4.2 mmol) in 5 ml THF was added to a solution of the product of step 7 (750 mg, 3.4 mmol) and triphenylphosphine (1.1 g, 4.2 mmol) in 20 ml THF at room temperature and stirred for 15 min. 2-(3-hydroxypropylamino)pyridine N-oxide (706 mg, 4.2 mmol) was added. The reaction was stirred at room temperature for 18 h. THF was evaporated and the residue was purified by chromatography (on silica gel, $CH_2Cl_2$/$CH_3OH$/$NH_4OH$-98.5/1/0.5) to yield 835 mg pale brown oil. NMR spectra of the product were consistent for the proposed structure.

Step 9

A mixture of the product of step 8 (835 mg, 2.15 mmol), 10% Pd/C (250 mg, 0.24 mmol), cyclohexene (3.0 ml, 29.6 mmol), and 2-propanol (20 ml) was heated at reflux for 4 h. The reaction was allowed to cool to room temperature. Additional 10% Pd/C (250 mg, 0.24 mmol) was added. After 4 h of refluxing, the reaction was cooled to room temperature, filtered through a short column of Celite®, and washed with 2-propanol. The filtrate was concentrated. The residue was purified by chromatography (on silica gel, $CH_2Cl_2$/$CH_3OH$/$NH_4OH$=98.5/1/0.5) to give 482 mg colorless oil. The NMR spectra were consistent for the proposed structure.

Step 10

The product of step 9 (475 mg, 1.28 mmol) was dissolved in 10 ml methanol and 10 ml 1N sodium hydroxide solution. The reaction was stirred at room temperature for 18 h and acidified with 2 ml trifluoroacetic acid. Solvents were evaporated. The residue was purified on HPLC using acetonitrile gradient 10–50% in 30 min to yield 434 mg gummy solid. FAB-MS:(MH+)=345.4.H-NMR($CDCl_3$) δ 0.86 (dt, 1H), 0.95 (dt, 1H), 1.30 (m, 1H), 1.72 (dt, 1lH), 2.18 (p, 2H), 2.40 (dd, 1H), 2.49 (dd, 1H), 3.58 (t, 1H), 4.10 (t, 2H), 6.72 (t, 1H), 6.80–6.90 (m, 3H), 6.95 (d, 1H), 7.80 (t, 1H), 7.81 (d, 1H), 9.09 (br, 1H). Anal Calcd. for $C_{19}H_{21}N_2O_3F$ plus 1.5 $CF_3COOH$: C, 51.27; H, 4.40; N, 5.44. Found: C, 51.12; H, 4.40; N, 5.57.

EXAMPLE 10

2-[2-fluoro-4-[3-(2-pyridinylamino)propoxy]phenyl]cyclopropaneacetic Acid

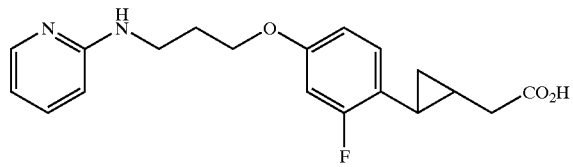

The title compound was prepared according to procedure described for the preparation of EXAMPLE 12: FAB-MS: (MH+)=345.4. $^1$H NMR (DMSO-6d) δ 0.82 (dt, 1H), 0.86 (dt, 1H), 1.23 (m, 1H), 1.78 (dt, 1H), 2.04 (p, 2H), 2.31 (dd, 1H), 2.37 (dd, 1H), 3.48 (t, 2H), 4.07 (t, 2H), 6.69 (dd, 1H), 6.77 (dd, 1H), 6.86 (t, 1H), 6.96 (t, 1H), 7.06 (d, 1H), 7.90 (t, 1H), 7.94 (d, 1H), 8.84 (br, 1H). Anal Calcd. for $C_{19}H_{21}N_2O_3F$ plus 1.75 $CF_3COOH$: C, 49.68; H, 4.22; N, 5.15. Found: C, 49.58; H, 3.96; N, 5.09.

EXAMPLE 11

2-[4-[2-[6-(methylamino)-2-pyridinyl]ethoxy]phenyl]]cyclopropaneacetic acid

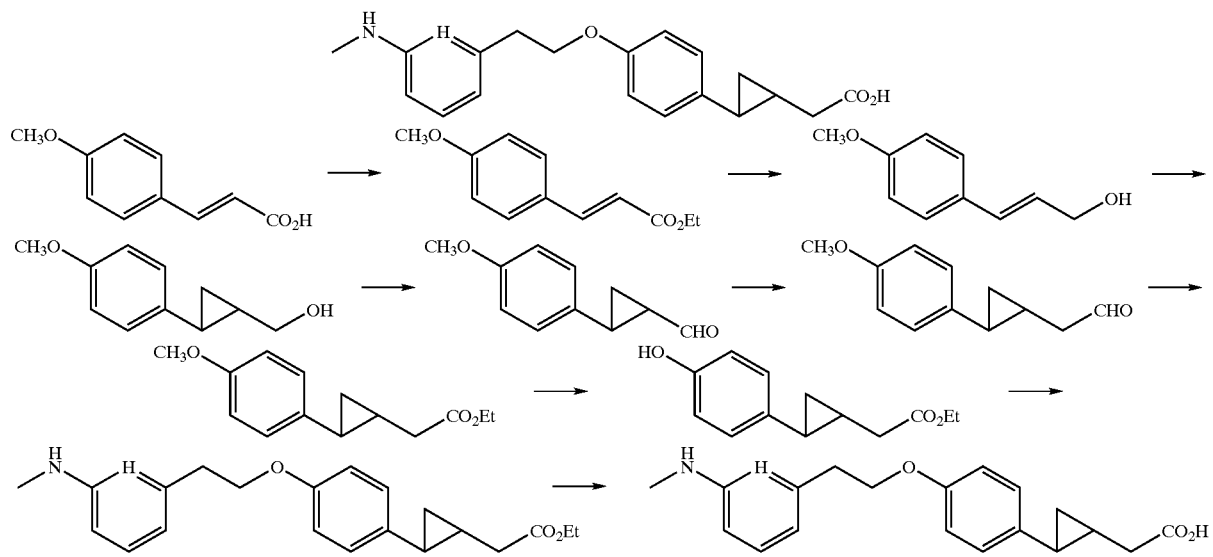

Step 1

A mixture of trans-4-methoxycinnamic acid (50 g, 281 mmol), 5 ml concentrated $H_2SO_4$, and 500 ml ethanol was stirred at reflux for 18 h. The cooled reaction was quenched with saturated $NaHCO_3$ solution. The product was extracted with ether. The organic layer was dried with $MgSO_4$ and concentrated. The residue was solidified at room temperature to yield a pale brown solid in 54.8 g. NMR spectra of the product were consistent for the proposed structure.

Step 2

The product of step 1 (20.6 g, 100 mmol) was dissolved in 150 ml THF. It was added to a solution of diisobutylalumium hydride (300 ml, 1M in THF) diluted with THF (150 ml) at 0° C. under $N_2$ over 20 min. After 1 h, the reaction was quenched with 50 ml acetone and 25 ml ethanol. The resulting mixture was poured into $H_2O$ and acidified with 1N HCl. The product was extracted with ethyl acetate. The organic layer was dried with $MgSO_4$, and concentrated to yield an off-white solid in 15.62 g. This product was used without further purification. NMR spectra of the product were consistent for the proposed structure.

Step 3

Diethyl zinc solution (100 ml, 100 mmol, 1.0 M in hexane) was added to a solution of diiodomethane (16.1 ml, 200 mmol) in 175 ml dichloromethane at 0° C. over 15 min. After stirring at 0° C. for 15 min, a solution of the product of step 2 (15.6 g, 95 mmol) in 50 ml dichloromethane was added dropwise at 0° C. over 15 min. After 15 min, the reaction was quenched with 200 ml 1N HCl at 5° C. The product was extracted with dichloromethane. The organic layer was dried with $MgSO_4$ and concentrated to give a golden oil in 16.47 g. NMR spectra of the product were consistent for the proposed structure.

Step 4

The product of step 3 (3.5 g, 19.6 mmol) was dissolved in 40 ml dichloromethane. 4-methylmorpholine-N-oxide (3.5 g, 30 mmol) and dry molecular sieves (10.0 g, 4A) were added. The resulting mixture was stirred at room temperature for 15 min. Tetrapropylammonuim perruthenate (0.351 g, 1.0 mmol) was added. The reaction was stirred at room temperature for 2.5 h and filtered through a short column of Celite®. The filtrate was concentrated and residue was purified by chromatography (on silica gel, ethyl acetate/hexane=3/7) to afford a golden oil in 1.9 g. NMR spectra of the product were consistent for the proposed structure.

Step 5

Under $N_2$, lithium bis(trimethylsilyl) amide solution (90 ml, 1.0M in THF) was added to a mixture of methoxy methyltriphenyl phosphonium chloride (29.2 g, 85 mmol) in 60 ml THF dropwise at 0° C. After 15 min, it was added to a solution of the product of step 4 (10.0 g, 56.8 mmol) in 30 ml THF was added at 0° C. The reaction was stirred for 5 min and quenched with $H_2O$. The product was extracted with ethyl acetate. The aqueous layer was extracted with ethyl acetate. The combined organic layer was washed with $H_2O$, brine, dried with $Na_2SO_4$, and concentrated. The residue was purified by chromatography (on silica gel, ethyl acetate/hexane=1/9) to yield a pale brown oil in 8.6 g. It was dissolved in 125 ml THF and 125 ml 1.5N HCl solution. The resulting solution was stirred at reflux for 1 h. THF was evaporated and residue was diluted with $H_2O$ and ethyl acetate. The aqueous layer was extracted with ethyl acetate. The combined organic layer was washed with 5% NaHCO$_3$ solution, brine, dried with MgSO$_4$, and concentrated to afford a yellow oil in 7.8 g. This product was used without further purification. NMR spectra of the product were consistent for the proposed structure.

Step 6

A solution of silver nitrate (13.9 g, 82.0 mmol) in 20 ml H$_2$O was added to a solution of the product of step 5 (7.8 g, 41.0 mmol) in 200 ml ethanol. A solution of Sodium hydroxide (6.6 g, 164.0 mmol) in 10 ml H$_2$O was added dropwise at room temperature. After 2 h, the reaction was filtered through a short column of Celite®. The filtrate was diluted with H$_2$O and extracted with ether (3×30 ml). The aqueous layer was acidified with concentrated HCl and extracted with chloroform. The chloroform layer was dried with MgSO$_4$ and concentrated. The residue was dissolved in 150 ml ethanol and 50 ml 4N HCl in dioxane. The resulting reaction solution was stirred at room temperature for 18 h and concentrated to afford a brown oil in 7.88 g. This product was used without further purification. NMR spectra of the product were consistent for the proposed structure.

Step 7

Boron tribromide solution (40 ml, 40 mmol, 1 M in dichloromethane) was added to a solution of the product of step 6 (7.8 g, 32.9 mmol) in 50 ml dichloromethane dropwise at 0° C. The resulting reaction solution was allowed to warm to room temperature. After 30 min, the reaction was carefully quenched with ethanol. The product was extracted with ethyl acetate and washed with 1N HCl. The organic layer was further washed with 5% NaHCO$_3$ solution, brine, and dried with MgSO$_4$, and concentrated. The residue was purified by chromatography (on silica gel, ethyl acetate/hexane=1/3) to give a pale brown oil in 3.84 g. NMR spectra of the product were consistent for the proposed structure.

Step 8

A solution of diethyl azodicarboxylate (348 mg, 2.0 mmol) in 2 ml THF was added to a solution of the product of step 7 (275 mg, 1.25 mmol) and triphenylphosphine (525 mg, 2.0 mmol) in 10 ml THF at room temperature and stirred for 15 min. 6-(methylamino)-2-pyridyl ethanol (304 mg, 2.0 mmol) was added. The resulting reaction mixture was stirred at room temperature for 3 h. THF was evaporated and the residue was purified by chromatography (on silica gel, ethyl acetate/hexane=1/1) to yield a solid in 500 mg. NMR spectra of the product were consistent for the proposed structure.

Step 9

The product of step 8 (500 mg, 1.4 mmol) was dissolved in 25 ml methanol and 25 ml 1N sodium hydroxide solution. The reaction was stirred at room temperature for 18 h, acidified with 4 ml trifluoroacetic acid, and concentrated. The residue was purified on HPLC using acetonitrile gradient 15–50% in 30 min to yield 200 mg. FAB-MS:(MH+)= 327.4.H NMR (CDCl3) δ 0.82 (dt, 1H), 0.94 (dt, 1H), 1.3 (m, 1H), 1.73 (dt, 1lH), 2.43 (d, 2H), 2.97 (s, 3H), 3.23 (t, 2H), 4.29 (t, 2H), 6.59 (d, 1H), 6.68 (d, 1H), 6.80 (d, 2H), 7.02 (d, 2H), 7.73 (dd, 1H), 9.84 (br, 1H). Anal Calcd. for C$_{19}$H$_{22}$N$_2$O$_3$ plus 1.45 CF$_3$COOH: C, 53.49; H, 4.81; N, 5.70. Found: 53.64; H, 5.06; N, 5.92.

EXAMPLE 12

2-[4-[2-(3,4-dihydro-2H-pyrido[3,2-b]-1,4-oxazin-6-yl)ethoxy]phenyl]-cyclopropaneacetic Acid

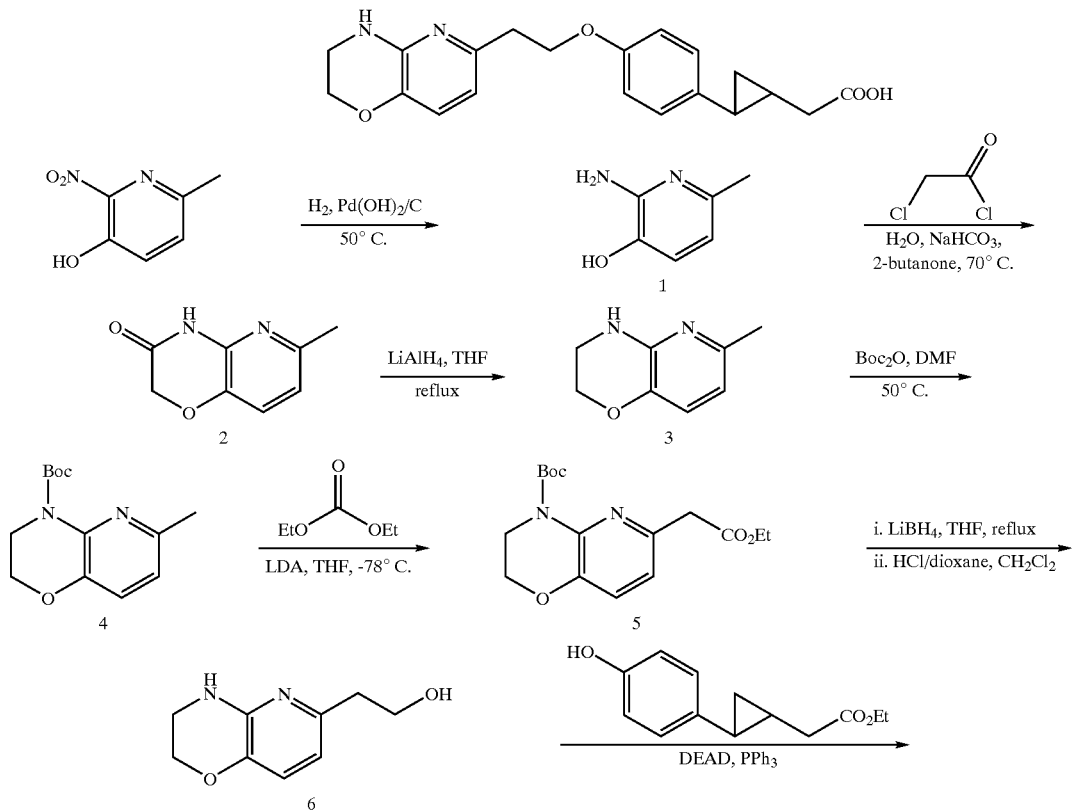

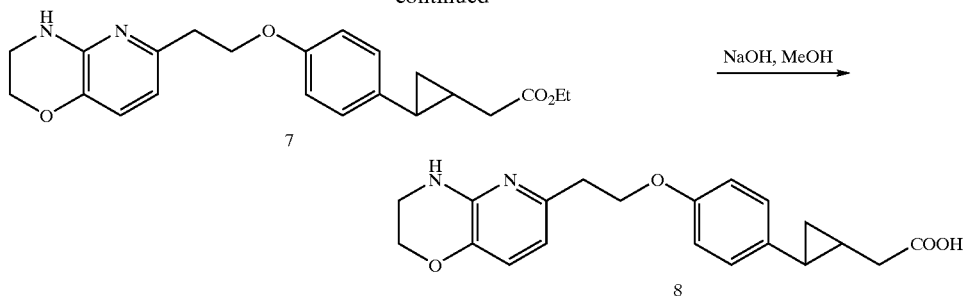

Step 1
2-amino-6-methyl-3-pyridinol
3-Hydroxy-6-methyl-2-nitropyridine (30 g, 194.6 mmol) was hydrogenated in ethanol solution at 50° C. using $H_2$ at 5 psi and 20% Pd(OH)$_2$/C catalyst for 1 hour. Upon completion of the reaction, the catalyst was filtered off and the filtrate was concentrated under reduced pressure to get the desired product 1 as a brown solid (23.68 g, 98%). NMR data was consistent with the proposed structure.

Step 2
6-methyl-2H-pyrido[3,2-b]-1,4-oxazin-3(4h)-one
chloroacetyl chloride (0.37 mL) was added dropwise to a stirred, cooled (0° C.) mixture of 1 (0.500 g), 0.810 g NaHCO$_3$, and 4 mL 2-butanone in 4 mL water. Once the addition was complete, the reaction mixture was warmed to room temp. and stirred for 30 minutes, then heated to 75° C. for 2 hours. The reaction mixture was cooled to room temp. and the 2-butanone was stripped off under reduced pressure. 1 mL water was added and the solids were filtered off and washed with water to get the crude product. The solid was dissolved in warmed (50° C.) ethyl acetate and filtered through a small plug of silica gel. The silica gel was washed with more warm ethyl acetate, combined with the filtrate, and concentrated under reduced pressure to get the desired product 2 (0.250 g, 38%) as a deep orange solid. NMR data was consistent with the proposed structure.

Step 3
Synthesis of 3,4-dihydro-6-methyl-2H-pyrido[3,2-b]-1,4-oxazine
LiAlH$_4$ (0.289 g) was slowly added to 15 mL dry THF in a round-bottom flask fitted with a stirbar and a condenser. After stirring for 10 minutes, a solution of 2 (1.00 g) in 15 mL dry THF was added dropwise. Upon completion of the addition, the reaction mixture was refluxed for 16 hours. The reaction was cooled to room temp. and quenched with 1 M NaOH solution until the mixture had become a milky yellow color. The precipitate was filtered off and washed 3 times with CH$_2$Cl$_2$. The filtrate and washings were combined, washed with brine, dried over MgSO$_4$, and concentrated under reduced pressure to get 3 (0.910 g, 99%) as a pale yellow oil, which solidified on standing. NMR data was consistent with the proposed structure.

Step 4
2,3-dihydro-6-methyl-4H-pyrido[3,2-b]-1,4-oxazine-4-carboxylic acid, 1,1-dimethylethyl Ester
A solution of 3 (2.96 g), di-tert-butyl dicarbonate (4.302 g) and triethylamine (2.75 mL) in 35 mL DMF was warmed to 50° C. with stirring for 16 hours. The reaction mixture was allowed to cool to room temp. and was concentrated under reduced pressure to get the crude product, which was purified by chromatography on silica gel (eluent: 30/70 ethyl acetate/hexane). The desired fractions were combined and concentrated under reduced pressure to get the desired product 4 (1.46 g, 30%) as a yellow oil. NMR data was consistent with the proposed structure.

Step 5
4-[(1,1-dimethylethoxy)carbonyl]-3,4-dihydro-2H-pyrido[3,2-b]-1,4-oxazine-6-acetic Acid, Ethyl Ester
Lithium diisopropylamide solution (8.17 Ml, 2.0 M in THF/ethylbenzene/heptane) was added dropwise to a chilled (−78° C.), stirred solution of 4 (1.46 g) and diethyl carbonate (2.549 g) in 15 mL dry THF under nitrogen atmosphere. After 30 minutes the reaction was quenched with saturated NH$_4$Cl solution and warmed to room temp. The mixture was extracted three times with ethyl acetate and all organic extracts were combined, dried over MgSO$_4$, and concentrated under reduced pressure to get the crude product, which was purified by chromatography on silica gel (eluent: 40/60 ethyl acetate/hexane). The desired fractions were combined and concentrated under reduced pressure to get the desired product 5 (1.48 g, 78%) as a yellow solid. NMR data was consistent with the proposed structure.

Step 6
3,4-dihydro-2H-pyrido[3,2-b]-1,4-oxazine-6-ethanol
To a solution of 5 (1.48 g) in dry THF (20 mL) at room temp. was added a solution of LiBH$_4$ (2.0 M in THF, 2.75 mL), and the resulting mixture was heated to reflux. After 16 hours the mixture was cooled to 0° C. and carefully quenched with water (20 mL). After 10 minutes, the mixture was extracted three times with ethyl acetate. The combined organic extracts were dried over MgSO$_4$, filtered, and concentrated under reduced pressure. This residue was dissolved in CH$_2$Cl$_2$ (3 mL), and to this solution was added 4 M HCl in dioxane (6 mL) all at once at room temp. After 4 hours, the mixture was concentrated under reduced pressure to get the crude product, which was chromatographed on silica gel (eluent: 94.5/5/0.5 chloroform/ethanol/ammonium hydroxide). The desired fractions were combined and concentrated under reduced pressure to get the desired product 6 (0.364 g, 44%) as a pale yellow solid. H MNR(CDCl3) δ 2.78 (t, 2H), 3.55 (m, 2H), 3.92 (t, 2H), 4.23 (m, 2H), 6.40 (d, 2H), 6.90 (d, 2H).

Step 7
2-[4-[2-(3,4-dihydro-2H-pyrido[3,2-b]-1,4-oxazin-6-yl) ethoxy]phenyl]cyclopropaneacetic Acid, Ethyl Ester
A solution of diethyl azodicarboxylate (348 mg, 2.0 mmol) in 2 ml THF was added to a solution of the product of step 8, EXAMPLE 11 (366 mg, 1.66 mmol) and triphenylphosphine (525 mg, 2.0 mmol) in 10 ml THF at room temperature and stirred for 15 min. The product of step 6 (360 mg, 2.0 mmol) was added. The resulting reaction mixture was stirred at room temperature for 3 h. THF was evaporated and the residue was purified by chromatography (on silica gel, CH$_2$Cl$_2$/CH$_3$OH/NH$_4$OH 98.5/1/0.5) to yield an yellow oil in 380 mg. NMR spectra of the product were consistent for the proposed structure.

Step 8

2-[4-[2-(3,4-dihydro-2H-pyrido[3,2-b]-1,4-oxazin-6-yl)ethoxy]phenyl]cyclopropaneacetic Acid The product of step 7 (380 mg, 1 mmol) was dissolved in 5 ml methanol and 2.5 ml 1N sodium hydroxide solution. The reaction was stirred at room temperature for 18 h, acidified with 1 ml trifluoroacetic acid, and concentrated. The residue was purified on HPLC using acetonitrile gradient 15–50% in 30 min to yield 210 mg desired product as an yellow oil. FAB-MS:(MH+)=355.H MNR(CDCl3) δ 0.78 (m, 1H), 0.86 (m, 1H), 1.21 (m, 1H), 1.70 (m, 1H), 2.35 (m, 2H), 3.12 (t, 2H), 3.63 (t, 2H), 4.22 (t, 2H), 4.26 (t, 2H), 6.65 (d, 1H), 6.79 (d, 2H), 7.0 (d, 2H), 7.6 (d, 1H). Anal Calcd. for $C_{20}H_{22}N_2O_4$ plus 1 $CF_3COOH$ and $0.2H_2O$: C, 55.98; H, 5.00; N, 5.93. Found: 55.90; H, 5.28; N, 5.24.

EXAMPLE 13

3-[4-[3-(2-pyridinylamino)propoxy]phenyl]cyclobutaneacetic Acid

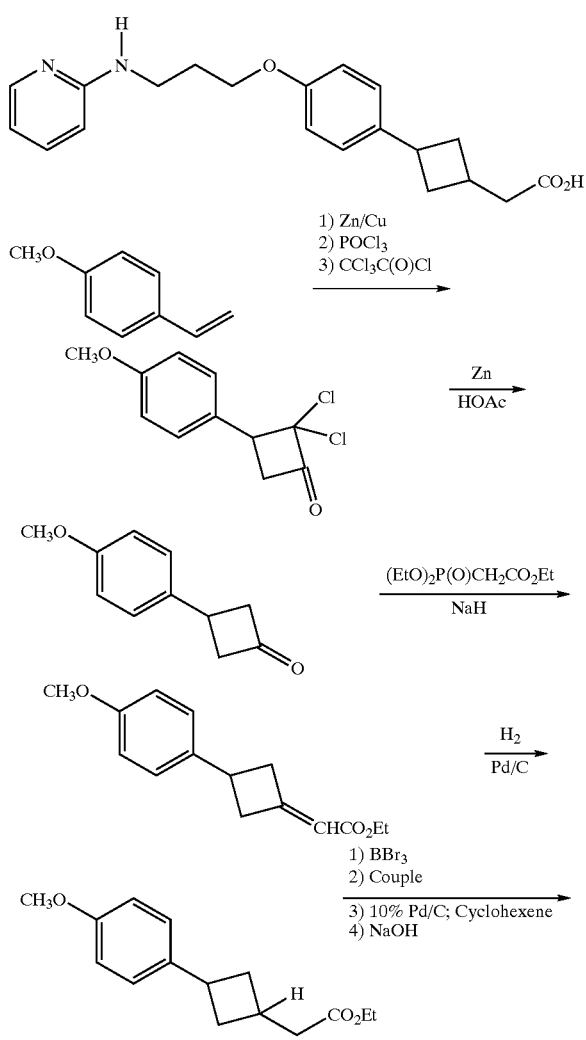

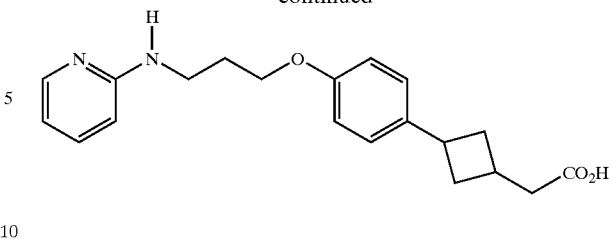

The compounds of Formula 1 containing a cyclobutyl with a 1,3-substituion can be synthesized as shown in the above scheme. For example, reaction of 4-methoxystyrene with in-situ generated dichloroketene gives the cycloadduct which can be dehalogenated to give the cyclobutanone derivative shown in Step 2. The reaction described in Tetrahedron Asymmetry 10, 2113–2118, 1999 for other substituted styrenes can be used to accomplish their synthesis. Elaboration of this intermediate involving Horner-Emmons reaction, reduction of olefin, demethylation, Mitsunobu reaction, deoxygenation and hydrolysis of ester gives the target compound. The experimental conditions described in Steps 2–7, in Example 2 can be used to achieve the synthesis of target compound.

EXAMPLE 14

(1-Methyl-2-{4-[3-(pyridin-2-ylamino)-propoxyl]-phenyl}-cyclopropyl)-acetic Acid

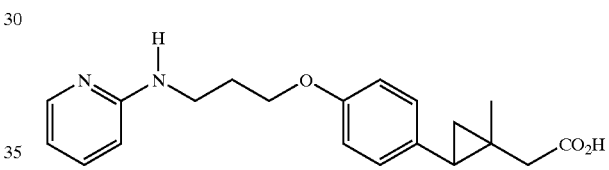

The title compound was prepared starting with benzaldehyde and triethylphosphonopropionoate following the reaction sequence shown in scheme 8. $^1$H MNR(CDCl$_3$) δ 0.83 (t, 1H), 0.86 (s, 3H), 0.93 (dd, 1H), 2.05 (dd, 1lH), 2.19 (p, 2H), 2.29 (d, 1H), 2.57 (d, 1H), 2.57 (d, 1H), 3.53 (q, 2H), 4.05 (t, 2H), 6.70 (t, 1H), 6.81 (d, 2H), 6.85 (d, 1H), 7.15 (d, 2H), 7.73 (ddd, 1H), 7.80 (d, 1H), 9.70 (br, 1H); MS (ESI) m/z =341 (MH+); Anal Calcd. for $C_{20}H_{24}N_2O_3$·1.65 $CF_3COOH$: C, 52.95; H, 4.89; N, 5.30. Found: 52.90; H, 4.95; N, 5.36.

EXAMPLE 15

(1-Methyl-2-{4-[2-(5,6,7,8-tetrahydro-[1,8]naphthyridin-2-yl)-ethoxy]-phenyl}-cyclopropyl)-acetic Acid

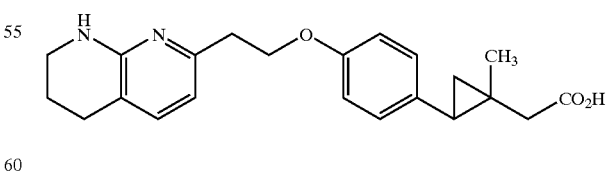

The title compound was prepared starting with benzaldehyde and triethylphosphonopropionoate following the reaction sequence shown in scheme 8. $^1$H MNR(CDCl$_3$) δ 0.83 (t, 1H), 0.86 (s, 3H), 0.92 (dd, 1H), 1.94 (p, 2H), 2.04 (dd, 1lH), 2.29 (d, 1H), 2.55 (d, 1H), 2.76 (t, 2H), 3.18 (t, 2H), 3.52 (t, 2H), 4.29 (t, 2H), 6.00 (brs, 2H), 6.53 (d, 1H), 6.82 (d, 2H), 7.15 (d, 2H), 7.34 (d, 1H), 9.64 (br, 1H); Anal Calcd.

for $C_{22}H_{26}N_2O_3 \cdot 0.1.5\ CF_3COOH$: C, 56.81; H, 5.50; N, 5.42. Found: 57.13; H, 5.50; N, 5.08.

EXAMPLE 16

(2-{2-Methoxy-4-[3-(pyridin-2-ylamino)-propoxy]-phenyl}-cyclopropyl)-acetic Acid

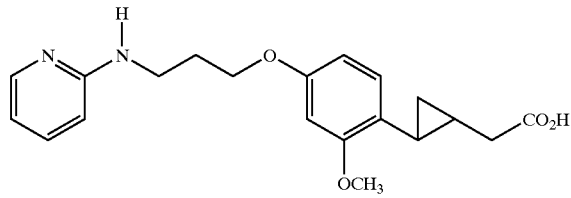

The title compound is prepared according to the general procedures described in SCHEME 11.

EXAMPLE 17

[1-Methyl-2-(4-{2-[6-(2,2,2-trifluoro-ethylamino)-pyridin-2-yl]-ethoxy}-phenyl)-cyclopropyl]-acetic Acid

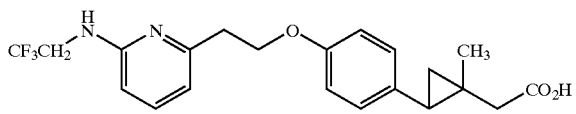

The title compound is prepared according to the general procedures described in SCHEME 10.

EXAMPLE 18

(2-{4-[2-(6-Ethylamino-pyridin-2-yl)-ethoxy]-phenyl}-cyclopropyl)-acetic Acid

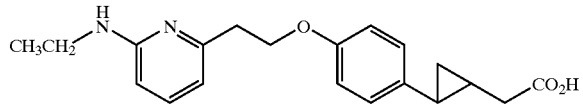

The title compound is prepared according to the general procedures described in SCHEME 10.

EXAMPLE 19

[2-(4-{2-[6-(2-Methoxy-ethylamino)-pyridin-2-yl]-ethoxy}-phenyl)-cyclopropyl]-acetic Acid

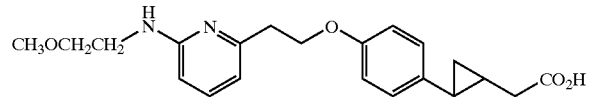

The title compound is prepared according to the general procedures described in SCHEME 10.

EXAMPLE 20

[2-(4-{2-[6-(2,2,2-Trifluoro-ethylamino)-pyridin-2-yl]-ethoxy}-phenyl)-cyclopropyl]-acetic Acid

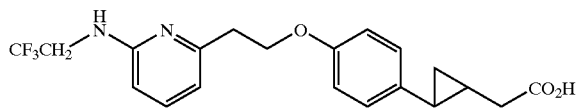

The title compound is prepared according to the general procedures described in SCHEME 10.

EXAMPLE 21

[2-(4-{2-[6-(3-Methoxy-propylamino)-pyridin-2-yl]-ethoxy}-phenyl)-cyclopropyl]-acetic Acid

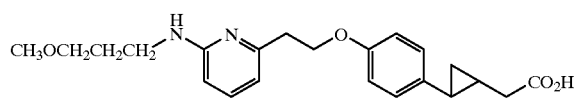

The title compound is prepared according to the general procedures described in SCHEME 10.

EXAMPLE 22

(2-{2-Fluoro-4-[3-(pyridin-2-ylamino)-propoxy]-phenyl}-cyclopropyl)-acetic Acid

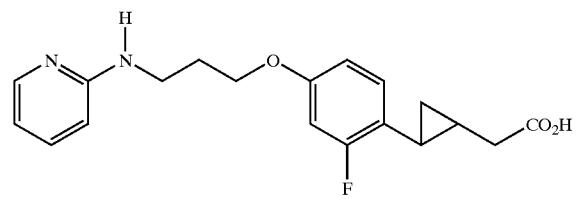

The title compound is prepared according to the general procedures described in SCHEME11.

EXAMPLE 23

(2-{2-Acetoxy-4-[3-(pyridin-2-ylamino)-propoxy]-phenyl}-cyclopropyl)-acetic Acid

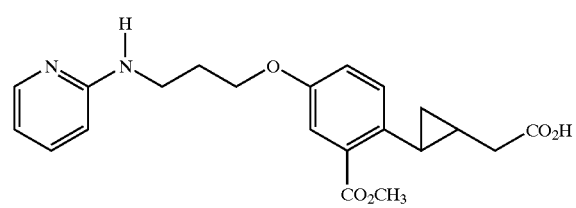

The title compound is prepared according to the general procedures described in SCHEME11.

EXAMPLE 24

(1-Methoxymethyl-2-{4-[3-(pyridin-2-ylamino)-propoxy]-phenyl}-cyclopropyl)-acetic Acid

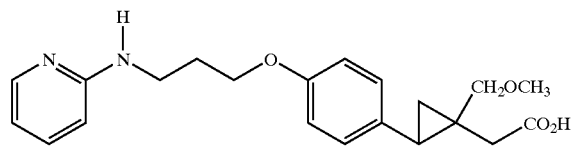

The title compound is prepared according to the general procedures described in SCHEME 8.

EXAMPLE 25

(1-Methanesulfonylmethyl-2-{4-[3-(pyridin-2-ylamino)-propoxy]-phenyl}-cyclopropyl)-acetic Acid

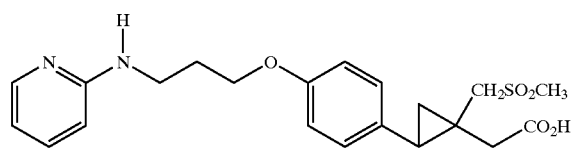

The title compound is prepared according to the general procedures described in SCHEME 8.

EXAMPLE 26

(1-Pyridin-3-yl-2-{4-[3-(pyridin-2-ylamino)-propoxy]-phenyl}-cyclopropyl)-acetic Acid

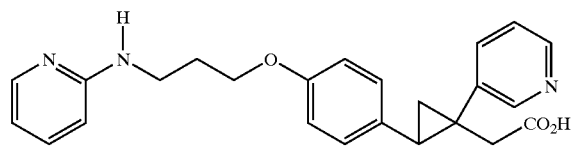

The title compound is prepared according to the general procedures described in SCHEME 8.

EXAMPLE 27

(1-Benzo[1,3]dioxol-5-yl-2-{4-[3-(pyridin-2-ylamino)-propoxy]-phenyl}-cyclopropyl)-acetic Acid

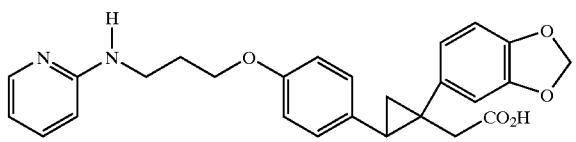

The title compound is prepared according to the general procedures described in SCHEME 8.

EXAMPLE 28

(1-(2,3-Dihydro-benzofuran-6-yl)-2-{4-[3-(pyridin-2-ylamino)-propoxy]-phenyl}-cyclopropyl)-acetic Acid

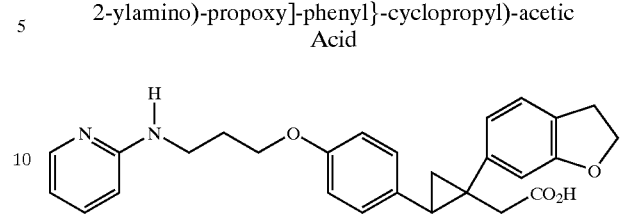

The title compound is prepared according to the general procedures described in SCHEME 8.

EXAMPLE 29

(1-Isoxazol-3-yl-2-{4-[3-(pyridin-2-ylamino)-propoxy]-phenyl}-cyclopropyl)-acetic Acid

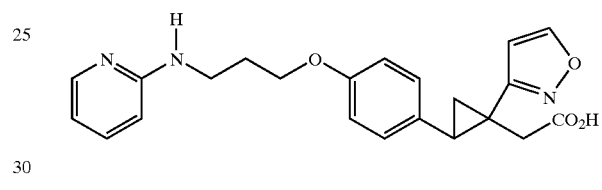

The title compound is prepared according to the general procedures described in SCHEME 8.

EXAMPLE 30

(1-Isoxazol-5-yl-2-{4-[3-(pyridin-2-ylamino)-propoxy]-phenyl}-cyclopropyl)-acetic Acid

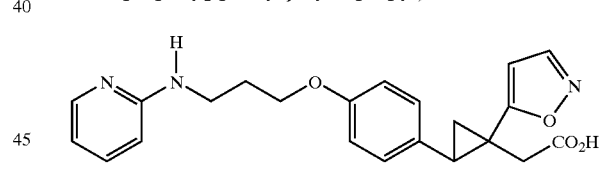

The title compound is prepared according to the general procedures described in SCHEME 8.

EXAMPLE 31

(1-Oxazol-5-yl-2-{4-[3-(pyridin-2-ylamino)-propoxy]-phenyl}-cyclopropyl)-acetic Acid

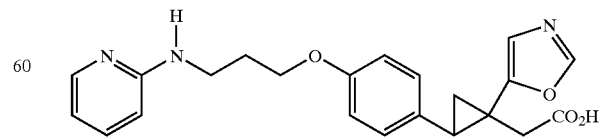

The title compound is prepared according to the general procedures described in SCHEME 8.

EXAMPLE 32

(2-{4-[3-(Pyridin-2-ylamino)-propoxy]-phenyl}-1-thiazol-5-yl-cyclopropyl)-acetic Acid

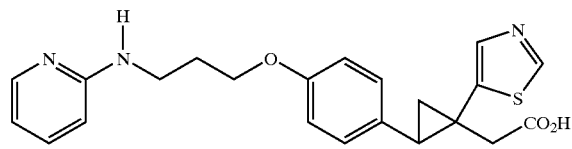

The title compound is prepared according to the general procedures described in SCHEME 8.

EXAMPLE 33

(1-Methoxymethyl-2-{4-[2-(5,6,7,8-tetrahydro-[1,8]naphthyridin-2-yl)-ethoxy]-phenyl}-cyclopropyl)-acetic Acid

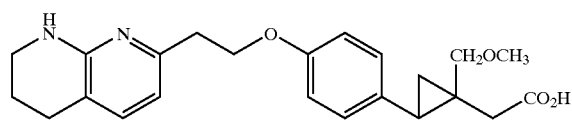

The title compound is prepared according to the general procedures described in SCHEME 8.

EXAMPLE 34

(1-Methanesulfonylmethyl-2-{4-[2-(5,6,7,8-tetrahydro-[1,8]naphthyridin-2-yl)-ethoxy]-phenyl}-cyclopropyl)-acetic Acid

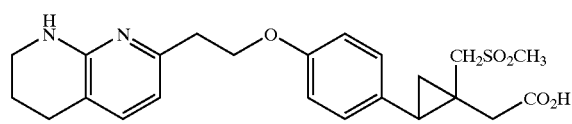

The title compound is prepared according to the general procedures described in SCHEME 8.

EXAMPLE 35

(1-Pyridin-3-yl-2-{4-[2-(5,6,7,8-tetrahydro-[1,8]naphthyridin-2-yl)-ethoxy]-phenyl}-cyclopropyl)-acetic acid

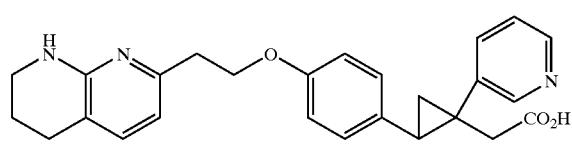

The title compound is prepared according to the general procedures described in SCHEME 8.

EXAMPLE 36

(1-(2,3-Dihydro-benzofuran-6-yl)-2-{4-[2-(5,6,7,8-tetrahydro-[1,8]naphthyridin-2-yl)-ethoxy]-phenyl}-cyclopropyl)-acetic Acid

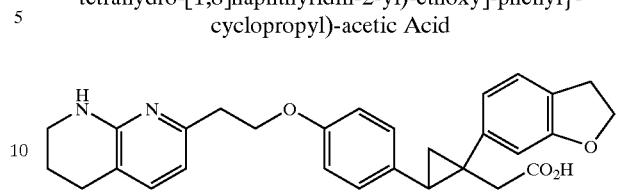

The title compound is prepared according to the general procedures described in SCHEME 8.

EXAMPLE 37

(1-Benzo[1,3]dioxol-5-yl-2-{4-[2-(5,6,7,8-tetrahydro-[1,8]naphthyridin-2-yl)-ethoxy]-phenyl}-cyclopropyl)-acetic Acid

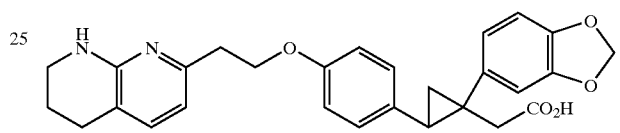

The title compound is prepared according to the general procedures described in SCHEME 8.

EXAMPLE 38

(1-Isoxazol-3-yl-2-{4-[2-(5,6,7,8-tetrahydro-[1,8]naphthyridin-2-yl)-ethoxy]-phenyl}-cyclopropyl)-acetic Acid

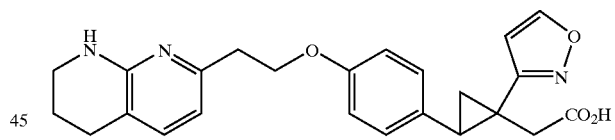

The title compound is prepared according to the general procedures described in SCHEME 8.

EXAMPLE 39

(1-Isoxazol-5-yl-2-{4-[2-(5,6,7,8-tetrahydro-[1,8]naphthyridin-2-yl)-ethoxy]-phenyl}-cyclopropyl)-acetic Acid

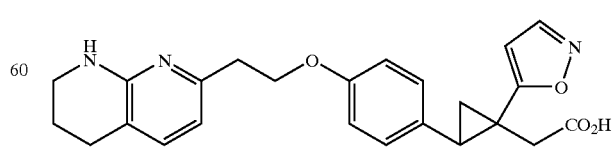

The title compound is prepared according to the general procedures described in SCHEME 8.

EXAMPLE 40

(1-Oxazol-5-yl-2-{4-[2-(5,6,7,8-tetrahydro-[1,8]
naphthyridin-2-yl)-ethoxy]-phenyl}-cyclopropyl)-
acetic Acid

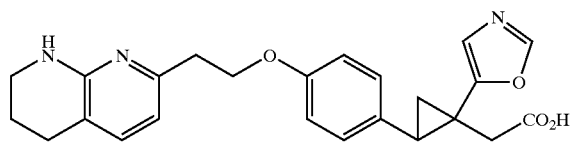

The title compound is prepared according to the general procedures described in SCHEME 8.

EXAMPLE 41

(2-{4-[2-(5,6,7,8-Tetrahydro-[1,8]naphthyridin-2-
yl)-ethoxy]-phenyl}-1-thiazol-5-yl-cyclopropyl)-
acetic Acid

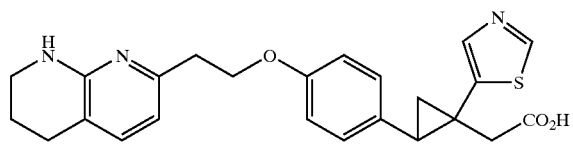

The title compound is prepared according to the general procedures described in SCHEME 8.

EXAMPLE 42

(2-{4-[3-(1-H-Imidazol-2-ylamino)-propoxy]-
phenyl}-cyclopropyl)-acetic Acid

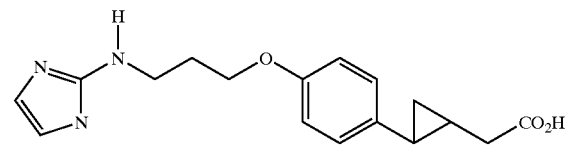

The title compound is prepared according to the general procedures described in SCHEME 9.

EXAMPLE 43

(2-{3-Fluoro-4-[3-(1-H-imidazol-2-ylamino)-
propoxy]-phenyl}-cyclopropyl)-acetic Acid

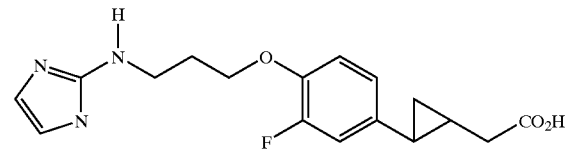

The title compound is prepared according to the general procedures described in SCHEME 9.

EXAMPLE 44

(2-{3-Fluoro-4-[3-(3-H-imidazol-4-ylamino)-
propoxy]-phenyl}-cyclopropyl)-acetic Acid

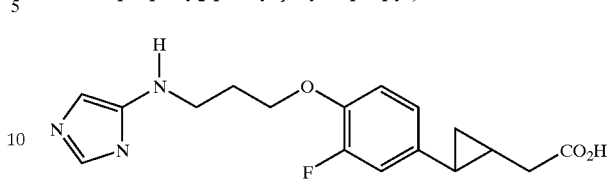

The title compound is prepared according to the general procedures described in SCHEME 9.

EXAMPLE 45

(2-{4-[3-(3-H-imidazol-4-ylamino)-propoxy]-
phenyl}-cyclopropyl)-acetic Acid

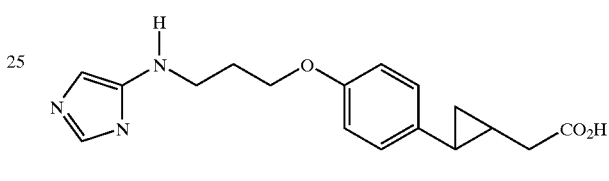

The title compound is prepared according to the general procedures described in SCHEME 9.

EXAMPLE 46

(2-{4-[3-(1-H-Pyrazol-3-ylamino)-propoxy]-
phenyl}-cyclopropyl)-acetic Acid

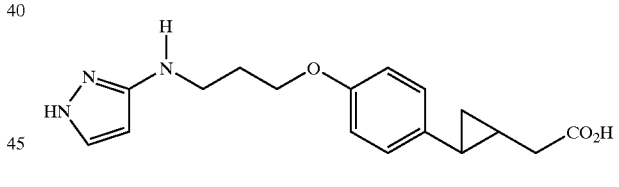

The title compound is prepared according to the general procedures described in SCHEME 9.

EXAMPLE 47

(2-{3-Fluoro-4-[3-(1-H-pyrazol-3-ylamino)-
propoxy]-phenyl}-cyclopropyl)-acetic Acid

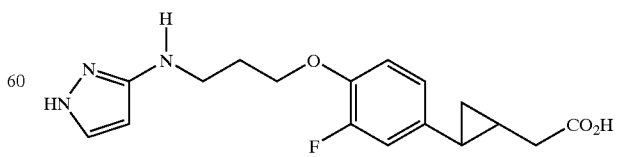

The title compound is prepared according to the general procedures described in SCHEME 9.

EXAMPLE 48

(1-Methyl-2-{4-[2-(6-methylamino-pyridin-2-yl)-ethoxy]-phenyl}-cyclopropyl)-acetic Acid

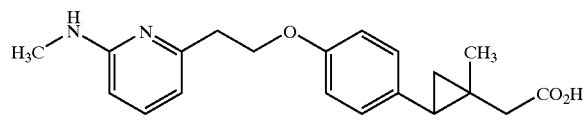

The title compound is prepared according to the general procedures described in SCHEME 10.

EXAMPLE 49

(2-{4-[2-(6-Ethylamino-pyridin-2-yl)-ethoxy]-phenyl}-1-methyl-cyclopropyl)-acetic Acid

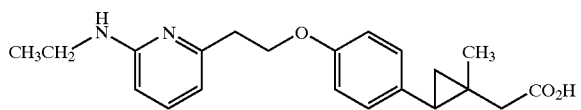

The title compound is prepared according to the general procedures described in SCHEME 10.

EXAMPLE 50

[2-(4-{2-[6-(2-Methoxy-ethylamino)-pyridin-2-yl]-ethoxy}-phenyl)-1-methyl-cyclopropyl]-acetic Acid

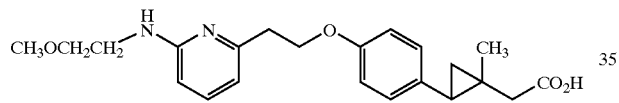

The title compound is prepared according to the general procedures described in SCHEME 10.

EXAMPLE 51

[2-(4-{2-[6-(3-Methoxy-propylamino)-pyridin-2-yl]-ethoxy}-phenyl)-1-methyl-cyclopropyl]-acetic Acid

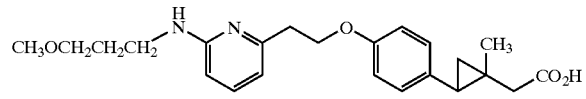

The title compound is prepared according to the general procedures described in SCHEME 10.

EXAMPLE 52

(2-{4-[2-(6-Acetylamino-pyridin-2-yl)-ethoxy]-phenyl}-1-methyl-cyclopropyl)-acetic Acid

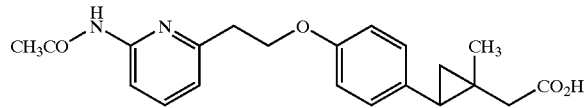

The title compound is prepared according to the general procedures described in SCHEME 10.

EXAMPLE 53

(2-{4-[2-(6-Acetylamino-pyridin-2-yl)-ethoxy]-phenyl}-cyclopropyl)-acetic Acid

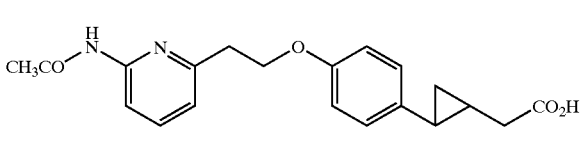

The title compound is prepared according to the general procedures described in SCHEME 10.

The activity of the compounds of the present invention was tested in the following assays.

Vitronectin Adhesion Assay

Materials

Human vitronectin receptors $\alpha_v\beta_3$ and $\alpha_v\beta_5$ were purified from human placenta as previously described [Pytela et al., Methods in Enzymology, 144:475–489 (1987)]. Human vitronectin was purified from fresh frozen plasma as previously described [Yatohgo et al., Cell Structure and Function, 13:281–292 (1988)]. Biotinylated human vitronectin was prepared by coupling NHS-biotin from Pierce Chemical Company (Rockford, Ill.) to purified vitronectin as previously described [Charo et al., J. Biol. Chem., 266(3):1415–1421 (1991)]. Assay buffer, OPD substrate tablets, and RIA grade BSA were obtained from Sigma (St. Louis, Mo.). Anti-biotin antibody was obtained from Sigma (St. Louis, Mo.). Nalge Nunc-lmmuno microtiter plates were obtained from Nalge Company (Rochester, N.Y.).

Methods

Solid Phase Receptor Assays

This assay was essentially the same as previously reported [Niiya et al., Blood, 70:475–483 (1987)]. The purified human vitronectin receptors $\alpha_v\beta_3$ and $\alpha_v\beta_5$ were diluted from stock solutions to 1.0 µg/mL in Tris-buffered saline containing 1.0 mM $Ca^{++}$, $Mg^{++}$, and $Mn^{++}$, pH 7.4 ($TBS^{+++}$). The diluted receptors were immediately transferred to Nalge Nunc-lmmuno microtiter plates at 100 µL/well (100 ng receptor/well). The plates were sealed and incubated overnight at 4° C. to allow the receptors to bind to the wells. All remaining steps were at room temperature. The assay plates were emptied and 200 µL of 1% RIA grade BSA in $TBS^{+++}$ ($TBS^{+++}$/BSA) were added to block exposed plastic surfaces. Following a 2 hour incubation, the assay plates were washed with $TBS^{+++}$ using a 96 well plate washer. Logarithmic serial dilution of the test compound and controls were made starting at a stock concentration of 2 mM and using 2 nM biotinylated vitronectin in $TBS^{+++}$/BSA as the diluent. This premixing of labeled ligand with test (or control) ligand, and subsequent transfer of 50 µL aliquots to the assay plate was carried out with a CETUS Propette robot; the final concentration of the labeled ligand was 1 nM and the highest concentration of test compound was 1.0× $10^{-4}$ M. The competition occurred for two hours after which all wells were washed with a plate washer as before. Affinity purified horseradish peroxidase labeled goat anti-biotin antibody was diluted 1:2000 in $TBS^{+++}$/BSA and 125 µL was added to each well. After 45 minutes, the plates were washed and incubated with $OPD/H_2O_2$ substrate in 100 mM/L Citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCEL spreadsheet program. The mean, standard deviation, and %CV were determined for duplicate concentrations. The mean $A_{450}$ values were normalized to the mean of four maximum-binding controls (no competitor added)(B-MAX). The normalized values were subjected to a four parameter curve fit algorithm [Rodbard et al., *Int. Atomic Energy Agency, Vienna*, pp 469 (1977)], plotted on a semi-log scale, and the computed concentration corresponding to inhibition of 50% of the maximum binding of 2 biotinylated vitronectin ($IC_{50}$) and corresponding $R^2$ was reported for those compounds exhibiting greater than 50% inhibition at the highest concentration tested; otherwise the $IC_{50}$ is reported as being greater than the highest concentration tested. β-[2-[5-[(aminoiminomethyl)amino]-1-oxopentyl]amino]-1-oxoethyl]amino]-3-pyridinepropanoic acid [U.S. Pat. No. 5,602,155 Example 1] which is a potent $α_vβ_3$ antagonist ($IC_{50}$ in the range 3–10 nM) was included on each plate as a positive control.

PURIFIED IIb/IIIa RECEPTOR ASSAY

Materials

Human fibrinogen receptor (IIb/IIIa) was purified from outdated platelets. (Pytela, R., Pierschbacher, M. D., Argraves, S., Suzuki, S., and Rouslahti, E. "Arginine-Glycine-Aspartic acid adhesion receptors", *Methods in Enzymology* 144(1987):475–489.) Human vitronectin was purified from fresh frozen plasma as described in Yatohgo, T., Izumi, M., Kashiwagi, H., and Hayashi, M., "Novel purification of vitronectin from human plasma by heparin affinity chromatography," *Cell Structure and Function* 13(1988):281–292. Biotinylated human vitronectin was prepared by coupling NHS-biotin from Pierce Chemical Company (Rockford, Ill.) to purified vitronectin as previously described. (Charo, I. F., Nannizzi, L., Phillips, D. R., Hsu, M. A., Scarborough, R. M., "Inhibition of fibrinogen binding to GP IIb/IIIa by a GP IIIa peptide", *J. Biol. Chem.* 266(3) (1991): 1415–1421.) Assay buffer, OPD substrate tablets, and RIA grade BSA were obtained from Sigma (St. Louis, Mo.). Anti-biotin antibody was obtained from Sigma (St. Louis, Mo.). Nalge Nunc-immuno microtiter plates were obtained from (Rochester, N.Y.). ADP reagent was obtained from Sigma (St. Louis, Mo.).

Methods

Solid Phase Receptor Assays

This assay is essentially the same reported in Niiya, K., Hodson, E., Bader, R., Byers-Ward, V. Koziol, J. A., Plow, E. F. and Ruggeri, Z. M., "Increased surface expression of the membrane glycoprotein IIb/IIIa complex induced by platelet activation: Relationships to the binding of fibrinogen and platelet aggregation", *Blood* 70(1987):475–483. The purified human fibrinogen receptor (IIb/IIIa) was diluted from stock solutions to 1.0 μg/mL in Tris-buffered saline containing 1.0 mM $Ca^{++}$, $Mg^{++}$, and $Mn^{++}$, pH 7.4 ($TBS^{+++}$). The diluted receptor was immediately transferred to Nalge Nunc-Immuno microtiter plates at 100 μL/well (100 ng receptor/well). The plates were sealed and incubated overnight at 4° C. to allow the receptors to bind to the wells. All remaining steps were at room temperature. The assay plates were emptied and 200 μL of 1% RIA grade BSA in $TBS^{+++}$ ($TBS^{+++}$/BSA) were added to block exposed plastic surfaces. Following a 2 hour incubation, the assay plates were washed with $TBS^{+++}$ using a 96 well plate washer. Logarithmic serial dilution of the test compound and controls were made starting at a stock concentration of 2 mM and using 2 nM biotinylated vitronectin in $TBS^{+++}$/BSA as the diluent. This premixing of labeled ligand with test (or control) ligand, and subsequent transfer of 50 μL aliquots to the assay plate was carried out with a CETUS Propette robot; the final concentration of the labeled ligand was 1 nM and the highest concentration of test compound was 1.0× $10^{-4}$ M. The competition occurred for two hours after which all wells were washed with a plate washer as before. Affinity purified horseradish peroxidase labeled goat anti-biotin antibody was diluted 1:2000 in $TBS^{+++}$/BSA and 125 μL were added to each well. After 45 minutes, the plates were washed and incubated with $ODD/H_2O_2$ substrate in 100 mM/L citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCELJ spreadsheet program. The mean, standard deviation, and %CV were determined for duplicate concentrations. The mean $A_{450}$ values were normalized to the mean of four maximum-binding controls (no competitor added) (B-MAX). The normalized values were subjected to a four parameter curve fit algorithm, [Robard et al., *Int. Atomic Energy Agency Vienna*, pp 469 (1977)], plotted on a semi-log scale, and the computed concentration corresponding to inhibition of 50% of the maximum binding of biotinylated vitronectin ($IC_{50}$) and corresponding $R^2$ was reported for those compounds exhibiting greater than 50% inhibition at the highest concentration tested; otherwise the $IC_{50}$ is reported as being greater than the highest concentration tested. β-[2-[5-[(aminoiminomethyl)amino]-1-oxopentyl]amino]-1-oxoethyl]amino]-3-pyridinepropanoic acid [U.S. Pat. No. 5,602,155 Example 1] which is a potent $α_vβ_3$ antagonist ($IC_{50}$ in the range 3–10 nM) was included on each plate as a positive control.

Human Platelet Rich Plasma Assays

Healthy aspirin free donors were selected from a pool of volunteers. The harvesting of platelet rich plasma and subsequent ADP induced platelet aggregation assays were performed as described in Zucker, M. B., "Platelet Aggregation Measured by the Photometric Method", *Methods in Enzymology* 169(1989):117–133. Standard venipuncture techniques using a butterfly allowed the withdrawal of 45 mL of whole blood into a 60 mL syringe containing 5 mL of 3.8% trisodium citrate. Following thorough mixing in the syringe, the anti-coagulated whole blood was transferred to a 50 mL conical polyethylene tube. The blood was centrifuged at room temperature for 12 minutes at 200× g to sediment non-platelet cells. Platelet rich plasma was removed to a polyethylene tube and stored at room temperature until used. Platelet poor plasma was obtained from a second centrifugation of the remaining blood at 2000× g for 15 minutes. Platelet counts are typically 300,000 to 500,000 per microliter. Platelet rich plasma (0.45 mL) was aliquoted into siliconized cuvettes and stirred (1100 rpm) at 37° C. for 1 minute prior to adding 50 uL of pre-diluted test compound. After 1 minute of mixing, aggregation was initiated by the addition of 50 uL of 200 uM ADP. Aggregation was recorded for 3 minutes in a Payton dual channel aggregometer (Payton Scientific, Buffalo, N.Y.). The percent inhibition of maximal response (saline control) for a series of test compound dilutions was used to determine a dose response curve. All compounds were tested in duplicate and the concentration of half-maximal inhibition ($IC_{50}$) was calculated graphically from the dose response curve for those compounds which exhibited 50% or greater inhibition at the highest concentration tested; otherwise the $IC_{50}$ is reported as being greater than the highest concentration tested.

What is claimed is:
1. A compound of the formula

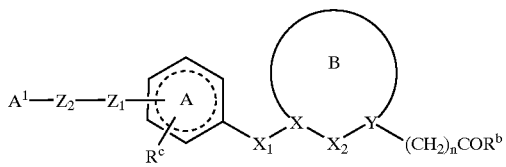

or a pharmaceutically acceptable salt thereof, wherein

is a 4–8 membered monocyclic ring or 7–12 membered bicyclic ring; which ring is optionally saturated or unsaturated, which ring is optionally substituted with one or more substituent selected from the group consisting of alkyl, haloalkyl, aryl, heteroaryl, halogen, alkoxyalkyl, aminoalkyl, hydroxy, nitro, alkoxy, hydroxyalkyl, thioalkyl, amino, alkylamino, arylamino, alkylsulfonamide, acyl, acylamino, alkylsulfone, sulfonamide, allyl, alkenyl, methylenedioxy, ethylenedioxy, alkynyl, carboxamide, cyano, and —$(CH_2)_m$ COR;

m is 0 to 2;

R is hydroxy, alkoxy, alkyl or amino;

$A^1$ is a pyridinyl of the formula

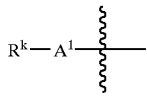

optionally substituted by one or more $R^k$ selected from the group consisting of hydroxy, alkyl, alkoxy, alkoxyalkyl, thioalkyl, haloalkyl, cyano, amino, alkylamino, halogen, acylamino, sulfonamide and —COR;

R is hydroxy, alkoxy, alkyl or amino;

with respect to $z^1$ and $Z^2$:

$Z^1$ is selected from the group consisting of $CH_2$, O, N, CO, S, SO, $SO_2$,

OH
|
CH and NRk;

$R_k$ is selected from H or lower alkyl;

$Z^2$ is a 2 to 5 carbon linker optionally containing one or more heteroatom selected from the group consisting of O, S and N; or $Z^1$–$Z^2$ contains a moiety selected from the group consisting of carboxamide, sulfone, sulfonamide, alkenylene, alkynylene, and acyl;

wherein the carbon and nitrogen atoms of $Z^1$–$Z^2$ are optionally substituted by alkyl, alkoxy, thioalkyl, alkylsulfone, aryl, alkoxyalkyl, hydroxy, alkylamino, heteroaryl, alkenyl, alkynyl, carboxyalkyl, halogen, haloalkyl or acylamino;

wherein $Z^2$–$Z^1$ is attached to

at the para or meta position relative to the X substituent;

n is 0 to 2;

$R^c$ is selected from the group consisting of hydrogen; alkyl; halogen, hydroxy, nitro, alkoxy, amino, haloalkyl, aryl, heteroaryl, alkoxyalkyl, aminoalkyl, hydroxyalkyl, thioalkyl, alkylamino, arylamino, alkylsulfonylamino, acyl, acylamino, sulfonyl, sulfonamide, allyl, alkenyl, methylenedioxy, ethylenedioxy, alkynyl, alkynylalkyl, carboxy, alkoxycarbonyl, carboxamido, cyano, and —$(CH_2)$, COR;

$X^1$ is selected from the group consisting of —O—, CO, $SO_2$, NR and $(CHR^p)_q$;

$R^m$ is H or alkyl;

$R^p$ is H, alkyl; alkoxy or hydroxy;

q is 0 or 1;

with respect to X, $X^2$ and Y:

$X^2$ is selected from the group consisting of —CHW—, CO, $SO_2$, O, $NR^f$ and S;

$R^f$ is H or alkyl;

$R^e$ is selected from the group consisting of H, alkyl, hydroxy and alkoxy;

X or Y are independently selected from the group consisting of —$CR^g$— or —N— wherein $R^g$ is selected from the group consisting of H, alkyl, haloalkyl, fluoro, alkoxyalkyl, alkynyl, aryl, heteroaryl, aralkyl, heteroaralkyl, alkylsulfone, hydroxyalkyl, hydroxy, alkoxy, and carboxyalkyl; or the group X—$X_2$—Y contains a moiety selected from the group consisting of acyl, alkyl, amino, ether, thioether, sulfone and olefin;

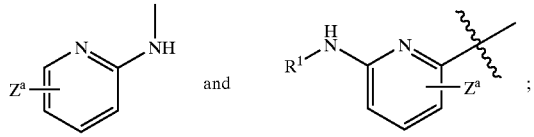

forms a cycloalkyl, optionally substituted with one or more substituent selected from the group consisting of alkyl, halogen, cyano, carboalkoxy, haloalkyl, alkoxyalkyl, alkylsulfone, aryl, heteroaryl, aralkyl, heteroaralkyl, or alkoxy; and $R^b$ is $X_3$- $R^h$ wherein $X_3$ is selected from the group consisting of O, S and $NR^1$ wherein $R^h$ and $R^j$ are independently selected from the group consisting of H, alkyl, acyl, aryl, aralkyl and alkoxyalkyl.

2. A compound according to claim 1 wherein $A^1$ is selected from the group consisting of

[structures]

$Z^a$ is selected from the group, consisting of H, alkyl, alkoxy, hydroxy, amine alkylamine, dialkylamine, carboxyl, alkoxycarbonyl, hydroxyalkyl, halogen and haloalkyl; and $R^1$ is selected from the group consisting of H, alkyl, alkoxyalkyl, acyl, haloalkyl, alkoxycarbonyl, pyridylamino, imidazolylamino, morpholinopyridine, tetrahydronaphthyridine, oxazolylamino, thiazolylamino, pyrimidinylamino, quinoline, isoquinoline, tetrahydroquinoline, imidazopyridine, benzimidazole, pyridone, and quinolone.

3. A compound according to claim 1 wherein $A^1$ is selected from the group consisting of

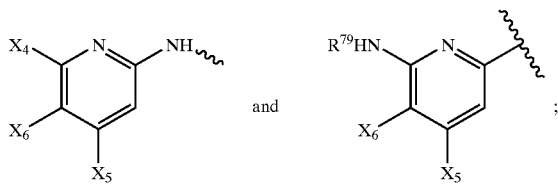

and $X^4$ is selected from the group consisting of H, alkyl, branched alkyl, alkylamino, alkoxyalkylamino, haloalkyl, thioalkyl, halogen, amino, alkoxy, aryloxy, alkoxyalkyl, hydroxy, cyano and acylamino;

$X^5$ is selected from the group consisting of H, alkyl, branched alkyl, alkylamino, alkoxyalkylamino, haloalkyl, thioalkyl, halogen, amino, alkoxy, aryloxy, alkoxyalkyl, hydroxy, cyano and acylamino;

$X^6$ is selected from the group consisting of H, alkyl, halogen, alkoxy, hydroxy, and haloalkyl; and $R^{79}$ is selected from the group consisting of hydroxy, alkoxy, alkyl and amino.

4. A compound according to the wherein the moiety $A^1$–$Z^2$ is selected from the group consisting of

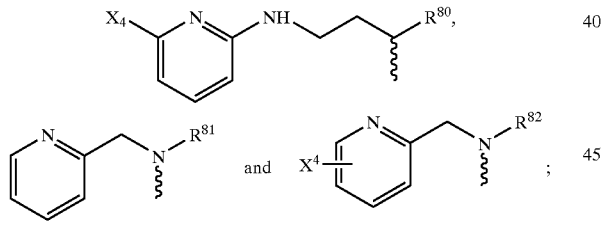

$X^4$ is selected from the group consisting of H; alkyl, branched alkyl, alkylamino, alkoxyalkylamino, haloalkyl, thioalkyl, halogen, amino, alkoxy, aryloxy, alkoxyalkyl, hydroxy, cyano and acylamino;

$R^{80}$ is selected from the group consisting of hydroxy, alkoxy, alkyl and amino;

$R^{81}$ is selected from the group consisting of hydroxy, alkoxy, alkyl and amino; and $R^{82}$ is selected from the group consisting of hydroxy, alkoxy, alkyl and amino.

5. A compound according to claim 1 wherein $X_1$ is $(CHR^p)_q$; wherein q=0;

B is a 3-, 4-, or a 5-membered cycloalkyl obtained by combining X—$X_2$—Y;

A is a phenyl ring substituted with $R^c$; and n=1.

6. A compound according to claim 5,

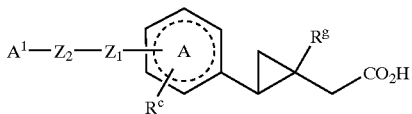

wherein the ring B is a cyclopropyl;

Y=$CR^g$;

wherein $R^g$ is selected from the group consisting of H, alkyl, haloalkyl, alkoxyalkyl, alkynyl, aryl, heteroaryl, aralkyl, heteroaralkyl, alkylsulfone, hydroxyalkyl, hydroxy, alkoxy, and carboxyalkyl;

A is a phenyl ring substituted with $R^c$; and $R^b$=OH.

7. A compound according to claim 6 wherein $R^g$ is selected from the group consisting of

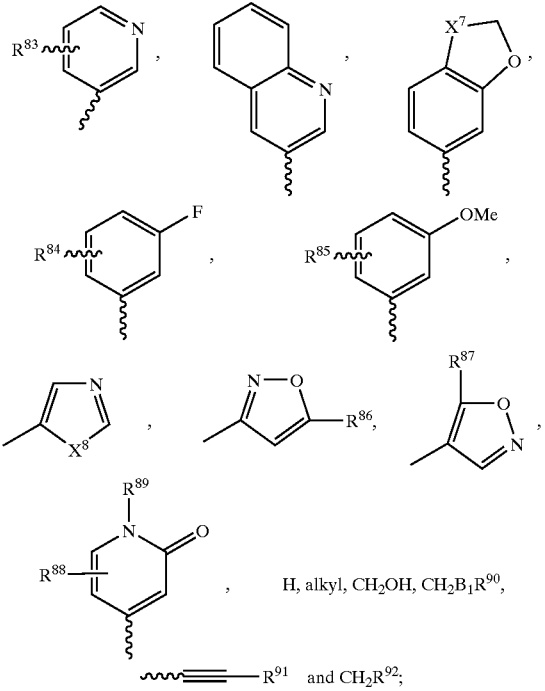

, H, alkyl, $CH_2OH$, $CH_2B_1R^{90}$, $\equiv$—$R^{91}$ and $CH_2R^{92}$;

$R^{83}$ is selected from the group consisting of H, alkyl, OMe, OH, and halogen;

$X^7$ is selected from the group consisting of CH2 and O;

$R^{84}$ is selected from the group consisting of H, alkyl, OMe, OH, and halogen;

$R^{85}$ is selected from the group consisting of H, alkyl, OMe, OH, and halogen;

$X^8$ is selected from the group consisting of NH, NMe, O, and S;

$R^{86}$ is selected from the group consisting of H and Me;

$R^{87}$ is selected from the group consisting of H and Me;

$R^{88}$ is selected from the group consisting of H, alkyl, OMe, OH, and halogen;

$R^{89}$ is selected from the group consisting of H and Me;

$B^1$ is selected from the group consisting of O, SO2, S and CO;

$R^{90}$ is selected from the group consisting of alkyl and aryl;

$R^{91}$ is selected from the group consisting of alkyl and aryl; and $R^{92}$ is selected from the group consisting of aryl and heteroaryl.

8. A compound according to claim 6 wherein $A^1$ is selected from the group consisting of

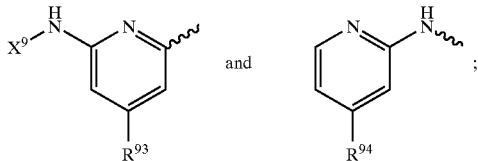

$X^9$ is selected from the group consisting of H, alkyl, and acyl;

$R^{93}$ is selected from the group consisting of H, Me, OH and alkoxyalkyl; and $R^{93}$ is selected from the group consisting of H, Me, OMe, and OH.

9. A compound according to claim 6 wherein ring A is a phenyl ring; and $Z_1$-$Z_2$ and $X_1$-X are connected para to each other.

10. A compound according to claim 9 wherein the phenyl ring is optionally substituted with one or more substituents selected from the group consisting of alkyl; halogen, hydroxy, alkoxy, haloalkyl, aryl, heteroaryl, alkoxyalkyl, sulfonamide, methylenedioxy, ethylenedioxy, alkynyl, and alkynylalkyl.

11. A compound according to claim 9 wherein Z is selected from the group consisting of $CH_2$, O, $NR_2$, CO, S, SO, and $SO_2$.

12. A compound according to claim 9 wherein $A^1$ is selected from the group consisting of

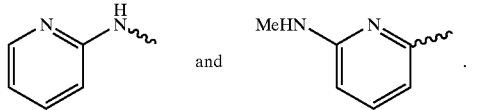

13. A compound according to the claim 1,

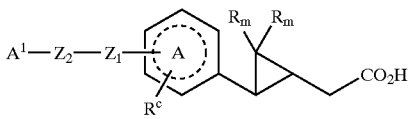

wherein $X^1$ is $(CHR^p)_q$; wherein q=o;

A is a phenyl ring substituted with $R^c$

B is a cyclopropyl obtained by combining X—$X_2$—Y;

n=1; and $R_m$ and $R_n$ are selected from the group consisting of H, alkyl, halogen, alkoxy, haloalkyl, alkoxyalkyl, alkylsulfone, cyano, carboalkoxy, aryl, heteroaryl, aralkyl and heteroaralkyl; or $R_m$ and $R_n$ form a spirocyclic ring system.

14. A compound according to the claim 13 wherein $A^1$ is selected from the group consisting of

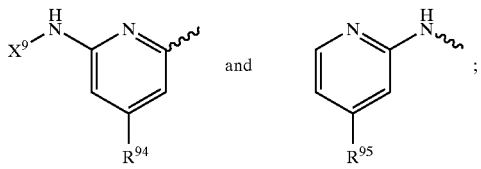

$R^{94}$ is selected from the group consisting of H, Me, OH, and alkoxyalkyl;

$R^{94}$ is selected from the group consisting of H, Me, OMe, and OH; and $X^9$ is selected from the group consisting of H, alkyl, and acyl.

15. A compound according to claim 1 selected from the group consisting of:

2-[4-[3-(2-pyridinylamino)propoxy]phenyl] cyclopropaneacetic acid;

2-[4-[3-(2-pyridinylamino)propoxy]phenyl] cyclopentaneacetic acid;

3-[4-3-(2-pyridinylamino)propoxy]phenyl] cyclopentaneacetic acid;

2,2-difluoro-3-[4-[3(2-pyridinylamino)propoxy]phenyl) cyclopropane-acetic acid (2-(4-[2-(5,6,7,8-Tetrahydro-[1,8]naphthyridin-2-yl)-ethoxy]-phenyl)-cyclopropyl)-acetic acid;

2-[3-methyl-4-[3-(2-pyridinylamino)propoxy]phenyl] cyclopropane acetic acid;

2-(2-methoxy-4-[3-(2-pyridinylamino)propoxy]phenyl) cyclopropane-acetic acid;

2-[2-methyl-4-[3-(2-pyridinylamino)propoxy]phenyl] cyclopropane-acetic acid;

2-[3-fluoroa-[3-(2-pyridinylamino)propoxy]phenyl] cyclopropaneacetic acid;

2-[2-fluoroa-[3-(2-pyridinylamino)propoxy]phenyl] cyclopropaneacetic acid;

2-[4-[2-[6-(methylamino)-2-pyridinyl]ethoxy]phenyl] cyclopropane-acetic acid;

2-[4-[2-(3,4-dihydro-2H-pyrido[3,2-b]-1,4-oxazin-6-yl) ethoxy]phenyl)-cyclopropaneacetic acid;

3-(4-[3-(2-pyridinylamino)propoxy]phenyl] cyclobutaneacetic acid;

(2-{2-Methoxy-4-[3-(pyridin-2-ylamino)-propoxy]-phenyl}-cyclopropyl)-acetic acid;

(2-{2-Fluoro-4-[3-(pyridin-2-ylamino)-propoxy]-phenyl)-cyclopropyl)-acetic acid;

(2-{2-Acetoxy4-[3-(pyridin-2-ylamino)-propoxy]-phenyl)-cyclopropyl)-acetic acid;

(1-Methyl-2- 14-[3-(pyridin-2-ylamino)-propoxy]-phenyl)-cyclopropyl)-acetic acid;

(1-Methoxymethyl-2-(4-[3-(pyridin-2-ylamino)-propoxy]-phenyl)-cyclopropyl)-acetic Acid;

(1-Methanesulfonylmethyl-2-{4-(3-(pyridin-2-ylamino)-propoxy]-phenyl}-cyclopropyl)-acetic acid;

(1-Pyridin-3-yl-2- (4-[3-(pyridin-2-ylamino)-propoxy]-phenyl)-cyclopropyl)-acetic acid;

(1-Benzo[1-3]dioxole-5-yl-2-{4-[-3-(pyridin-2-ylamino)-propoxy]-phenyl}-cyclopropyl)-acetic acid;

(1-(2-3-Dihydro-benzofuran-6-yl)-2-{4-[3-(pyridin-2-ylamino)-propoxy]-phenyl}-cyclopropyl)-acetic acid;

(1-isoxazol-3-yl-2-{4-[3-(pyridin-2-ylamino)-propoxy]-phenyl}-cyclopropyl)-acetic acid;

(1-isoxazol-5-yl-2-{4-[3-(pyridin-2-ylamino)-propoxy]-phenyl}-cyclopropyl)-acetic acid;

(1-oxazol-5-yl-2-{4-(3-(pyridin-2-ylamino)-propoxy]-phenyl}-cyclopropyl)-acetic acid;

(2-{4-[3-(Pyridin-2-ylamino)-propoxy]-phenyl}-1-thiazol-5-yl-cyclopropyl)-acetic acid;

(1-Pyridin-3-yl-2-{4-[2-(5,6,7,8-tetrahydro-[1,8]naphthyridin-2-yl)-ethoxy]-phenyl}-cyclopropyl)-acetic acid;

(1-Methyl-2-{4-[2-(6-methylamino-pyridin-2-yl)-ethoxy]-phenyl}-cyclopropyl)-acetic acid;

(2-{4-[2-(6-Ethylamino-pyridin-2-yl)-ethoxy]-phenyl}-1-methyl-cyclopropyl)-acetic acid;

[2-(4-(2-[6-(2-Methoxy-ethylamino)-pyridin-2-yl]-ethoxy 1-phenyl)-1-methyl-cyclopropyl]-acetic acid;

[2-(4-{2-(6-(3-Methoxy-propylamino)-pyridin-2-yl]-ethoxy}-phenyl)-1-methyl-cyclopropyl]-acetic acid;

(2-{4-[2-(6-Acetylamino-pyridin-2-yl)-ethoxy]-phenyl}-1-methyl-cyclopropyl)-acetic acid;

[1-Methyl-2-(4-{2-(6-(2,2,2-trifluoro-ethylamino)-pyridin-2-yl]-ethoxy}-phenyl)-cyclopropyl]-acetic acid;

(2-{4-[2-[6-Ethylamino-pyridin-2-yl)-ethoxy]-phenyl}-cyclopropyl)-acetic acid;

[2-(4-{2-[6-(2-Methoxy-ethylamino)-pyridin-2-yl]-ethoxy}-phenyl)-cyclopropyl-acetic acid;

[2-(4-{2-[6-(2,2,2-Trifluoro-ethylamino)-pyridin-2-yl]-ethoxy}-phenyl)-cyclopropyl]-acetic acid;

[2-(4-{2-(6-(3-Methoxy-propylamino)-pyridin-2-yl]-ethoxy}-phenyl)-cyclopropyl]-acetic acid; and (2-{4-[2-(6-Acetylamino-pyridin-2-yl)-ethoxy]-phenyl}-cyclopropyl)-acetic acid.

16. A pharmaceutical composition comprising a therapeutically effective amount of a compound of claim 1 and a pharmaceutically acceptable carrier.

17. A pharmaceutical composition comprising a therapeutically effective amount of a compound of claim 5 and a pharmaceutically acceptable carrier.

18. A method for treating conditions mediated by the $\alpha_v\beta_3$ integrin in a mammal in need of such treatment comprising administering an effective $\alpha_v\beta_3$ inhibiting amount of a compound of claim 16.

19. A method for treating conditions mediated by the $\alpha_v\beta_3$ integrin in a mammal in need of such treatment comprising administering an effective $\alpha_v\beta_3$ inhibiting amount of a compound of claim 5.

20. The method according to claim 18 wherein the condition treated is tumor metastasis.

21. The method according to claim 19 wherein the condition treated is tumor metastasis.

22. The method according to claim 18 wherein the condition treated is solid tumor growth.

23. The method according to claim 19 wherein the condition treated is solid tumor growth.

24. The method according to claim 18 wherein the condition treated is angiogenesis.

25. The method according to claim 19 wherein the condition treated is angiogenesis.

26. The method according to claim 18 wherein the condition treated is osteoporosis.

27. The method according to claim 19 wherein the condition treated is osteoporosis.

28. The method according to claim 18 wherein the condition treated is humoral hypercalcemia of malignancy.

29. The method according to claim 19 wherein the condition treated is humoral hypercalcemia of malignancy.

30. The method according to claim 18 wherein the condition treated is smooth muscle cell migration.

31. The method according to claim 19 wherein the condition treated is smooth muscle cell migration.

32. The method according to claim 18 wherein restenosis is inhibited.

33. The method according to claim 19 wherein restenosis is inhibited.

34. The method according to claim 18 wherein atherosclerosis is inhibited.

35. The method according to claim 19 wherein atherosclerosis is inhibited.

36. The method according to claim 18 wherein macular degeneration is inhibited.

37. The method according to claim 19 wherein macular degeneration is inhibited.

38. The method according to claim 18 wherein retinopathy is inhibited.

39. The method according to claim 19 wherein retinopathy is inhibited.

40. The method according to claim 18 wherein arthritis is inhibited.

41. The method according to claim 19 wherein arthritis is inhibited.

42. A method for treating conditions mediated by the $\alpha_v\beta_3$ $\alpha_v\beta_5$ integrin in a mammal in need of such treatment comprising administering an effective $\alpha_v\beta_5$ inhibiting amount of a compound of claim 1.

43. A method for treating conditions mediated by the $\alpha_v\beta_5$ integrin in a mammal in need of such treatment comprising administering an effective intearin inhibiting amount of a compound of claim 1.

44. The method according to claim 42 wherein the condition treated is $\alpha_v\beta_5$ integrin mediated-tumor metastasis.

45. The method according to claim 43 wherein the condition treated is $\alpha_v\beta_5$ integrin mediated-tumor metastasis.

46. The method according to claim 42 wherein the condition treated is $\alpha_v\beta_5$ integrin mediated-solid tumor growth.

47. The method according to claim 43 wherein the condition treated is $\alpha_v\beta_5$ integrin mediated-solid tumor growth.

48. The method according to claim 42 wherein the condition treated is angiogenesis.

49. The method according to claim 43 wherein the condition treated is angiogenesis.

50. The method according to claim 42 wherein the condition treated is osteoporosis.

51. The method according to claim 43 wherein the condition treated is osteoporosis.

52. The method according to claim 42 wherein the condition treated is humoral hypercalcemia of malignancy.

53. The method according to claim 43 wherein the condition treated is humoral hypercalcemia of malignancy.

54. The method according to claim 42 wherein the condition treated is smooth muscle cell migration.

55. The method according to claim 43 wherein the condition treated is smooth muscle cell migration.

56. The method according to claim 42 wherein restenosis is inhibited.

57. The method according to claim 43 wherein restenosis is inhibited.

58. The method according to claim 42 wherein atherosclerosis is inhibited.

59. The method according to claim 43 wherein atherosclerosis is inhibited.

60. The method according to claim 42 wherein macular degeneration is inhibited.

61. The method according to claim 43 wherein macular degeneration is inhibited.

62. The method according to claim 42 wherein retinopathy is inhibited.

63. The method according to claim 43 wherein retinopathy is inhibited.

64. The method according to claim 42 wherein arthritis is inhibited.

65. The method according to claim 43 wherein arthritis is inhibited.

* * * * *